(12) United States Patent
Wang et al.

(10) Patent No.: US 10,647,665 B2
(45) Date of Patent: May 12, 2020

(54) BIARYL UREA DERIVATIVE OR SALT THEREOF AND PREPARATION PROCESS AND USE FOR THE SAME

(71) Applicant: Fudan University, Shanghai (CN)

(72) Inventors: Yonghui Wang, Shanghai (CN); Yafei Huang, Shanghai (CN); Fazhi Yu, Shanghai (CN); Ting Tang, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 16/312,436

(22) PCT Filed: Jun. 19, 2017

(86) PCT No.: PCT/CN2017/088956
§ 371 (c)(1),
(2) Date: Dec. 21, 2018

(87) PCT Pub. No.: WO2017/219935
PCT Pub. Date: Dec. 28, 2017

(65) Prior Publication Data
US 2019/0248737 A1 Aug. 15, 2019

(30) Foreign Application Priority Data

Jun. 22, 2016 (CN) .......................... 2016 1 0455177
Jun. 22, 2016 (CN) .......................... 2016 1 0455207

(51) Int. Cl.
| | | |
|---|---|---|
| *C07C 275/00* | (2006.01) | |
| *C07D 213/55* | (2006.01) | |
| *C07C 311/51* | (2006.01) | |
| *C07C 311/08* | (2006.01) | |
| *C07C 311/03* | (2006.01) | |
| *A61P 1/00* | (2006.01) | |
| *A61K 31/17* | (2006.01) | |
| *C07D 213/71* | (2006.01) | |
| *A61P 17/06* | (2006.01) | |
| *C07C 381/10* | (2006.01) | |
| *A61K 31/18* | (2006.01) | |
| *C07C 311/47* | (2006.01) | |
| *A61P 19/02* | (2006.01) | |
| *C07C 275/32* | (2006.01) | |
| *C07D 213/70* | (2006.01) | |
| *C07C 317/32* | (2006.01) | |
| *A61P 11/06* | (2006.01) | |
| *A61P 29/00* | (2006.01) | |
| *A61P 37/02* | (2006.01) | |
| *A61P 35/00* | (2006.01) | |
| *C07D 213/40* | (2006.01) | |
| *C07D 231/12* | (2006.01) | |

(52) U.S. Cl.
CPC ............ *C07C 275/00* (2013.01); *A61K 31/17* (2013.01); *A61K 31/18* (2013.01); *A61P 1/00* (2018.01); *A61P 11/06* (2018.01); *A61P 17/06* (2018.01); *A61P 19/02* (2018.01); *A61P 29/00* (2018.01); *A61P 35/00* (2018.01); *A61P 37/02* (2018.01); *C07C 275/32* (2013.01); *C07C 311/03* (2013.01); *C07C 311/08* (2013.01); *C07C 311/47* (2013.01); *C07C 311/51* (2013.01); *C07C 317/32* (2013.01); *C07C 381/10* (2013.01); *C07D 213/40* (2013.01); *C07D 213/55* (2013.01); *C07D 213/70* (2013.01); *C07D 213/71* (2013.01); *C07D 231/12* (2013.01)

(58) Field of Classification Search
CPC .................................................... C07C 275/00
USPC ........................................................ 514/347
See application file for complete search history.

(56) References Cited

U.S. PATENT DOCUMENTS

2014/0296256 A1   10/2014   Miyata et al.

FOREIGN PATENT DOCUMENTS

| CN | 1215990 A | 5/1999 |
|---|---|---|
| CN | 1539816 A | 10/2004 |
| CN | 1635979 A | 7/2005 |
| CN | 1678573 A | 10/2005 |
| CN | 1714076 A | 12/2005 |
| CN | 1809570 A | 7/2006 |
| CN | 102378753 A | 3/2012 |
| CN | 102666498 A | 9/2012 |

(Continued)

OTHER PUBLICATIONS

Registry, "CAS RN 935", 27.0033 STN Files: CHEMCATS, Apr. 13, 2017.

(Continued)

*Primary Examiner* — Taofiq A Solola
(74) *Attorney, Agent, or Firm* — Fitch, Even, Tabin & Flannery, LLP

(57) ABSTRACT

The present invention discloses a biaryl urea RORγt inhibitor, and specifically relates to a biaryl urea derivative, as represented by formula I, with an RORγt inhibiting activity, and a preparation process thereof, and a pharmaceutical composition comprising the compound. Further disclosed is use of the compound for treating an RORγt-related disease.

(I)

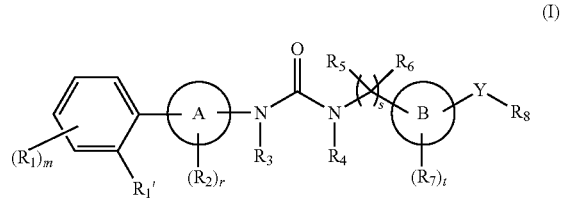

10 Claims, No Drawings

(56) References Cited

FOREIGN PATENT DOCUMENTS

| CN | 103221388 A | 7/2013 |
|---|---|---|
| EP | 2990057 A1 | 2/2016 |
| WO | 97/29743 A1 | 8/1997 |
| WO | 199729743 A1 | 8/1997 |
| WO | 99/38846 A1 | 8/1999 |
| WO | 200168568 A2 | 9/2001 |
| WO | 03/000245 A1 | 1/2003 |
| WO | 03/066581 A1 | 8/2003 |
| WO | 2004/022529 A2 | 3/2004 |
| WO | 2004/046090 A2 | 6/2004 |
| WO | 2004108729 A1 | 12/2004 |
| WO | 2009/074749 A2 | 6/2009 |
| WO | 2011025965 A1 | 3/2011 |
| WO | 2011098610 A1 | 8/2011 |
| WO | 2012021963 A1 | 2/2012 |
| WO | 2013/029338 A1 | 3/2013 |

OTHER PUBLICATIONS

International Search Report for PCT/CN2017/088956 dated Oct. 19, 2017 and English Translation (9 pages).
European Patent Office, Extended European Search Report for European Patent Application No. 17814673.4 dated Oct. 16, 2019, 10 pages.
le;2qDatabase Registry [Online] Chemical Abstracts Service, Columbus, Ohio, US; May 6, 2016, Aurora Fine Chemicals, "4-[[[([1,1'-biphenyl]-4-ylamino)carbonyl]amino]methyl]-benzenesulfonamide," XP055628348, Database Accession No. RN-1904954-76-2, 1 page.
Database Registry [Online] Chemical Abstracts Service, Columbus, OH, US; May 1, 2016, Aurora Fine Chemicals, "Benzoic acid, 4-[[[([1,1'-biphenyl]-4-ylamino)carbonyl]amino]methyl]," XP055628349, Database Accession No. RN-1901278-91-8, 1 page.
Database Registry [Online] Chemical Abstracts Service, Columbus, OH, US; Feb. 15, 2015, Ukrorgsyntez Ltd., "Urea, N'-[1,1'-biphenyl]-4-yl-N-methyl-N-[1-[4-(methylsulfonyl)phenyl]ethyl]-," XP055628350, Database Accession No. RN-1647447-27-5, 1 page.
Database Registry [Online] Chemical Abstracts Service, Columbus, OH, US; Apr. 13, 2007, Enamine, "Benzenemethanesulfonamide, 4-[[[([1,1'-biphenyl]-4-ylamino)carbonyl]amino]methyl]-N-(1-methylethyl)-," XP055628351, Database Accession No. RN-930033-27-5, 1 page.
STN International Database, CAS Registry No. 1901278-91-8, May 1, 2016, 1 page.

BIARYL UREA DERIVATIVE OR SALT THEREOF AND PREPARATION PROCESS AND USE FOR THE SAME

CROSS-REFERENCE TO RELATED APPLICATIONS

This application is a U.S. national phase application filed under 35 U.S.C. § 371 of International Application PCT/CN2017/088956, filed Jun. 19, 2017, designating the United States, which claims priority from Chinese Application Number 201610455177.X, filed Jun. 22, 2016, and Chinese Application Number 201610455207.7, filed Jun. 22, 2016.

FIELD OF THE INVENTION

The present invention belongs to the technical field of chemical pharmaceuticals, and generally relates to a novel biaryl urea derivative with an RORγt inhibiting activity represented by general formula I or salts thereof and a preparation process thereof, and further relates to use of such a compound for treating an RORγt-related disease.

DESCRIPTION OF THE PRIOR ART

Retinoic acid receptor-related orphan receptors (RORs), also known as NF1R, are members of the ligand-dependent transcription factor nuclear receptor superfamily. The ROR subfamily mainly includes three members: RORα, RORβ and RORγ. There are two different subtypes of RORγ: RORγ1 and RORγt (also known as RORγ2). RORγ1 is distributed in skeletal muscle, thymus, testis, pancreas, prostate, heart, and liver, etc., while RORγt is only expressed in some immune cells.

Littman et al. first reports that RORγt is required for the differentiation of naive CD4+ T cells into Th17 cells. During the differentiation of antigen-stimulated Thp cells into Th17 cells, RORγt is expressed under the inducing effect of cytokines such as IL-6, IL-21 and TGF-β. Thp cells isolated from RORγt-deficient mice have obviously decreased differentiation into Th17 cell lines. These all indicate that RORγt is the key regulatory factor to promote the differentiation of Th17 cells.

Th17 cell is one of helper T cells, and may produce IL-17 and other pro-inflammatory cytokines. Th17 cells have key functions in many mouse autoimmune disease models, such as animal models of experimental allergic encephalomyelitis (EAE) and collagen-induced arthritis (CIA). In addition, elevated IL-17 levels can be detected in some human autoimmune diseases such as rheumatoid arthritis (RA), multiple sclerosis (MS), psoriasis and inflammatory bowel disease (IBD). The increased Th17 cells are found in tissues and peripheral blood samples of patients with autoimmune diseases. Therefore, Th17 cells or IL-17 cytokine produced by Th17 cells are closely related to the pathogenesis of inflammation and autoimmune diseases.

In January 2015, Cosentyx (Secukinumab/AIN457), a monoclonal antibody developed by Novartis that is used for treatment of psoriasis by specifically blocking IL-17, has been approved to launch in the markets by FDA. This is the first drug that acts on IL-17 in drugs for treatment of psoriasis. This also highlights the importance of the IL-17 signaling pathway in inflammatory diseases and demonstrates the potential for treatment of inflammatory diseases by affecting the IL-17 signaling pathway with RORγt inhibitors.

Therefore, RORγt can be used as a new target for the treatment of autoimmune diseases. It is of great significance to search for small-molecule modulators for RORγt and use them in the treatment of RORγt-mediated inflammation and autoimmune diseases.

SUMMARY OF THE INVENTION

The present invention provides a class of novel biaryl urea compound represented by general formula I and pharmaceutically acceptable salts thereof:

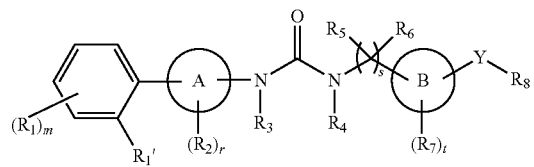

wherein:
A is a phenyl or heteroaryl;
B is a phenyl or heteroaryl;
$R_1$ is optionally selected from a group consisting of hydrogen, methyl, halogen, cyano, hydroxy, —$CF_3$, —$CHF_2$, and —$CH_2F$;
$R_1'$ is optionally selected from a group consisting of hydrogen, halogen, cyano, hydroxy, $C_1$-$C_6$ alkyl, halogen-substituted $C_1$-$C_6$ alkyl, $C(O)OR_a$ or cycloalkyl-substituted $C_1$-$C_6$ alkyl, $C_3$-$C_6$ cycloalkyl, $C_3$-$C_6$ oxo(azo)heterocycloalkyl, $C_1$-$C_6$ alkoxyl, halogen-substituted $C_1$-$C_6$ alkoxyl, hydroxy or $C_1$-$C_3$ alkoxyl-substituted $C_1$-$C_3$ alkyl, phenyl, substituted phenyl, phenoxyl, substituted phenoxyl, heterocyclyl, heterocyclooxyl, heteroaryl, heteroaryloxyl, $C_2$-$C_6$ alkenyl, halogen-substituted aromatic ketone group, —$C(O)R_a$, —$(CH_2)_nNR_{a1}R_{a2}$, —$(CH_2)_nC(O)OR_a$ and —$C(O)NR_{a1}R_{a2}$;
$R_2$ is optionally selected from a group consisting of hydrogen, halogen, cyano, hydroxyl, $C_1$-$C_6$ alkyl, halogen-substituted $C_1$-$C_6$ alkyl, $C(O)OR_a$ or cycloalkyl substituted $C_1$-$C_6$ alkyl, $C_3$-$C_6$ cycloalkyl, $C_3$-$C_6$ oxo(azo)heterocycloalkyl, $C_1$-$C_6$ alkoxyl, halogen-substituted $C_1$-$C_6$ alkoxyl, hydroxyl or $C_1$-$C_3$ alkoxyl substituted $C_1$-$C_3$ alkyl, phenyl, substituted phenyl, phenoxyl, substituted phenoxyl, heterocyclyl, heterocyclooxyl, heteroaryl, heteroaryloxyl, $C_2$-$C_6$ alkenyl, halogen-substituted aromatic ketone group, carboxyl or cyano substituted heteroaryl, —$C(O)R_a$, —$(CH_2)_nNR_{a1}R_{a2}$, —$(CH_2)_nC(O)OR_a$ and —$C(O)NR_{a1}R_{a2}$;
$R_3$ and $R_4$ are each independently selected from a group consisting of hydrogen, $C_1$-$C_3$ alkyl, halogen-substituted $C_1$-$C_3$ alkyl, $C_3$-$C_6$ cycloalkyl and $C_1$-$C_3$ oxo(azo)heterocycloalkyl;
$R_5$ and $R_6$ are each independently selected from a group consisting of hydrogen, halogen, cyano, hydroxyl, $C_1$-$C_3$ alkyl, halogen-substituted $C_1$-$C_3$ alkyl, hydroxyl or $C_1$-$C_3$ alkoxyl substituted $C_1$-$C_3$ alkyl, $C_1$-$C_3$ alkoxyl, halogen-substituted $C_1$-$C_3$ alkoxyl, $C_3$-$C_6$ cycloalkyl and $C_3$-$C_6$ oxo(zao)heterocycloalkyl, and $R_5$ and $R_6$ may also be bonded to form a $C_3$-$C_6$ ring;
$R_7$ is optionally selected from a group consisting of hydrogen, halogen, cyano, hydroxyl, $C_1$-$C_6$ alkyl, halogen-substituted $C_1$-$C_6$ alkyl, $C(O)OR_a$ or cycloalkyl substituted $C_1$-$C_6$ alkyl, $C_3$-$C_6$ cycloalkyl, $C_3$-$C_6$ oxo(azo)heterocycloalkyl, $C_1$-$C_6$ alkoxyl, halogen-substituted $C_1$-$C_6$ alkoxyl, hydroxyl or $C_1$-$C_3$ alkoxyl substituted $C_1$-$C_3$ alkyl, phenyl, substituted phenyl, phenoxyl, substituted phenoxyl, heterocyclyl, heterocyclooxyl, heteroaryl, heteroaryloxyl, $C_2$-$C_6$ alkenyl, halogen-substituted aromatic ketone group, carboxyl or cyano substituted heteroaryl, —C(O)$R_a$, —(CH$_2$)$_n$NR$_{a1}$R$_{a2}$, —(CH$_2$)$_n$C(O)OR$_a$ and —C(O)NR$_{a1}$R$_{a2}$;

Y is a covalent bond, —NR$_a$—, —O—, —NR$_a$CR$_{a1}$R$_{a2}$—, —OCR$_{a1}$R$_{a2}$—, —CR$_{a1}$R$_{a2}$— or —C(O)NR$_a$—;

$R_8$ is selected from

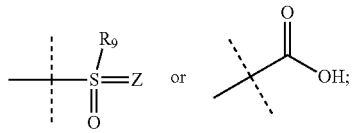

$R_9$ is selected from a group consisting of hydroxyl, $C_1$-$C_6$ alkyl, halogen-substituted $C_1$-$C_6$ alkyl, hydroxyl or $C_1$-$C_3$ alkoxyl substituted $C_1$-$C_3$ alkyl, $C_2$-$C_6$ alkenyl, —(CH$_2$)$_n$NR$_{a1}$R$_{a2}$ and —NHC(O)CH$_3$;

Z is O or NR$_a$;

$R_a$, $R_{a1}$ and $R_{a2}$ are each independently selected from hydrogen or $C_1$-$C_3$ alkyl; and m, r, t, n and s are each independently selected from any integer value of 0 to 2.

Preferably, A is a phenyl.

Preferably, s is 1.

Preferably, the structure of the novel biaryl urea compound provided in the present invention is as shown by general formula II:

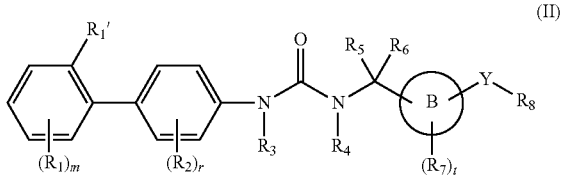

wherein:

B is phenyl or heteroaryl;

$R_1$ is optionally selected from a group consisting of hydrogen, methyl, halogen, cyano, hydroxyl, —CF$_3$, —CHF$_2$, and —CH$_2$F;

$R_1'$ is optionally selected from a group consisting of hydrogen, halogen, cyano, hydroxyl, $C_1$-$C_6$ alkyl, halogen substituted $C_1$-$C_6$ alkyl, C(O)OR$_a$ or cycloalkyl substituted $C_1$-$C_6$ alkyl, $C_3$-$C_6$ cycloalkyl, $C_3$-$C_6$ oxo(azo)heterocycloalkyl, $C_1$-$C_6$ alkoxyl, halogen-substituted $C_1$-$C_6$ alkoxyl, hydroxyl or $C_1$-$C_3$ alkoxyl substituted $C_1$-$C_3$ alkyl, phenyl, substituted phenyl, phenoxyl, substituted phenoxyl, heterocyclyl, heterocyclooxyl, heteroaryl, heteroaryloxyl, $C_2$-$C_6$ alkenyl, halogen substituted aromatic ketone group, —C(O)$R_a$, —(CH$_2$)$_n$NR$_{a1}$R$_{a2}$, —(CH$_2$)$_n$C(O)OR$_a$ and —C(O)NR$_{a1}$R$_{a2}$;

$R_2$ is optionally selected from a group consisting of hydrogen, halogen, cyano, hydroxyl, $C_1$-$C_6$ alkyl, halogen-substituted $C_1$-$C_6$ alkyl, C(O)OR$_a$ or cycloalkyl substituted $C_1$-$C_6$ alkyl, $C_3$-$C_6$ cycloalkyl, $C_3$-$C_6$ oxo(azo)heterocycloalkyl, $C_1$-$C_6$ alkoxyl, halogen-substituted $C_1$-$C_6$ alkoxyl, hydroxyl or $C_1$-$C_3$ alkoxyl substituted $C_1$-$C_3$ alkyl, phenyl, substituted heteroaryloxyl, $C_2$-$C_6$ alkenyl, halogen substituted aromatic ketone group, carboxyl or cyano substituted heteroaryl, —C(O)$R_a$, —(CH$_2$)$_n$NR$_{a1}$R$_{a2}$, —(CH$_2$)$_n$C(O)OR$_a$, and —C(O)NR$_{a1}$R$_{a2}$;

$R_3$ and $R_4$ are each independently selected from a group consisting of hydrogen, $C_1$-$C_3$ alkyl, halogen-substituted $C_1$-$C_3$ alkyl, $C_3$-$C_6$ cycloalkyl and $C_3$-$C_6$ oxo(azo)heterocycloalkyl;

$R_5$ and $R_6$ each independently selected from a group consisting of hydrogen, halogen, cyano, hydroxyl, $C_1$-$C_3$ alkyl, halogen-substituted $C_1$-$C_3$ alkyl, hydroxyl or $C_1$-$C_3$ alkoxyl substituted $C_1$-$C_3$ alkyl, $C_1$-$C_3$ alkoxyl, halogen-substituted $C_1$-$C_3$ alkoxyl, $C_3$-$C_6$ cycloalkyl and $C_3$-$C_6$ oxo(azo)heterocycloalkyl, and $R_5$ and $R_6$ may also be bonded to form a $C_3$-$C_6$ ring;

$R_7$ is optionally selected from a group consisting of hydrogen, halogen, cyano, hydroxyl, $C_1$-$C_6$ alkyl, halogen-substituted $C_1$-$C_6$ alkyl, C(O)OR$_a$ or cycloalkyl substituted $C_1$-$C_6$ alkyl, $C_3$-$C_6$ cycloalkyl, $C_3$-$C_6$ oxo(azo)heterocycloalkyl, $C_1$-$C_6$ alkoxyl, halogen-substituted $C_1$-$C_6$ alkoxyl, hydroxyl or $C_1$-$C_3$ alkoxyl substituted $C_1$-$C_3$ alkyl, phenyl, substituted phenyl, phenoxyl, substituted phenoxyl, heterocyclyl, heterocyclooxyl, heteroaryl, heteroaryloxyl, $C_2$-$C_6$ alkenyl, halogen-substituted aromatic ketone group, carboxyl or cyano substituted heteroaryl, —C(O)$R_a$, —(CH$_2$)$_n$NR$_{a1}$R$_{a2}$, —(CH$_2$)$_n$C(O)OR$_a$ and —C(O)NR$_{a1}$R$_{a2}$;

Y is selected from a group consisting of a covalent bond, —NR$_a$—, —O—, —NR$_a$CR$_{a1}$R$_{a2}$—, —OCR$_{a1}$R$_{a2}$—, —CR$_{a1}$R$_{a2}$—, and —C(O)NR$_a$—;

$R_8$ is

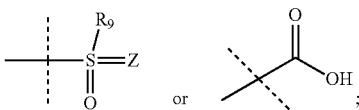

$R_9$ is selected from a group consisting of hydroxyl, $C_1$-$C_6$ alkyl, halogen-substituted $C_1$-$C_6$ alkyl, hydroxyl or $C_1$-$C_3$ alkoxyl substituted $C_1$-$C_3$ alkyl, $C_2$-$C_6$ alkenyl, —(CH$_2$)$_n$NR$_{a1}$R$_{a2}$ and —NHC(O)CH$_3$;

Z is O or NR$_a$;

$R_a$, $R_{a1}$ and $R_a2$ are each independently selected from hydrogen or $C_1$-$C_3$ alkyl; and m, r, t and n are each independently selected from any integer value of 0~2.

Further preferably, B is a phenyl or a six-membered heteroaryl.

Further preferably, $R_3$, and $R_4$ are each independently selected from hydrogen or methyl.

Further preferably, $R_1'$ is selected from a group consisting of hydrogen, —OCF$_3$, —OCHF$_2$, —CF$_3$ and heteroaryl.

Further preferably, m is 1 and $R_1$ is selected from a group consisting of —H, —Cl, —F, and —CH$_3$.

Further preferably, r is 1 or 2 and $R_2$ is one or two groups selected from —H, —Cl, —F, —CF$_3$, —OCF$_3$, —CN, $C_1$-$C_3$ alkyl and heteroaryl.

Further preferably, Z is O or NH.

Further preferably, $R_7$ is optionally selected from hydrogen, halogen, cyano, hydroxyl, and $C_1$-$C_6$ alkyl.

Further preferably, $R_9$ is selected from a group consisting of methyl, ethyl, —NHCH$_3$, —NH$_2$ and —NHC(O)CH$_3$.

Preferably, the structure of the novel biaryl urea compound provided in the present invention is as shown in general formula III:

(III)

wherein:
X is CH or N;
$R_1$ is optionally selected from a group consisting of —H, —Cl, —F, and —CH₃;
$R_1'$ is optionally selected from a group consisting of —H, —OCF₃, —OCHF₂ and —CF₃;
$R_2$ is optimally selected from a group consisting of —H, —Cl, —F, —CF₃, —OCF₃, —CN and C₁-C₃ alkyl;
$R_3$ and $R_4$ are each independently selected from hydrogen or methyl;
$R_5$ and $R_6$ are each independently selected from a group consisting of hydrogen, halogen, cyano, hydroxyl, C₁-C₃ alkyl, halogen substituted C₁-C₃ alkyl, hydroxyl or C₁-C₃ alkoxyl substituted C₁-C₃ alkyl, C₁-C₃ alkoxyl, halogen substituted C₁-C₃ alkoxyl, C₃-C₆ cycloalkyl and C₃-C₆ oxo (azo)heterocycloalkyl, and $R_5$ and $R_6$ can be bonded to form a C₃-C₆ ring;
$R_7$ is optionally selected from a group consisting of hydrogen, halogen, cyano, hydroxyl, and C₁-C₆ alkyl;
Y is a covalent bond, —NR$_a$—, —O—, —NR$_a$CR$_{a1}$R$_{a2}$—, —OCR$_{a1}$R$_{a2}$—, —CR$_{a1}$R$_{a2}$— or —C(O)NR$_a$—;
$R_8$ is $R_9$ is selected from a group consisting of methyl, ethyl, —NHCH₃, —NH₂, and —NHC(O)CH₃;
Z is selected from O or NH;
$R_a$, $R_{a1}$ and $R_{a2}$ are each independently selected from hydrogen or C₁-C₃ alkyl; and
r and t are each independently selected from 1 or 2.

Most preferably, the biaryl urea compounds provided in the present invention include, but are not limited to, the following specific compounds:

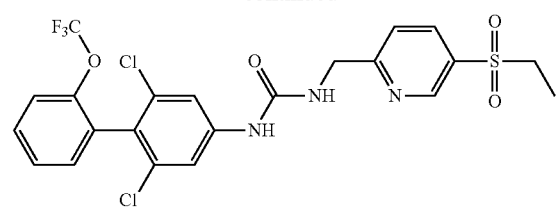
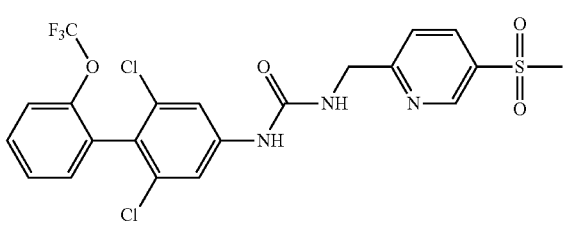
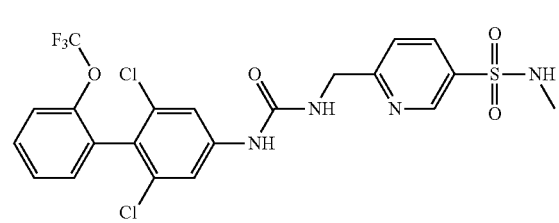
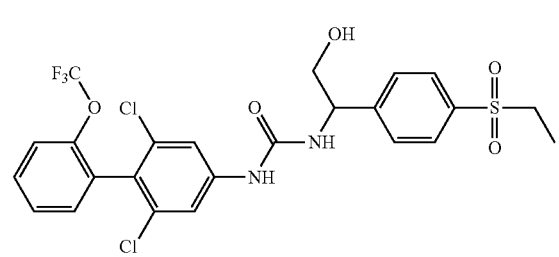
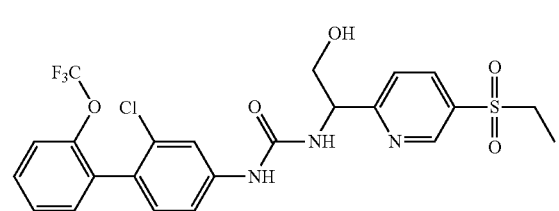
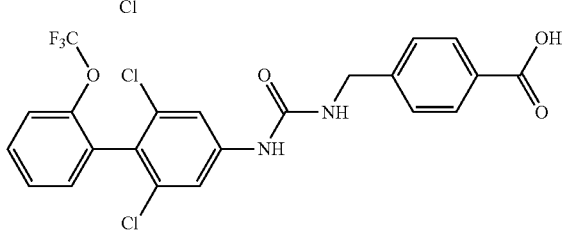
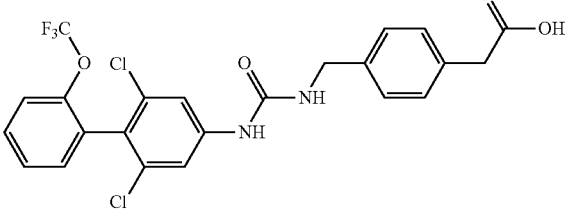
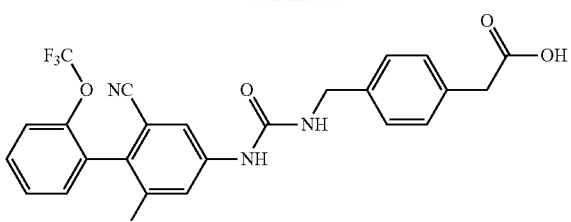
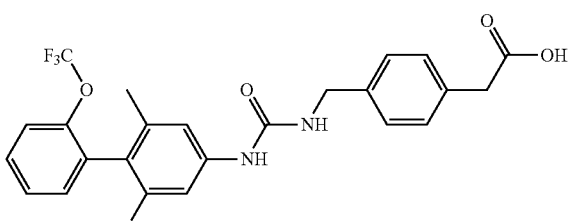
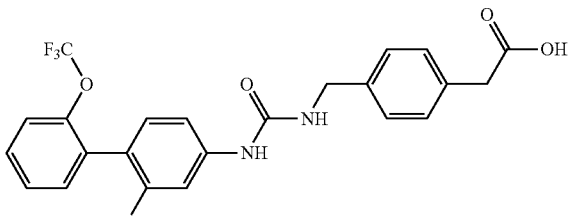
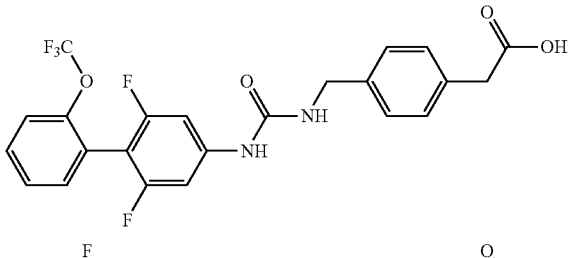
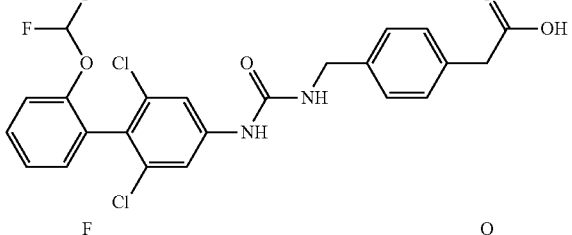
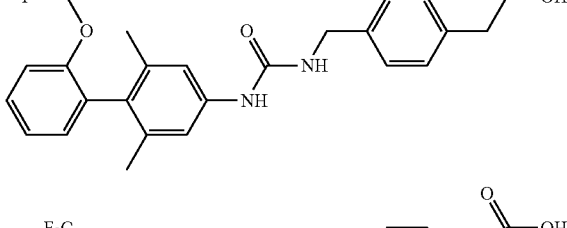
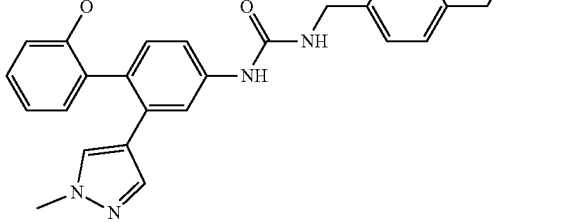

-continued
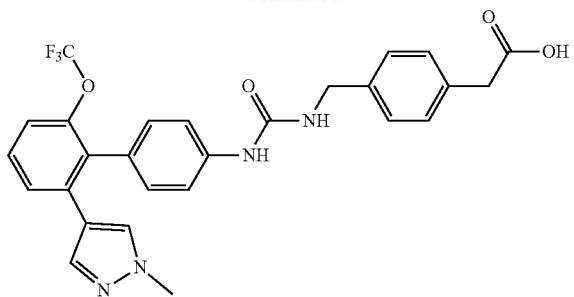
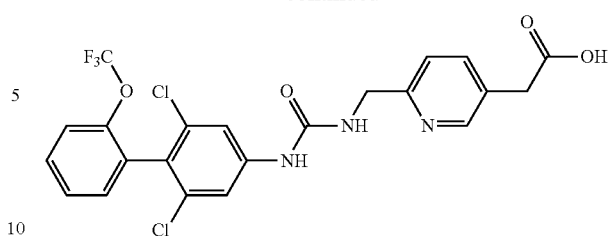
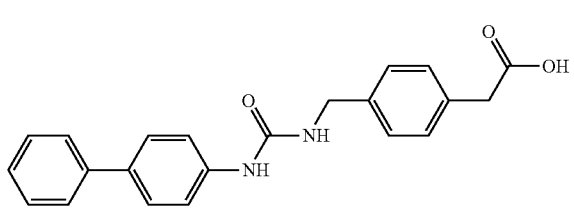
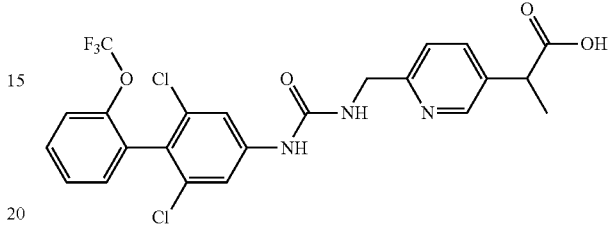
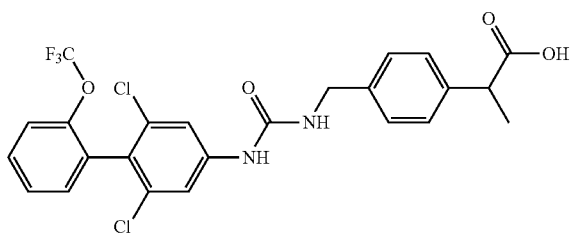
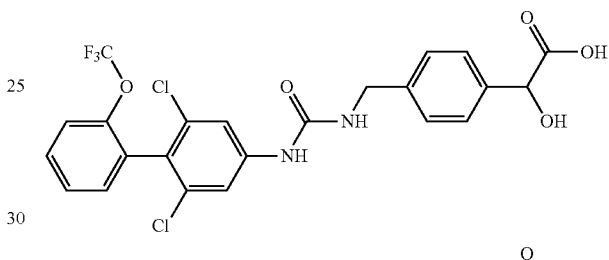
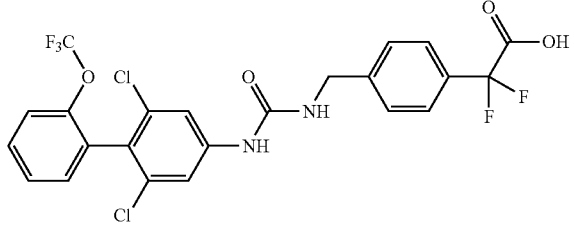
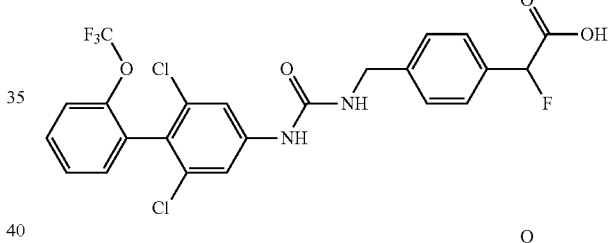
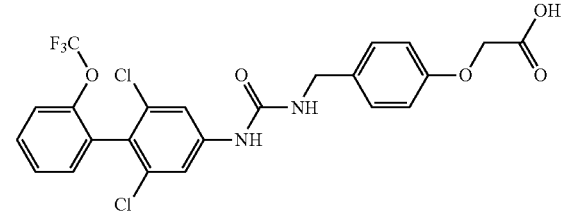
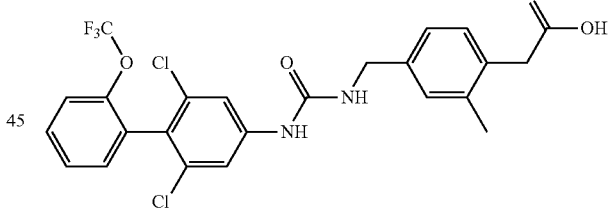
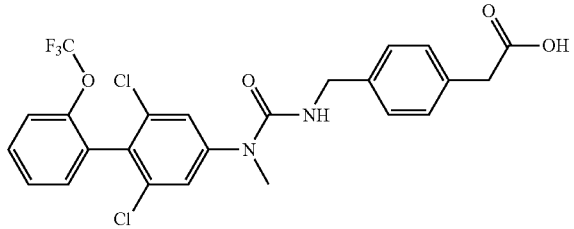
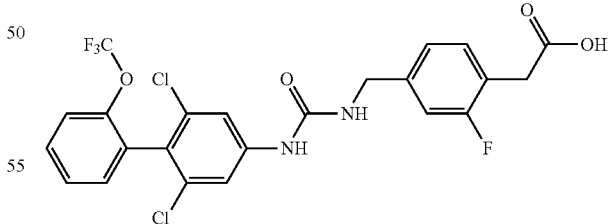
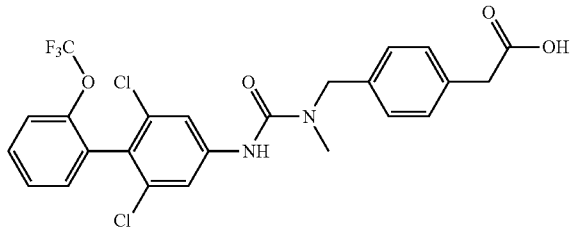
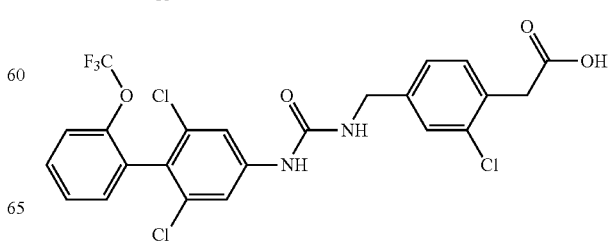

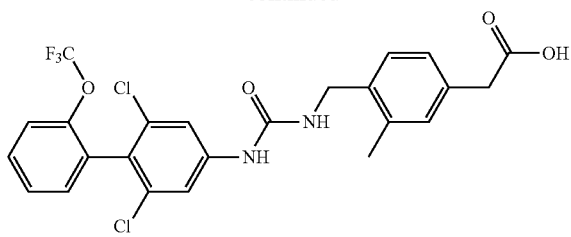
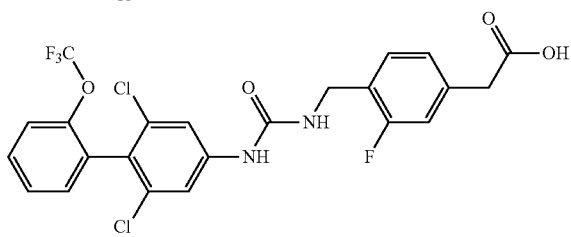
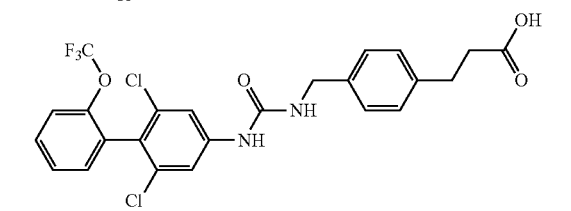
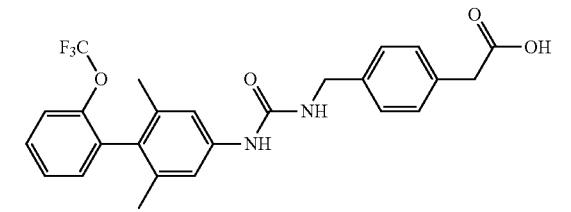
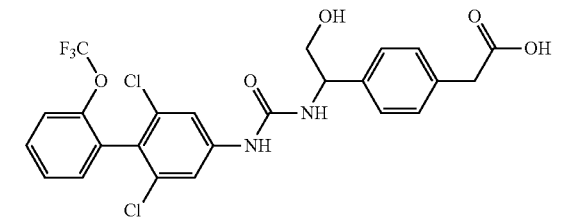
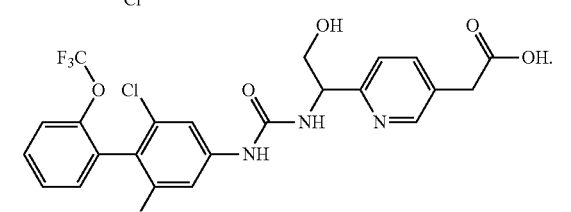

The present invention further provides a process for preparing the inventive compounds, comprising the following synthesis schemes.

Synthesis scheme 1:

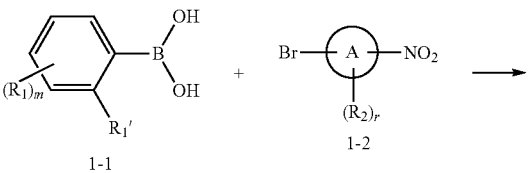

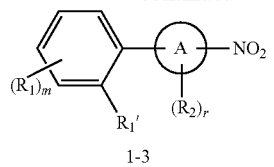

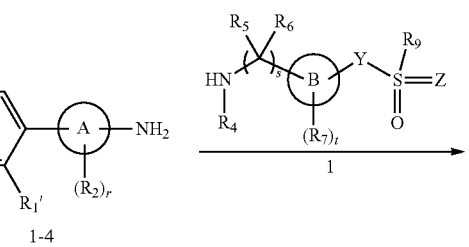

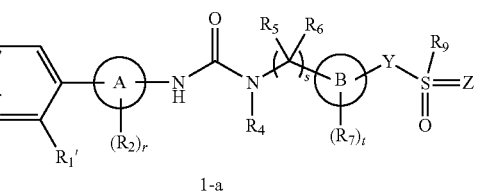

1. The compound represented by formula 1-1 and the compound represented by formula 1-2 are reacted with $Pd_2(dba)_3$, potassium phosphate and t-butyltetrafluoroborate under microwave at 110° C. to obtain a compound represented by formula 1-3.

2. The compound represented by formula 1-3 is subjected to a reaction in a solution of $SnCl_2$ and hydrochloric acid in ethanol at 60° C. to obtain a compound represented by formula 1-4.

3. The compound represented by formula 1-4 is reacted with intermediate 1 in the presence of triphosgene and N,N-diisopropylethylamine at a temperature of 0° C. to room temperature to obtain the target compound represented by formula 1-a.

Synthesis scheme 2:

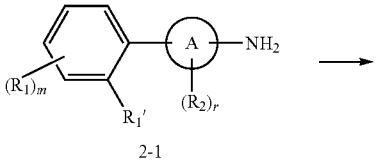

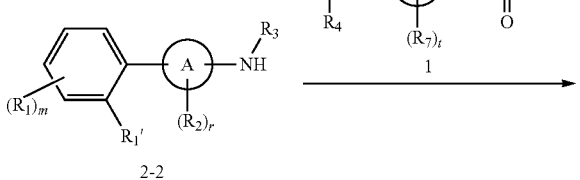

-continued

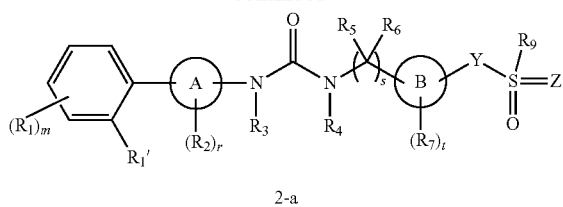

2-a

1. The compound represented by formula 2-1 is reacted with an alkyl halide at room temperature to obtain a compound represented by formula 2-2 in the presence of NaH or $K_2CO_3$.

2. The compound represented by formula 2-2 is reacted with intermediate 1 in the presence of triphosgene and N,N-diisopropylethylamine at a temperature of 0° C. to room temperature to obtain the target compound represented by formula 2-a.

Synthesis scheme 3:

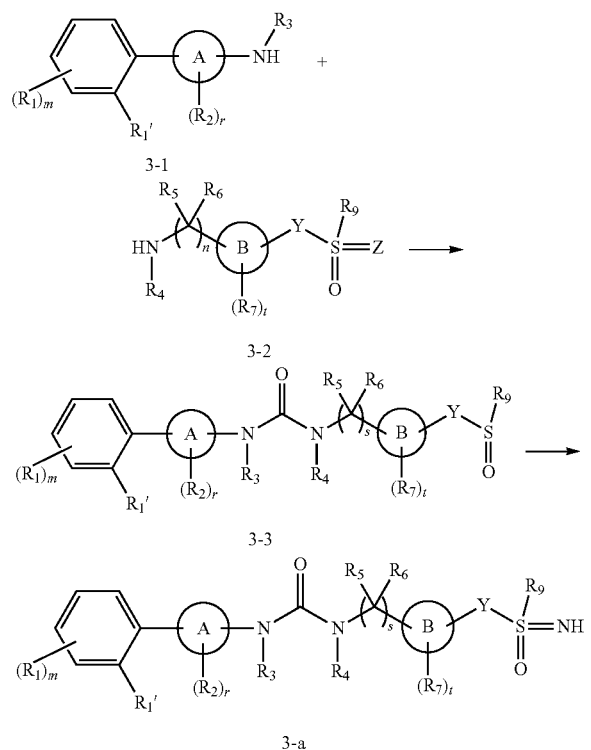

1. The compound represented by formula 3-1 is reacted with the compound represented by formula 3-2 in the presence of triphosgene and N,N-diisopropylethylamine at a temperature from 0° C. to room temperature to obtain a compound represented by formula 3-3.

2. The compound represented by formula 3-3 is first reacted with trifluoroacetamide, magnesium oxide, rhodium acetate and iodobenzene tetraacetate in dichloromethane at room temperature overnight, and then subjected to a reaction at room temperature in the presence of potassium carbonate/methanol for two hours to obtain the target compound represented by formula 3-a.

Synthesis scheme 4:

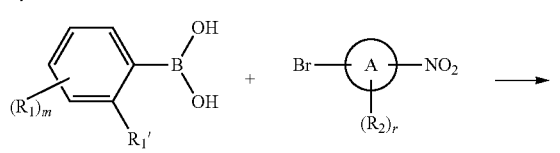

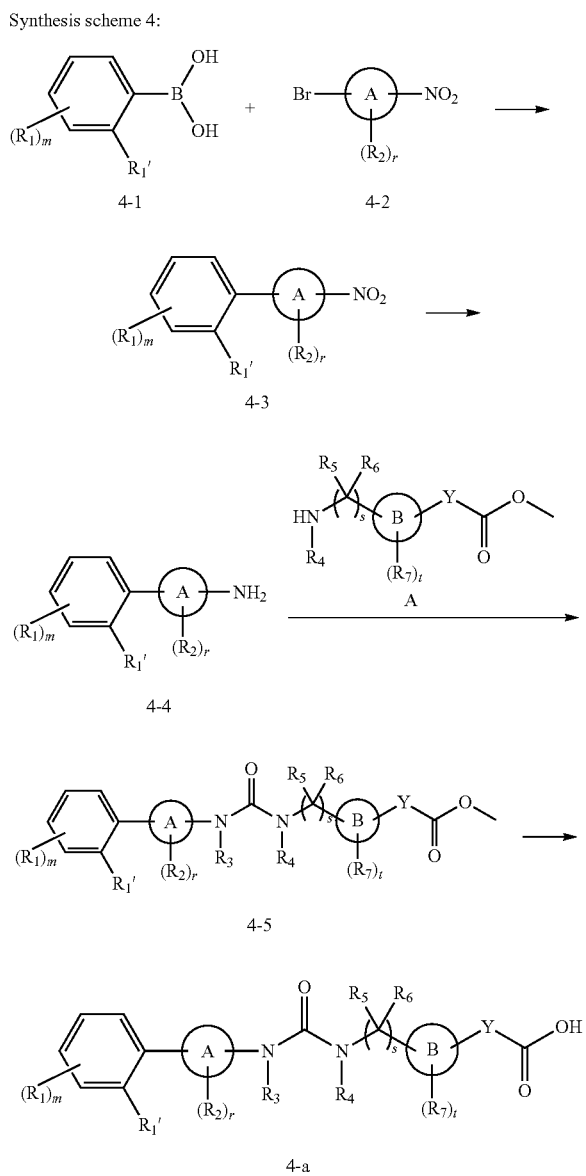

1. The compound represented by formula 4-1 is reacted with the compound represented by formula 4-2 in the presence of $Pd_2(dba)_3$, potassium phosphate or potassium carbonate and t-butyltetrafluoroborate under microwave at 110° C. to obtain a compound represented by formula 4-3.

2. The compound represented by formula 4-3 is subjected to a reaction in a solution of $SnCl_2$/hydrochloric acid in ethanol at 60° C. to obtain a compound represented by formula 4-4.

3. The compound represented by formula 4-4 is reacted with the intermediate A in the presence of triphosgene and N,N-diisopropylethylamine at a temperature of 0° C. to room temperature to obtain a compound represented by formula 4-5.

4. The compound represented by formula 4-5 is subjected to a reaction at room temperature in a solution of lithium hydroxide or sodium hydroxide in ethanol/water to obtain the target compound represented by formula 4-a.

Synthesis scheme 5:

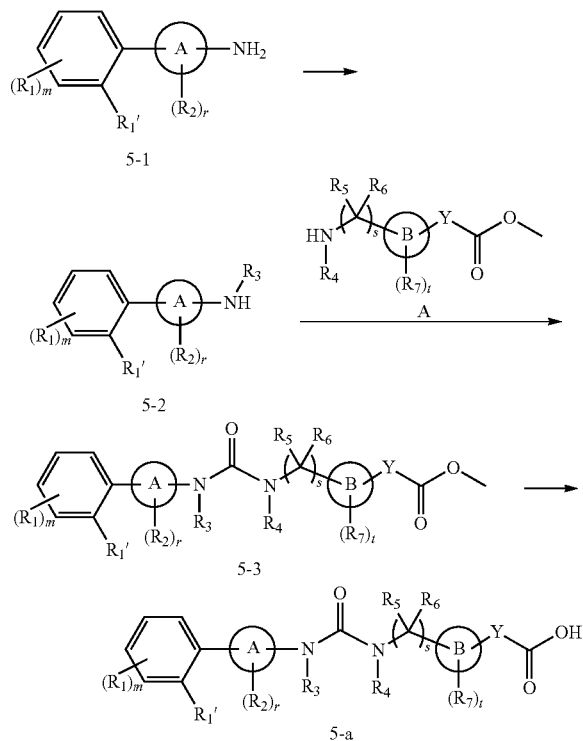

1. The compound represented by formula 5-1 is reacted with an alkyl halide in the presence of NaH or $K_2CO_3$ to obtain a compound represented by formula 5-2.

2. The compound represented by formula 5-2 is reacted with the intermediate A in the presence of triphosgene and N,N-diisopropylethylamine at a temperature of 0° C. to room temperature to obtain a compound represented by formula 5-3.

3. The compound represented by formula 5-3 is subjected to a reaction at room temperature in a solution of lithium hydroxide or sodium hydroxide in ethanol/water to obtain the target compound represented by formula 5-a.

Unless otherwise stated, the groups and terms used in the above synthesis schemes have the same meanings as those in the compounds represented by general formulas I, II and III.

The above synthesis schemes are merely illustrative of the preparation methods for some of the compounds in the present invention. For those skilled in the art, based on the above synthesis schemes, the inventive compounds can be synthesized by a similar method according to the common knowledge in the art.

The "compound", as used herein, includes all stereoisomers, geometric isomers, tautomers and isotopes.

The "compound", as used herein, may be asymmetric, for example, having one or more stereoisomers. Unless otherwise stated, all stereoisomers include, for example, enantiomers and diastereomers. The compound containing an asymmetric carbon atom herein can be isolated in an optically active pure form or in a racemic form. The optically active pure form can be resolved from racemic mixtures or can be synthesized with chiral materials or chiral reagents.

The "compound", as used herein, further includes tautomeric forms. The tautomeric form is derived from the exchange of a single bond with an adjacent double bond, accompanying with transfer of a proton.

The invention also includes atoms of all isotopes, whether in the intermediate or the final compound. The atoms of an isotope include those having the same number of atoms but different mass numbers. For example, isotopes of hydrogen include deuterium and tritium.

In the present invention, the terms used have the following meanings unless otherwise specified.

The term "halogen" means fluoro, chloro, bromo or iodo, preferably fluoro or chloro.

The term "cyano" means —CN.

The term "hydroxyl" means —OH.

The term "carboxy" means —COOH.

The term "alkyl" means a straight or branched saturated hydrocarbon group consisting of carbon atoms and hydrogen atoms, such as a $C_1$-$C_{20}$ alkyl group, preferably a $C_1$-$C_6$ alkyl, for example, methyl, ethyl, propyl (including n-propyl and isopropyl), butyl (including n-butyl, isobutyl, sec-butyl or tert-butyl), pentyl (including n-pentyl, isopentyl, neopentyl), n-hexyl, and 2-methylhexyl, etc. The alkyl group may be unsubstituted or substituted by one or more substituents including, but not limited to, alkyl, alkoxyl, cyano, hydroxyl, carbonyl, carboxyl, aryl, heteroaryl, amino, halogen, sulfonyl, sulfinyl, and phosphoryl.

The term "cycloalkyl" means a monocyclic, fused, spiro or bridged ring which solely consists of carbon, such as cyclopropyl, cyclobutyl, cyclopentyl, cyclopentenyl, cyclohexyl, spiro[3.4]octyl, and bicyclic [3.1.1] hexyl.

The term "heterocycloalkyl" means a monocyclic or fused ring containing one or more heteroatoms of N, O or S, typically, a 5-6 membered heterocyclyl containing one or more heteroatoms of N, O or S, such as piperazino, morpholino, piperidino, pyrrolidinyl and derivatives thereof.

The term "aryl" means an all-carbon monocyclic or fused ring having a fully conjugated π-electron system, typically having 6 to 14 carbon atoms, preferably having 6 to 12 carbon atoms, and most preferably having 6 carbon atoms. The aryl group may be unsubstituted or substituted by one or more substituents including, but not limited to, alkyl, alkoxyl, cyano, hydroxyl, carbonyl, carboxyl, aryl, aralkyl, amino, halogen, sulfonyl, sulfinyl, and phosphoryl. The examples of unsubstituted aryl groups include, but are not limited to, phenyl, naphthyl, and anthracenyl.

The term "heteroaryl" means a monocyclic or fused ring of 5 to 12 ring atoms, which contains 1 to 4 ring atoms selected from N, O, and S, the remaining ring atoms being C, and has a fully conjugated π-electron system, including but not limited to, pyrrolyl, furyl, thienyl, imidazolyl, oxazolyl, isoxazolyl, pyrazolyl, pyridyl, pyrimidinyl, pyrazinyl, pyridazinyl, quinolinyl, isoquinolyl, triazolyl, and tetrahydropyrrolyl. The heteroaryl may be unsubstituted or substituted, the substituents including but not limited to alkyl, alkoxyl, aryl, aralkyl, amino, halogen, hydroxyl, cyano, nitro, carbonyl and heteroalicyclic group.

The term "urea" means a group represented by formula —N($R_a R_b$)—C(=O)—N$R_c R_d$, wherein, $R_a$, $R_b$, $R_c$ and $R_d$ are independently selected from hydrogen, alkyl, cycloalkyl, heterocycle, aryl or heteroaryl, etc.

The term "covalent bond" means the interaction formed by share electron pairs.

"Treatment" means any treatment of a disease in a mammal, including: (1) preventing the disease, that is, preventing the progression the symptom of a clinical disease; (2) inhibiting the disease, that is, inhibiting the development of clinical symptoms; and (3) alleviating the disease, that is, causing remission of clinical symptoms.

The present invention further provides a pharmaceutical composition, comprising the compound as described above or a pharmaceutically acceptable salt thereof as an active ingredient, and one or more pharmaceutically acceptable carriers.

A "pharmaceutical composition", as used herein, means a formulation of one or more compounds of the present invention or salt thereof and a carrier generally accepted in the art for delivery of a biologically active compound to an organism (for example, a human). The purpose of the pharmaceutical composition is to facilitate delivery of the drug to the organism.

The term "pharmaceutically acceptable carrier" means a substance which is co-administered with the active ingredient and facilitates the administration of the active ingredient, including but not limited to any of acceptable glidants, sweeteners, diluents, preservatives, dyes/colorants, flavor enhancers, surfactants, wetting agents, dispersing agents, disintegrating agents, suspending agents, stabilizers, isotonic agents, solvents or emulsifiers used in human or animals (for example, livestock) approved by China Food and Drug Administration, for example, including but not limited to calcium carbonate, calcium phosphate, sugars and various types of starch, cellulose derivatives, gelatin, vegetable oils, and polyethylene glycols.

The pharmaceutical composition of the present invention can be formulated into solid, semi-solid, liquid or gaseous preparations, such as tablets, pills, capsules, powders, granules, ointments, emulsions, suspensions, solutions, suppositories, injections, inhalants, gels, microspheres and aerosols, etc.

The pharmaceutical composition of the present invention can be produced by a method that is well known in the art, such as a conventional mixing method, a dissolution method, a granulation method, a sugar coating pill method, a grinding method, an emulsification method, a freeze drying method, etc.

The route of administration of a compound or a pharmaceutically acceptable salt thereof or a pharmaceutical composition thereof in the present invention includes but not limited to oral, rectal, transmucosal, enteral, or topical, transdermal, inhalation, parenteral, sublingual, intravaginal, intranasal, intraocular, intraperitoneal, intramuscular, subcutaneous, or intravenous administration. Preferably, the route of administration is oral administration.

For oral administration, the pharmaceutical composition can be formulated by mixing the active compound with a pharmaceutically acceptable carrier which is well known in the art. With these carriers, the compounds can be formulated into tablets, pills, troches, dragees, capsules, liquids, gels, slurries, suspensions or the like for oral administration to a patient. For example, for a pharmaceutical composition for oral administration, a tablet can be obtained by the following way: combining the active ingredient with one or more solid carriers, granulating the resulting mixture if necessary, and adding a small amount of an excipient if necessary to from a mixture or granule, to form a tablet or a tablet core. The tablet core may be combined with an optional enteric coating material, and processed into a form of a coating formulation that is more advantageous for absorption by an organism such as a human.

The present invention further provides an application of the foregoing described compound, or a pharmaceutically acceptable salt thereof in preparing RORγt receptor inhibitors.

The present invention further provides use of a foregoing described compound, or a pharmaceutically acceptable salt thereof or their pharmaceutical compositions as RORγt receptor inhibitors in preparing drugs for treatment or prevention of RORγt-related diseases.

Preferably, the aforementioned RORγt inhibitor-related diseases are selected from multiple sclerosis, rheumatoid arthritis, collagen-induced arthritis, psoriasis, inflammatory bowel disease, encephalomyelitis, clonal diseases, asthma, cancer and other inflammation-related diseases. The cancer is preferably prostate cancer.

The present invention provides a class of biaryl urea compounds represented by general formula I. Studies have showed that, this class of compounds can effectively inhibit the RORγt protein receptor, thereby regulating the differentiation of Th17 cells and inhibiting the production of IL-17, and can be used as a drug for the treatment of RORγt-mediated inflammation-related diseases.

DETAILED DESCRIPTION OF THE PREFERRED EMBODIMENTS

The following embodiments further describe the technical solutions of the present invention, but the scope of protection of the present invention is not limited to these embodiments. Modifications or equivalents that do not depart from the inventive concept are intended to fall within the scope of protection of the present invention.

In the process for preparing the target compound provided in the present invention, the column chromatography adopts the silica gels (300-300 mesh) produced by Rushan Sun Desiccant Co., Ltd.; the thin layer chromatography adopts GF254 (0.25 mm); the nuclear magnetic resonance chromatography (NMR) adopts Varian-400 nuclear magnetic resonance apparatus; and the LC/MS adopts an Agilent Technologi ESI 6120 LC/MS apparatus.

In addition, all operations involving materials that are susceptible to oxidation or hydrolysis are carried out under the nitrogen protection. Unless otherwise stated, the starting materials used herein are commercially available materials that can be used directly without further purification.

Example 1: (1-(2,6-dichloro-2'-(trifluoromethoxy)-[1,1'-biphenyl]-4-yl)-3-(4-(ethylsulfonyl)benzyl)urea)

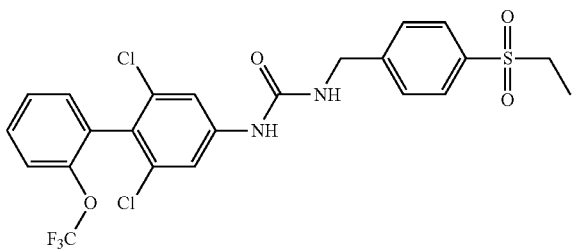

I-1

Synthesis of Intermediate 1: 2,6-dichloro-2'-(trifluoromethoxy)-[1,1'-biphenylyl]-4-amine Step 1: 2-bromo-1,3-dichloro-5-nitrobenzene 2,6-dichloro-4-nitroaniline (5 g, 24 mmol), copper bromide (16 g, 72 mmol) and acetonitrile (50 mL) were added to a single-mouth bottle, t-butyl nitrite (7.46 g, 72 mmol)

was added dropwise while stirring under ice bath, and then the obtained mixture was subjected to a reaction for 6 hours while stirring at a room temperature. After the reaction, the mixture was added with water (100 mL), extracted with ethyl acetate (100 mL×2), washed with saturated sodium chloride (100 mL), dried over anhydrous sodium sulfate, and concentrated at a reduced pressure to give 6.3 g orange solid, with a yield of 97%.

Step 2: 4-bromo-3,5-dichloroaniline

At room temperature, 2-bromo-1,3-dichloro-5-nitrobenzene (1 g, 4 mmol), ethanol (6 mL), tetrahydrofuran (1 mL), concentrated hydrochloric acid (1 mL), and stannous chloride (3.78 g, 16 mmol) were added to a single-mouth bottle, then heated to 50° C. and stirred for a reaction for 2 hours. After the reaction, the obtained mixture was cooled to room temperature, the solvent was dried with rotation under vacuum, and the mixture was added with 2N aqueous solution of sodium hydroxide, and extracted by ethyl acetate (100 mL×3). After that, the organic layers were combined, dried and concentrated under a reduced pressure to give the crude product (0.86 g), with a yield of 96.7%.

Step 3: 2,6-dichloro-2'-(trifluoromethoxy)-[1,1'-biphenylyl]-4-amine 4-bromo-3,5-dichloroaniline (200 mg, 0.83 mmol), (2-(trifluoromethoxy)benzyl)boronic acid (342 mg, 1.66 mmol), tri-tert-butylphosphine tetrafluoroborate (96 mg, 0.33 mmol), Pd$_2$dba$_3$ (304 mg, 0.33 mmol), saturated sodium carbonate (1.245 mL, 2.49 mmol), and 1,4-dioxane (4 mL) were added to a microwave tube, and reacted for 4 hours under microwave at 120° C. After reaction, the reaction mixture was concentrated in vacuo to remove the solvent, added with water, and extracted with ethyl acetate, and then the organic layers were combined, and the solvent was dried under a reduced pressure, and separated by a silica gel column (ethyl acetate:petroleum ether=0:100-10:90), to give the product (yellow solid, 136 mg), with a yield of 59.9%.

Synthesis of Intermediate 2: (4-(ethylsulfonyl)benzyl) methylamine

Step 1: 4-(ethylsulfonyl)benzonitrile 4-cyanobenzene-1-sulfonyl chloride (1 g, 4.97 mmol), water (15 mL), sodium bicarbonate (835 mg, 9.94 mmol), and sodium sulfite (689 mg, 5.47 mmol) were added to a 100 mL single-mouth bottle, and the reaction solution reacted for 4 hours while stirring at 70° C., and the solvent was spun under a reduced pressure. The crude product was re-dissolved with N,N-dimethylformamide (20 mL), ethyl iodide (1.2 mL) was added, and the reaction mixture was stirred at 70° C. for 4 hours. After the mixture was cooled to room temperature, water (30 mL) was added, and the obtained mixture was extracted with ethyl acetate (30 mL×3). The organic layers were combined, washed with saturated salt solution, dried over anhydrous sodium sulfate, and filtered. After that, the filtrate was concentrated in vacuo give a crude product, and the crude product was purified by a silica gel column (ethyl acetate:petroleum ether=1:4-1:2) to give the product (yellow solid, 630 mg), with a yield of 65.0%. $^1$H NMR (400 MHz, CDCl$_3$) δ 8.04 (d, J=8.5 Hz, 2H), 7.89 (d, J=8.6 Hz, 2H), 3.16 (q, J=7.4 Hz, 2H), 1.30 (t, J=7.4 Hz, 3H).

Step 2: (4-(ethylsulfonyl)benzyl) methylamine 4-(ethylsulfonyl)benzonitrile (630 mg, 3.23 mmol), methanol (10 mL), and Pd/C (100 mg, 10%) were added to a 25 mL single-mouth bottle. The reaction solution was stirred at room temperature for 1 hour under a hydrogen atmosphere, and then filtered over celite, and the solvent was dried with rotation under vacuum to give the product (white solid, 500 mg), with a yield of 77.9%. $^1$H NMR (400 MHz, CDCl$_3$) δ 7.86 (d, J=8.3 Hz, 2H), 7.53 (d, J=8.2 Hz, 2H), 3.99 (s, 2H), 3.10 (d, J=7.4 Hz, 2H), 1.27 (t, J=7.4 Hz, 3H).

Synthesis of Compound 1-(2,6-dichloro-2'-(trifluoromethoxy)-[1,1'-biphenyl]-4-yl)-3-(4-(ethylsulfonyl)benzyl)urea 2,6-dichloro-2'-(trifluoromethoxy)-[1,1'-biphenylyl]-4-amine (48 mg, 0.15 mmol), dichloromethane (2 mL), and DIEA (38.7 mg, 0.3 mmol) were added to a 25 mL single-mouth bottle, and stirred for 5 min under ice bath, and then triphosgene (13 mg, 0.05 mmol) was added, and the reaction was continued under ice bath for 30 min, and then (4-(ethylsulfonyl)benzyl)methylamine (30 mg, 0.15 mmol) was added, and the reaction was continued under ice bath for 30 min, then at room temperature overnight. The obtained mixture was added with H$_2$O (10 mL), and was extracted with dichloromethane (10 mL×3). The organic layers were combined, washed with saturated sodium chloride (10 mL), dried over anhydrous sodium sulfate, and filtered, and the filtrate was concentrated in vacuo obtain a crude product. The crude product was separated by preparative thin layer chromatography (dichloromethane:methanol=50:1) to give the product of 1-(2,6-dichloro-2'-(trifluoromethoxy)-[1,r-biphenyl]-4-yl)-3-(4-(ethylsulfonyl)benzyl) urea (white solid, 26 mg), with a yield of 31.7%. $^1$H NMR (400 MHz, CDCl$_3$) δ 7.67-7.65 (d, J=8.4 Hz, 2H), 7.56 (s, 2H), 7.54 (s, 1H), 7.49-7.43 (m, 1H), 7.39-7.34 (m, 4H), 7.26-7.22 (m, 1H), 6.08-6.05 (t, J 6.0 Hz, 1H), 4.51-4.50 (d, J 6.0 Hz, 2H), 3.18-3.13 (q, J 7.4 Hz, 2H), 1.31-1.27 (t, J=7.4 Hz, 3H). MS (ESI) m/z: 546.7 (MH+).

Example 2: (1-([1,1'-biphenyl]-4-yl)-3-(4-(ethylsulfonyl)benzyl)urea)

I-2

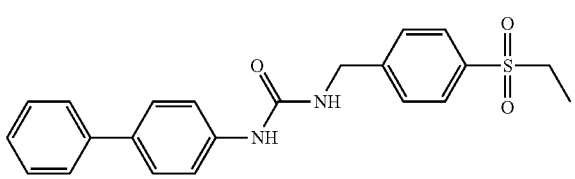

(4-(ethylsulfonyl)benzyl)methylamine (50 mg, 0.30 mmol), DCM (2 mL), and DIEA (77.4 mg, 0.6 mmol) were added to a 25 mL single-mouth bottle and stirred under ice bath condition for 5 min, and then triphosgene (26 mg, 0.10 mmol) was added, and the reaction was continued under ice bath for 30 min, and then 4-biphenylamine (60 mg, 0.30 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo obtain a crude product. The crude product was separated by preparative thin layer chromatography (petroleum ether:ethyl acetate=1:1) to give the product of 1-([1,1'-biphenyl]-4-yl)-3-(4-(ethylsulfonyl)benzyl)urea (white solid, 16 mg), with a yield of 22.8%. $^1$H NMR (400 MHz, DMSO) δ 7.83 (d, J=7.9 Hz, 2H), 7.64-7.51 (m, 7H), 7.48 (d, J=8.2 Hz, 2H), 7.41 (t, J=7.7 Hz, 2H), 7.28 (t, J=7.5 Hz, 1H), 6.81 (s, 1H), 4.40 (s, 2H), 3.24 (d, J=7.4 Hz, 2H), 1.06 (t, J=7.2 Hz, 3H). MS (ESI) m/z: 394.9 (MH+).

Example 3: (1-(2-chloro-2'-(trifluoromethoxy)-[1,1'-biphenyl]-4-yl)-3-(4-(ethylsulfonyl)benzyl)urea)

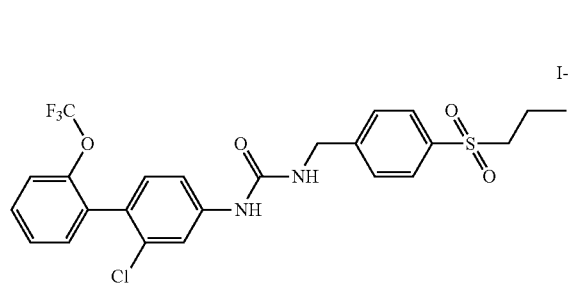

I-3

Step 1: 2-chloro-2'-(trifluoromethoxy)-[1,1'-biphenylyl]-4-amine 4-chloro-3-bromoaniline (500 mg, 2.43 mmol), 2-trifluoromethoxyphenylboronic acid (649 mg, 3.15 mmol), Pd$_2$(dppf)Cl$_2$ (69 mg, 0.12 mmol), potassium carbonate (1.01 g, 7.29 mmol), and acetonitrile/water (4 mL/1 mL) were added to a microwave tube, after being nitrogen sparged for 5 minutes, the mixture was stirred and heated to 100° C. for 2 hours under microwave, then the resulting mixture was washed with saturated ammonium chloride (20 mL), and separated through a silica gel column (eluent petroleumether:ethylacetate=10:1-5:1) to give the product of 2-chloro-2'-(trifluoromethoxy)-[1,1'-biphenylyl]-4-amine (yellow oil, 610 mg), with a yield of 88.5%. $^1$H NMR (400 MHz, CDCl$_3$) δ 7.42-7.35 (m, 1H), 7.36-7.28 (m, 3H), 7.06-7.04 (d, J=8.2 Hz, 1H), 6.81-6.80 (d, J=1.9 Hz, 1H), 6.64-6.62 (d, J=8.2 Hz, 1H), 3.57 (s, 2H). MS (ESII) m/z: 288.0 (MH+).

Step 2: 1-(2-chloro-2'-(trifluoromethoxy)-[1,1'-biphenyl]-4-yl)-3-(4-(ethylsulfonyl)benzyl) urea 2-chloro-2'-(trifluoromethoxy)-[1,1'-biphenylyl]-4-amine (50 mg, 0.17 mmol), dichloroethane (2 mL), and DIEA (45 mg, 0.35 mmol) were added to a 25 mL three-necked bottle, and stirred under ice bath for 5 min, and then triphosgene (18.6 mg, 0.06 mmol) was added, and the reaction was continued under ice bath for 30 min. Then (4-(ethylsulfonyl)benzyl)methylamine (37.8 mg, 19 mmol) was added, and the reaction was continued under ice bath for 30 min, then at room temperature overnight. After the reaction, H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo obtain a crude product. The crude product was separated by preparative thin layer chromatography (dichloromethane:methanol=20:1) to give the product of 1-(2-chloro-2'-(trifluoromethoxy)-[1,1'-biphenylyl]-4-yl)-3-(4) (ethylthiosulfonyl)phenyl)urea (white solid, 15 mg), with a yield of 16.8%. $^1$H NMR (400 MHz, CD$_3$OD) δ 7.90-7.88 (d, J=8.3 Hz, 2H), 7.72 (d, J=2.0 Hz, 1H), 7.62-7.60 (d, J=8.1 Hz, 2H), 7.53-7.43 (m, 1H), 7.44-7.36 (m, 2H), 7.37-7.29 (m, 2H), 7.19-7.17 (d, J=8.4 Hz, 1H), 4.53 (s, 2H), 3.21-3.17 (q, J=7.4 Hz, 2H), 1.23-1.19 (t, J=7.4 Hz, 3H). MS (ESI) m/z: 513.1 (MH+).

Example 4: (1-(2,6-dichloro-2'-(trifluoromethoxy)-[1,1'-biphenyl]-4-yl)-3-(4-(methylsulfonyl)benzyl)urea)

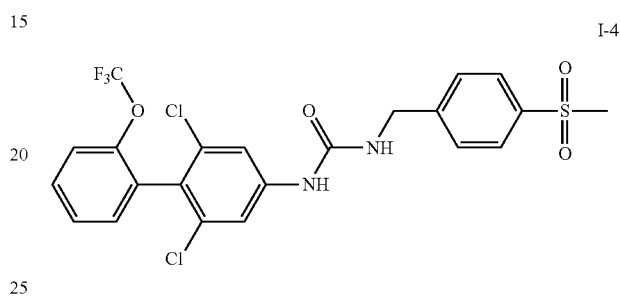

I-4

2,6-dichloro-2'-(trifluoromethoxy)-[1,1'-biphenylyl]-4-amine (87 mg, 0.27 mmol), DCM (3 mL), and DIEA (104 mg, 0.81 mmol) were added to 25 mL single-mouth bottle and stirred under ice bath for 5 min, and then triphosgene (27 mg, 0.09 mmol) was added, and the reaction was continued under ice bath for 30 min, then (4-(methylsulfonyl)benzyl)methylamine (59 mg, 0.27 mmol) was added, and the ice bath is continued for 30 min, then leaving the reaction overnight at room temperature. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (dichloromethane:methanol=50:1) to give the product of 1-(2,6-dichloro-2'-(trifluoromethoxy)-[1,1'-biphenyl]-4-yl)-3-(4-(methylsulfonyl)benzyl)urea (white solid, 5 mg), with a yield of 3.47%. $^1$H NMR (400 MHz, CDCl$_3$) δ 7.73-7.71 (d, J=8.2 Hz, 2H), 7.54 (s, 2H), 7.51-7.42 (m, 2H), 7.41-7.33 (m, 4H), 7.27-7.23 (m, 2H), 6.02-5.99 (t, J=6.1 Hz, 1H), 4.49-4.48 (d, J=5.7 Hz, 2H), 3.09 (s, 3H). MS (ESI) m/z: 531.0 (M−1).

Example 5: (4-((3-(2,6-dichloro-2'-(trifluoromethoxy)-[1,1'-biphenyl]-4-yl)ureido)methyl)-N-methylbenzenesulfonamide)

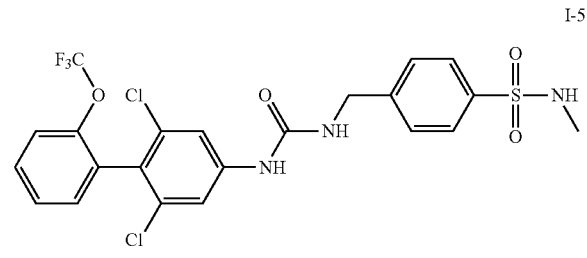 [SMILES: CNS(=O)(=O)c1ccc(CNC(=O)Nc2cc(Cl)c(-c3ccccc3OC(F)(F)F)c(Cl)c2)cc1]

I-5

2,6-dichloro-2'-(trifluoromethoxy)-[1,1'-biphenylyl]-4-amine (97 mg, 0.3 mmol), DCM (10 mL), and DIEA (77 mg, 0.6 mmol) were added to a 50 mL single-mouth bottle and stirred under ice bath for 5 min, then triphosgene (35 mg, 0.12 mmol) was added, and the reaction was continued under ice bath for 30 min, and then 4-(aminomethyl)-N-methylbenzenesulfonamide (72 mg, 0.36 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (20 mL), dried over anhydrous sodium sulfate, and filtered, and the filtrate was concentrated in vacuo to obtain a crude product. The crude product was separated by a silica gel column (petroleumether:ethylacetate=100:1-20:1) to give the product of 4-((3-(2,6-dichloro-2'-(trifluoromethyl)-[1,1'-biphenyl]-4-yl)ureido)methyl)-N-methyl benzenesulfonamide (white solid, 130 mg), with a yield of 79.3%. $^1$H NMR (400 MHz, DMSO) δ 9.20 (s, 1H), 7.74-7.72 (d, J=8.2 Hz, 2H), 7.66 (s, (H, 2H), 7.44-7.32-4.38 (d, J=5.7 Hz, 2H), 2.38-2.37 (d, J=4.8 Hz, 3H). MS (ESI) m/z: 547.8 (M+1).

Example 6: (4-((3-(2,6-dichloro-2'-(trifluoromethoxy)-[1'-biphenyl]1,1'-biphenyl-4-yl)ureido)methyl)benzene sulfonamide)

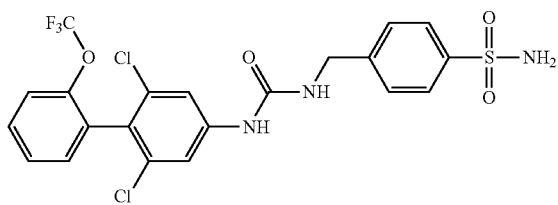

I-6

Step 1: 4-cyanobenzenesulfamide

Aqueous ammonia (13 mL, 194 mmol, 28%) was added to a 50 mL single-mouth bottle, 4-cyanobenzenesulfonyl chloride (4 g, 19.4 mmol) was dissolved in tetrahydrofuran (5 mL) and added dropwise to the reaction solution in the bottle to perform reaction for 2 hours at room temperature. Water (20 mL) was added, and the mixture was extracted with ethyl acetate (20 mL×3). The organic layers were combined, dried over anhydrous sodium sulfate, and the solvent was dried with rotation under vacuum to give the product of 4-cyanobenzenesulfamide (white solid, 3.4 g), with a yield of 94%. $^1$H NMR (400 MHz, DMSO) δ 8.06 (d, J=8.5 Hz, 2H), 7.96 (d, J=8.6 Hz, 2H), 7.65 (s, 2H). MS (ESI) m/z: 180.9 (M+1).

Step 2: 4-(aminomethyl)benzenesulfonamide 4-cyanobenzenesulfamide (500 mg, 2.74 mmol), methanol (3 mL), tetrahydrofuran (1 mL), aqueous ammonia (0.5 mL) and Raney Ni (100 mg) were added to a 20 mL single-mouth bottle, and the mixture reacted at room temperature for 30 min under the hydrogen atmosphere, filtered and concentrated in vacuo to give the product of 4-(aminomethyl)benzenesulfonamide (white solid, 420 mg), with a yield of 82.2%. $^1$H NMR (400 MHz, DMSO) δ 7.74 (d, J=8.0 Hz, 2H), 7.50 (d, J=7.9 Hz, 2H), 7.29 (s, 2H), 3.77 (s, 2H). MS (ESI m/z: 187.0 (M−1).

Step 3: 4-((3-(2,6-dichloro-2'-(trifluoromethoxy)-[1,1'-biphenyl]-4-yl)ureido) methyl)benzenesulfonamide 2,6-dichloro-2'-(trifluoromethoxy)-[1,1'-biphenylyl]-4-amine (177 mg, 0.55 mmol), DCM (4 mL), and DIEA (212 mg, 1.65 mmol) were added to a 25 mL single-mouth bottle, and stirred under ice bath for 5 min, and then triphosgene (58.8 mg, 0.20 mmol) was added, and the reaction was continued under ice bath for 30 min, then 4-(aminomethyl)benzenesulfonamide (110 mg, 0.6 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleumether:ethylacetate=4:1) to give the product (white solid, 150 mg), with a yield of 47.6%. $^1$H NMR (400 MHz, CD$_3$OD) δ 7.86 (d, J=8.3 Hz, 2H), 7.58 (s, 2H), 7.53-7.47 (m, 3H), 7.43-7.36 (m, 2H), 7.28 (d, J=7.5 Hz, 1H), 4.47 (s, 2H). MS (ESI) m/z: 531.7 (M−1).

Example 7: (N-((4-((3-(2,6-dichloro-2'-(trifluoromethoxy)-[1,1'-biphen-1,1'-biphenyl]-4-yl)ureido) methyl)phenyl)sulfonyl)acetamide)

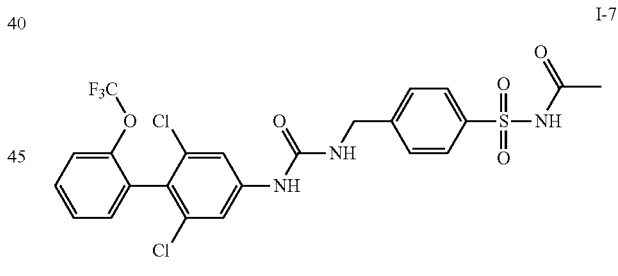

I-7

4-((3,6-dichloro-2'-(trifluoromethoxy)-[1,1'-biphenyl]-4-yl)ureido)methyl)benzenesulfonamide (77 mg, 0.14 mmol), methylene chloride (5 mL), acetic anhydride (17.5 mg, 0.17 mmol), and triethylamine (17.3 mg, 0.17 mmol) were added to a 25 mL single-mouth bottle to react for 2 hours at room temperature while stirring, then methylene chloride (10 mL) was added, and the mixture was washed with saturated ammonium chloride (10 mL). The organic layer was concentrated in vacuo to obtain a crude product. The crude product was separated by preparative thin layer chromatography (petroleumether:ethylacetate=2:1) to give the product (white solid, 52 mg), with a yield of 62.6%. $^1$H NMR (400 MHz, CD$_3$OD) δ 7.97 (d, J=8.3 Hz, 2H), 7.59 (s, 2H), 7.54 (d, J=8.2 Hz, 2H), 7.51 (d, J=8.1 Hz, 1H), 7.45-7.41 (m, 1H), 7.40-7.36 (m, 1H), 7.29 (d, J=6.3 Hz, 1H), 4.49 (s, 2H), 1.94 (s, 3H). MS (ESI) m/z: 573.5 (M−1).

Example 8: (N-(4-((3-(2,6-dichloro-2'-(trifluoromethoxy)-[1,1'-biphenyl]-4-yl)ureido)methyl)phenyl)methane sulfonamide)

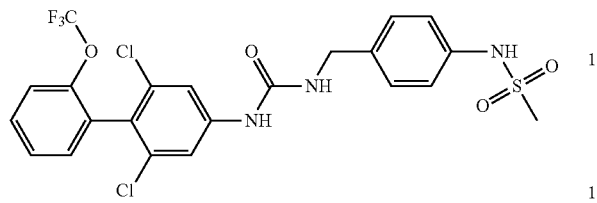

I-8

Step 1: N-(4-cyanobenzyl) methane sulfonamide p-cyanoaniline (2 g, 16.9 mmol), pyridine (2.67 g, 33.8 mmol) and dichloromethane (10 mL) were added to a 25 mL single-mouth bottle, and methanesulfonyl chloride (2.12 g, 18.6 mmol) was added dropwise while stirring to continue stirring 2 hours at room temperature. Water (50 mL) was added, and the obtained mixture was extracted with ethyl acetate (50 mL×3), and washed with saturated sodium chloride. The organic layer was dried over anhydrous sodium sulfate, and filtered, and the filtrate was concentrated in vacuo to give the product (white solid, 2.5 g), with a yield of 78.1%. $^1$H NMR (400 MHz, DMSO) δ 10.50 (s, 1H), 7.76 (d, J=8.6 Hz, 2H), 7.30 (d, J=8.6 Hz, 2H), 3.11 (s, 3H).

Step 2: N-(4-(aminomethyl)benzyl)methane sulfonamide

N-(4-cyanobenzyl) methane sulfonamide (100 mg, 0.51 mmol), methanol (10 mL), aqueous ammonia (0.5 mL, 28%) and Raney Ni (100 mg) were added to a 25 mL single-mouth bottle to react for 30 minutes at room temperature while stirring, and the obtained mixture was filtered through celite and concentrated in vacuo to give the product (white solid, 95 mg), with a yield of 93.1%. $^1$H NMR (400 MHz, DMSO) δ 7.25 (s, 2H), 7.12 (d, J=7.9 Hz, 2H), 3.14 (s, 2H), 2.89 (s, 3H). MS (ESI) m/z: 198.9 (M−1).

Step 3: N-(4-((3-(2,6-dichloro-2'-(trifluoromethoxy)-[1,1'-biphenyl]-4-yl)ureido)methyl)benzyl)methane sulfonamide 2,6-dichloro-2'-(trifluoromethoxy)-[1,1'-biphenylyl]-4-amine (100 mg, 0.31 mmol), DCM (4 mL), and DIEA (120 mg, 0.93 mmol) were added to a 25 mL single-mouth bottle, stirred for 10 min under ice bath, and then triphosgene (35 mg, 0.11 mmol) was added, and the reaction was continued under ice bath for 30 min, and then N-(4-(aminomethyl)benzyl)methane sulfonamide (74 mg, 0.37 mmol) was added, and the reaction was continued under ice bath for 30 min, then at room temperature overnight. H₂O (10 mL) was added, and the obtained mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (dichloromethane:methanol=20:1) to give the product (white solid, 120 mg), with a yield of 70.0%. $^1$H NMR (400 MHz, CD₃OD) δ 7.56 (s, 2H), 7.49 (t, J=28 Hz, 1H), 7.44-7.35 (m, 2H), 7.35-7.25 (m, 3H), 7.25-7.16 (m, 2H), 4.34 (s, 2H), 2.90 (s, 3H). MS (ESI) m/z: 545.7 (M−1).

Example 9: (1-(2,6-dichloro-2'-(trifluoromethoxy)-[1,1'-biphenyl]-4-yl)-3-(4-(ethylsulfonimidoyl)benzyl)urea)

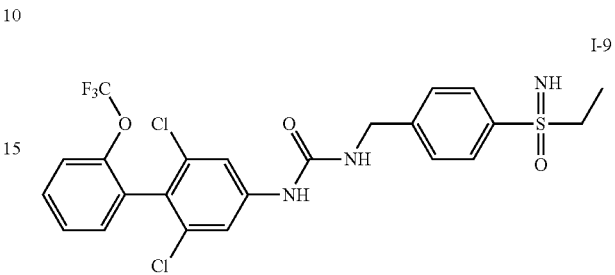

I-9

Step 1: (4-(ethylsulfinyl)benzyl)methylamine 4-(ethylsulfinyl)benzonitrile (228 mg, 1.37 mmol), methanol (10 mL), aqueous ammonia (0.5 mL, 28%) and Raney Ni (100 mg) were added to a 25 mL single-mouth bottle. The reaction mixture was stirred at room temperature for 1 hour, and filtered through celite, and the solvent was dried with rotation under vacuum to give the product (white solid, 200 mg), with a yield of 98.3%. MS (ESI) m/z: 184.1 (MH+).

Step 2: 1-(2,6-dichloro-2'-(trifluoromethoxy)-[1,1'-biphenyl]-4-yl)-3-(4-(ethylsulfinyl)benzyl) urea 2,6-dichloro-2'-(trifluoromethoxy)-[1,1'-biphenylyl]-4-amine (200 mg, 0.62 mmol), dichloromethane/N,N-dimethylformamide (4 mL/2 mL) and DIEA (239 mg, 1.86 mmol) were added to a 25 mL single-mouth bottle, stirred for 10 min under ice bath, and then triphosgene (65 mg, 0.22 mmol) was added, and the reaction was continued under ice bath for 30 minutes, and then (4-(ethylsulfinyl)benzyl)methanamine (136 mg, 0.74 mmol) was added, and the reaction was continued under ice bath for 30 min, then at room temperature overnight. H₂O (10 mL) was added, and the obtained mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleum ether:ethyl acetate=1:2-1:1) to give the product (white solid, 137 mg), with a yield of 41.6%. $^1$H NMR (400 MHz, CDCl₃) δ 8.51 (s, 1H), 7.59 (s, 2H), 7.50-7.43 (m, 1H), 7.44-7.30 (m, 6H), 7.27 (s, 1H), 4.49 (s, 2H), 3.01-2.86 (m, 2H), 1.23 (t, J=7.4 Hz, 3H). MS (ESI) m/z: 530.7 (MH+).

Step 3: 1-(2,6-dichloro-2'-(trifluoromethoxy)-[1,1'-biphenyl]-4-yl)-3-(4-(ethylsulfonimido)benzyl) urea 1-(2,6-dichloro-2'-(trifluoromethoxy)-[1,1'-biphenyl]-4-yl)-3-(4-(ethylsulfinyl)benzyl) urea (140 mg, 0.25 mmol), trifluoroacetamide (58 mg, 0.52 mmol), magnesium oxide (42 mg, 1.04 mmol), rhodium acetate (2.8 mg, 2.5 mol %), iodobenzene tetraacetate (128 mg, 0.4 mmol), and dichloromethane (10 mL) were added to a 25 mL single-mouth bottle, and reacted at room temperature overnight. And the mixture was concentrated in vacuo to remove the solvent, then added with methanol (1 mL) and potassium carbonate (179 mg, 1.3 mmol), and stirred for 2 hours continuously at room temperature. After the solvent was removed by concentration in vacuo, the crude product was separated by a silica gel column (dichloromethane:methanol=50:1), to give the product (white solid, 70 mg), with a yield of 50.4%. ¹H NMR (400 MHz, CDCl₃) δ 8.36 (s, 1H), 7.75 (d, J=6.9 Hz, 2H), 7.55 (s, 2H), 7.45 (t, J=7.1 Hz, 1H), 7.39-7.28 (m, 4H), 7.22 (d, J=6.7 Hz, 1H), 6.68 (s, 1H), 4.44 (d, J=4.4 Hz, 2H), 3.20 (s, 2H), 2.77 (s, 1H), 1.25 (d, J=7.5 Hz, 3H). MS (ESI) m/z: 545.7 (MH+).

Example 10: 4-((3-(2,6-dichloro-2'-(trifluoromethoxy)-[1,1'-biphenyl]-4-yl)ureido)methyl)-N-(methylsulfonyl)benzamide

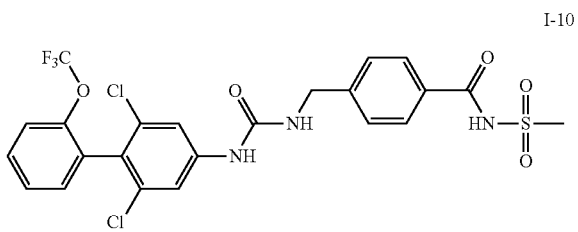 [SMILES: CS(=O)(=O)NC(=O)c1ccc(CNC(=O)Nc2cc(Cl)c(-c3ccccc3OC(F)(F)F)c(Cl)c2)cc1]

I-10

Step 1: 4-cyano-N-(methylsulfonyl)benzamide p-cyanobenzoic acid (1 g, 6.8 mmol), thionyl chloride (0.5 mL), and N,N-dimethylformamide (2 drops) were added to a 25 mL single-mouth bottle, and heated to react for 2 hours at 70° C., and thionyl chloride was concentrated under a reduced pressure. The crude product was dissolved in dichloromethane (20 mL), triethylamine (2.06 g, 20 mmol), methane sulfonamide (770 mg, 8.2 mmol) were added, and the mixture was stirred at room temperature overnight. Then H₂O (20 mL) was added, and the obtained mixture washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by a silica gel column (dichloromethane:methanol=20:1) to give the product (yellow solid, 400 mg), with a yield of 26.3%. ¹H NMR (400 MHz, DMSO) δ 8.04 (d, J=8.3 Hz, 2H), 7.88 (d, J=8.3 Hz, 2H), 3.10 (s, 3H). MS (ESI) m/z: 222.9 (M−1).

Step 2: 4-(aminomethyl)-N-(methylsulfonyl)benzamide 4-cyano-N-(methylsulfonyl)benzamide (400 mg, 1.79 mmol), methanol (2 mL), aqueous ammonia (0.5 mL, 28%) and Raney Ni (100 mg) were added to a 25 mL single-mouth bottle. The reaction mixture was stirred at room temperature for 30 minutes under hydrogen atmosphere at an atmospheric pressure, then filtered through celite, and the solvent was dried with rotation under vacuum to give the product (white solid, 360 mg), with a yield of 78.7%. MS (ESI) m/z: 226.9 (M−1).

Step 3: (4-((3-(2,6-dichloro-2'-(trifluoromethoxy)-[1,1'-biphenyl]-4-yl)ureido)methyl)-N-(methylsulfonyl)benzamide 2,6-dichloro-2'-(trifluoromethoxy)-[1,1'-biphenylyl]-4-amine (100 mg, 0.31 mmol), DCM (4 mL), and DIEA (120 mg, 0.93 mmol) were added to a 25 mL single-mouth bottle, and stirred for 10 min under ice bath, and then triphosgene (35 mg, 0.11 mmol) was added, and the reaction was continued under ice bath for 30 minutes, and then 4-(aminomethyl)-N-(methylsulfonyl)benzamide (74 mg, 0.37 mmol) was added, and the reaction was continued under ice bath for 30 min, then at room temperature overnight. H₂O (10 mL) was added, and the obtained mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (dichloromethane:methanol=20:1) to give the product (white solid, 70 mg), with a yield of 39.1%. ¹H NMR (400 MHz, CD₃OD) δ 7.88 (d, J=8.2 Hz, 2H), 7.59 (s, 2H), 7.55-7.49 (m, 1H), 7.49-7.45 (m, 2H), 7.45-7.36 (m, 2H), 7.29 (dd, J=7.6, 1.5 Hz, 1H), 4.48 (s, 2H), 3.34 (d, J=1.7 Hz, 3H). MS (ESI) m/z: 575.6 (MH+).

Example 11: (1-(2,6-dichloro-2'-(trifluoromethoxy)-[1,1'-biphenyl]-4-yl)-3-((5-(ethylsulfonyl) pyridine-2-yl)methyl)urea

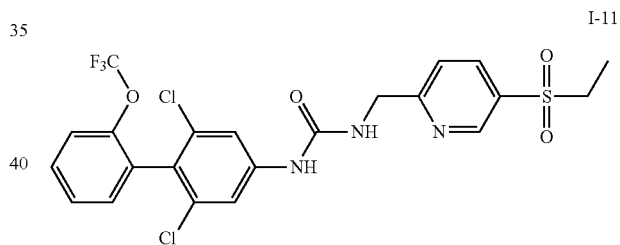

I-11

Step 1: 5-(ethylthio) pyridinecarbonitrile 5-bromo-2-pyridinecarbonitrile (940 mg, 5.14 mmol), ethanethiol (505 mg, 6.01 mmol), potassium carbonate (981 mg, 7.11 mmol), and NMP (10 mL) were added to a 50 mL single-mouth bottle. The obtained mixture reacted at room temperature while stirring overnight. Water (20 mL) was added, and the mixture was extracted with ethyl acetate (30 mL×3). The organic layer was concentrated in vacuo to give the product of 5-(ethylthio) pyridinecarbonitrile (900 mg), with a yield of 100%. MS (ESI) m/z: 165.1 (MH+).

Step 2: 5-(ethylsulfonyl)-2-pyridinecarbonitrile 5-(ethylthio) pyridinecarbonitrile (800 mg, 4.88 mmol) and dichloromethane (20 mL) were added to a 25 mL single-mouth bottle, and stirred for 10 min under ice bath, and mCPBA (1.84 g, 10.7 mmol) was added to the reaction mixture in portions, leaving the reaction at room temperature overnight. The reaction mixture was washed with 2N sodium carbonate solution, and the organic layer was concentrated in vacuo and passed through a silica gel column (petroleumether:ethylacetate=2:1-1:1) to give the product (900 mg), with a yield of 90.0%. $^1$H NMR (400 MHz, CDCl$_3$) δ 9.18 (d, J=1.2 Hz, 1H), 8.37 (dd, J=8.0, 1.8 Hz, 1H), 7.93 (d, J=8.0 Hz, 1H), 3.21 (q, J=7.4 Hz, 2H), 1.34 (t, J=7.4 Hz, 3H). MS (ESI) m/z: 197.1 (MH+).

Step 3: (5-(ethylsulfonyl)-pyridine-2-yl)methylamine 5-(ethylsulfonyl) 2-pyridinecarbonitrile (200 mg, 1 mmol), methanol (10 mL) and Pd/C (100 mg, 10%) were added to a 25 mL single-mouth bottle. The reaction mixture was stirred at room temperature for 30 min, and filtered through celite, and the solvent was dried with rotation under vacuum to give the product (white solid, 110 mg), with a yield of 53.9%. MS (ESI) m/z: 201.1 (MH+).

Step 4: 1-(2,6-dichloro-2'-(trifluoromethoxy)-[1,1'-biphenyl]-4-yl)-3-(5-(ethylsulfonyl)-2-pyridyl) urea 2,6-dichloro-2'-(trifluoromethoxy)-[1,1'-biphenylyl]-4-amine (100 mg, 0.31 mmol), DCM (4 mL), and DIEA (120 mg, 0.93 mmol) were added to a 25 mL single-mouth bottle, and stirred for 10 min under ice bath. Then triphosgene (35 mg, 0.11 mmol) was added, and the reaction was continued under ice bath for 30 min, and then (5-(ethylsulfonyl)pyridine-2-yl)methylamine (74 mg, 0.37 mmol) was added, and the reaction was continued under ice bath for 30 min, then at room temperature overnight. H$_2$O (10 mL) was added, and the obtained mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated with preparative thin layer chromatography (dichloromethane:methanol=20:1) to give the product (white solid, 70 mg), with a yield of 39.1%. $^1$H NMR (400 MHz, CD$_3$OD) δ 8.98 (d, J=2.0 Hz, 1H), 8.27 (dd, J=8.3, 2.3 Hz, 1H), 7.67 (d, J=8.3 Hz, 1H), 7.60 (s, 2H), 7.56-7.47 (m, 1H), 7.46-7.36 (m, 2H), 7.29 (dd, J=7.6, 1.5 Hz, 1H), 4.64 (s, 2H), 3.28 (dd, J=14.7, 7.3 Hz, 2H), 1.24 (dd, J 10.0, 4.8 Hz, 3H). MS (ESI) m/z: 547.7 (MH+).

Example 12: (1-(2,6-dichloro-2'-(trifluoromethoxy)-[1,1'-biphenyl]-4-yl)-3-((5-(methylsulfonyl) pyridine-2-yl)methyl)urea

I-12

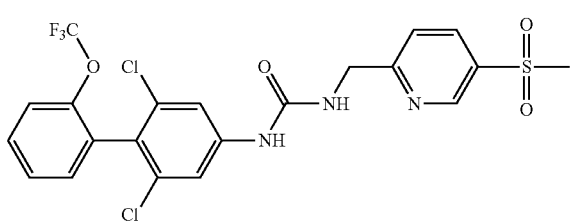

Step 1: 5-ethylsulfonyl-2-pyridinecarbonitrile 6-cyanopyridine-3-sulfonyl chloride (1 g, 4.9 mmol), water (15 mL), sodium bicarbonate (823 mg, 9.8 mmol) and sodium sulfite (679 mg, 5.39 mmol) were added to a 50 mL single-mouth bottle. The reaction mixture was stirred at 70° C. for subjecting to a reaction overnight, and the solvent was dried with rotation under a reduced pressure. The crude product was dissolved again with N,N-dimethylformamide (20 mL), then methyl iodide (2.08 g, 14.7 mmol) was added, and the reaction mixture was stirred at 70° C. for 4 hours. After being cooled to room temperature, the reaction mixture was added with water (30 mL), and extracted with ethyl acetate (30 mL×3). The organic layers were combined, washed with water for five times, washed once with saturated sodium chloride, dried over anhydrous sodium sulfate, and filtered, and the filtrate was concentrated under a reduced pressure to obtain a crude product. The crude product was separated by a silica gel column (ethyl acetate:petroleum ether=1.4-1.2), to give the product (white solid, 450 mg), with a yield of 50.2%. $^1$H NMR (400 MHz, CDCl$_3$) δ 9.24 (d, J=1.5 Hz, 1H), 8.41 (dd, J=8.1, 2.2 Hz, 1H), 7.93 (dd, J=8.1, 0.6 Hz, 1H), 3.17 (s, 3H). MS (ESI) m/z: 183.1 (MH+).

Step 2: 5-(methylsulfonyl) 2-pyridinemethylamine 5-ethylsulfonyl-2-pyridinecarbonitrile (350 mg, 1.92 mmol), methanol (2 mL), concentrated hydrochloric acid (5 drops) and Pd/C (35 mg) were added to a 25 mL single-mouth bottle. The reaction mixture was stirred at room temperature for 30 minutes while introducing hydrogen gas, and filtered over celite, and the solvent was dried with rotation under vacuum to give the product (266 mg), with a yield of 74.5%. MS (ESI) m/z: 187.1 (MH+).

Step 3: 1-(2,6-dichloro-2'-(trifluoromethoxy)-[1,1'-biphenyl]-4-yl)-3-(5-(methylsulfonyl)-2-pyridyl) urea 2,6-dichloro-2'-(trifluoromethoxy)-[1,1'-biphenylyl]-4-amine (100 mg, 0.31 mmol), dichloromethane (4 mL), and N,N-diisopropylethylamine (120 mg, 0.93 mmol) were added to a 25 mL single-mouth bottle under an condition of nitrogen protection, and stirred for 5 min under ice bath, and then triphosgene (35 mg, 0.11 mmol) was added, and the reaction was continued under ice bath for 10 minutes, and then 5-(methylsulfonyl) 2-pyridylmethylamine (63 mg, 0.34 mmol) was added, and the reaction was continued under ice bath for 30 min. H$_2$O (10 mL) was added, and the obtained mixture was washed with saturated ammonium chloride, extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated with preparative thin layer chromatography (dichloromethane:methanol=30:1) to give the product (white solid, 94 mg), with a yield of 56.3%. $^1$H NMR (400 MHz, CD$_3$OD) δ 9.03 (d, J 1.6 Hz, 1H), 8.30 (dd, J=8.3, 2.3 Hz, 1H), 7.66 (d, J=8.3 Hz, 1H), 7.60 (s, 2H), 7.55-7.47 (m, 1H), 7.45-7.35 (m, 2H), 7.28 (dd, J=7.6, 1.4 Hz, 1H), 4.63 (s, 2H), 3.19 (s, 3H). MS (ESI) m/z: 533.8 (MH+).

Example 13: (6-((3-(2,6-dichloro-2'-(trifluoromethoxy)-[1,1'-biphenyl]-4-yl)ureido)methyl)-N-methylpyridine-3-sulfonamide

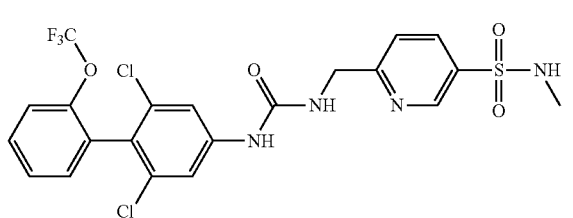

I-13

Step 1: 6-cyanopyridine-3-sulfonyl chloride

Water (90 mL) was added to a 500 mL single-mouth bottle A and stirred for 10 min under ice bath, then thionyl chloride (17 mL) was added dropwise slowly, after the addition, the obtained is subjected to a reaction for 8 hours at room temperature, and then cuprous chloride (66 mg, 0.67 mmol) was added, then subjecting to an ice bath.

5-aminopyridine carbonitrile (4.99 g, 41.9 mmol) and concentrated hydrochloric acid (50 mL) were added to another 500 mL single-mouth bottle B, stirred to be cooled under ice bath for 10 minutes, and then the aqueous solution (25 mL) of sodium nitrite (4.11 g, 59.6 mmol) was added dropwise, after the addition, the obtained mixture is subjected to a reaction under ice bath for 20 minutes.

The reaction mixture in the single-mouth bottle B were added to the single-mouth bottle A under ice bath, after the addition, the obtained mixture was subjected to a reaction for another 1 hour under ice bath, and a large amount of brown solid was precipitated, which was subjected to filtration, washed with water (125 mL×3), and dried under a vacuum condition to give the product (brown solid, 3.7 g), with a yield of 43.5%. MS (ESI) m/z: 202.9 (MH+).

Step 2: 6-cyano-N-methylpyridine-3-sulfonamide 6-cyanopyridine-3-sulfonyl chloride (1 g, 4.9 mmol), tetrahydrofuran (10 mL), and methylamine in ethanol (5.35 g, 49 mmol) were added to a 25 mL single-mouth bottle, and reacted at a room temperature for 10 minutes, and the obtained mixture was concentrated in vacuo to remove the solvent, and was separated by a silica gel column to give the product (550 mg), with a yield of 57.8%. $^1$H NMR (400 MHz, CDCl$_3$) δ 9.15 (s, 1H), (dd, J=8.1, 2.1 Hz, 1H), 7.88 (d, J=8.1 Hz, 1H), 4.72 (s, 1H), 2.78 (d, J=5.2 Hz, 3H). MS (ESI) m/z: 198.1 (MH+).

Step 3: 6-(aminomethyl)-N-methylpyridine-3-sulfonamide 6-cyano-N-methylpyridine-3-sulfonamide (250 mg, 1.27 mmol), methanol (4 mL), concentrated hydrochloric acid (5 drops) and Pd/C (25 mg, 60% in oil) were added to a 25 mL single-mouth bottle. The reaction mixture was stirred for 30 min at room temperature, filtered over celite, and then the solvent was dried with rotation under vacuum, and the product was used in the next step directly. MS (ESI) m/z: 202.1 (MH+).

Step 4: 6-((3-(2,6-dichloro-2'-(trifluoromethyl)-[1,1'-biphenyl]-4-yl)ureido)methyl)-N-methyl pyridine-3-sulfonamide 2,6-dichloro-2'-(trifluoromethoxy)-[1,1'-biphenylyl]-4-amine (100 mg, 0.31 mmol), dichloromethane (4 mL) and N,N-diisopropylethylamine (120 mg, 0.93 mmol) were added to a 25 mL single-mouth bottle, and stirred under ice bath for 5 minutes with the nitrogen protection, and then triphosgene (35 mg, 0.11 mmol) was added, and the reaction was continued under ice bath for 10 min, and then 6-(aminomethyl)-N-methylpyridine-3-sulfonamide (74 mg, 0.37 mmol) was added, and the reaction was continued under ice bath for 30 min. H$_2$O (10 mL) was added, and the obtained mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by a silica gel column (petroleumether:ethylacetate=1:2) to give the product (white solid, 41 mg), with a yield of 29.4%. $^1$H NMR (400 MHz, CD$_3$OD) δ 8.91 (d, J=1.8 Hz, 1H), 8.18 (dd, J=8.3, 2.2 Hz, 1H), 7.61 (d, J=9.9 Hz, 3H), 7.51 (td, J=8.1, 1.6 Hz, 1H), 7.44-7.37 (m, 2H), 7.29 (dd, J=7.6, 1.4 Hz, 1H), 4.61 (s, 2H), 2.55 (d, J=4.9 Hz, 3H). MS (ESI) m/z: 548.8 (MH+).

Example 14: 4-((3-(2,6-dichloro-2'-(trifluoromethoxy)-[1,1'-biphenyl]-4-yl)ureido)methyl)benzoic acid

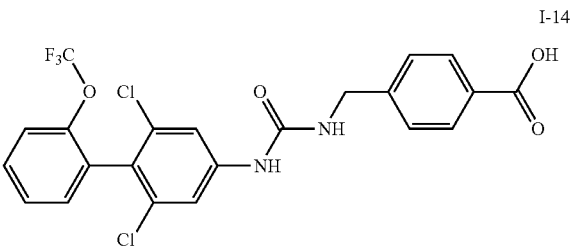 [SMILES: O=C(NCc1ccc(C(=O)O)cc1)Nc1cc(Cl)c(-c2ccccc2OC(F)(F)F)c(Cl)c1]

I-14

Step 1: 4-((3-(2,6-dichloro-2'-(trifluoromethoxy)-[1,1'-biphenyl]-4-yl)ureido)methyl)methyl benzoate 2,6-dichloro-2'-(trifluoromethoxy)-[1,1'-biphenylyl]-4-amine (100 mg, 0.31 mmol), DCM (5 mL) and DIEA (120 mg, 0.93 mmol) were added to a 25 mL single-mouth bottle, and stirred for 5 min under ice bath, and then triphosgene (33 mg, 0.11 mmol) was added, and the reaction was continued under ice bath for 30 min, and then 4-methyl aminomethylbenzoate (56 mg, 0.34 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleumether:ethylacetate=10:1) to give the product (white solid, 80 mg), with a yield of 50.3%. $^1$NMR (400 MHz, CDCl$_3$) δ 7.86 (d, J=8.1 Hz, 2H), 7.82 (s, 1H), 7.49-7.41 (m, 1H), 7.39 (s, 2H), 7.36-7.30 (m, 2H), 7.22 (d, J=8.1 Hz, 2H), 7.17 (d, J 7.6 Hz, 1H), 6.06 (s, 1H), 4.36 (d, J 4.9 Hz, 2H), 3.88 (s, 3H). MS (ESI) m/z: 512.7 (M−1).

Step 2: 4-((3-(2,6-dichloro-2'-(trifluoromethoxy)-[1,1'-biphenyl]-4-yl)ureido)methyl)benzoic acid 4-((3-(2,6-dichloro-2'-(trifluoromethoxy)-[1,1'-biphenyl]-4-yl]ureido)methyl)methyl benzoate (80 mg, 0.16 mmol), lithium hydroxide (19 mg, 0.48 mmol), ethanol (1 mL) and water (0.3 mL) were added to a 25 mL single-mouth bottle for reaction for 2 hours at room temperature. After confirming the completion of the reaction of materials by TLC, the mixture was adjusted to pH 3 with 2N hydrochloric acid, and then extracted with ethyl acetate (10 mL×3). The organic layers were concentrated in vacuo to obtain a crude product, and the crude product was separated by preparative thin layer chromatography for many times to give the product (white solid, 18 mg), with a yield of 24.3%. $^1$H NMR (400 MHz, CD$_3$OD) δ 8.01 (d, J=8.2 Hz, 2H), 7.60 (s, 2H), 7.52 (t, J=7.0 Hz, 1H), 7.47-7.39 (m, 4H), 7.30 (d, J=7.5 Hz, 1H), 4.48 (s, 2H). MS (ESI) m/z: 496.7 (M−1).

Example 15: 2-(4-((3-(2,6-dichloro-2'-(trifluoromethoxy)-[1,1'-biphenyl]-4-yl)ureido)methyl)phenyl)acetic acid

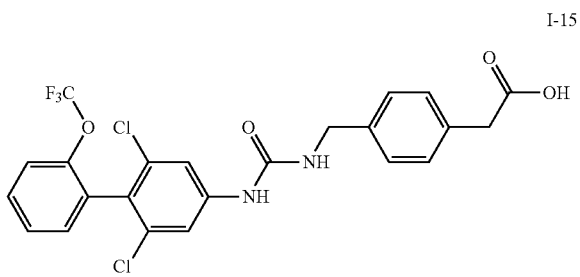 [SMILES: O=C(O)Cc1ccc(CNC(=O)Nc2cc(Cl)c(-c3ccccc3OC(F)(F)F)c(Cl)c2)cc1]

I-15

Step 1: methyl 4-aminomethylphenylacetate

P-methyl cyanobenzoate (200 mg, 1.14 mmol), methanol (2 mL), a small amount of Pd/C and 2 drops of concentrated hydrochloric acid were added to a 25 mL single-mouth bottle, and stirred to react at room temperature for 3 hours under a hydrogen atmosphere at atmospheric pressure. After confirming reaction completion by TLC, the mixture was filtered, and concentrated in vacuo to give the product of methyl 4-aminomethylphenylacetate (white solid, 178 mg), with a yield of 74.2%. $^1$H NMR (400 MHz, DMSO) δ 8.22 (s, 2H), 7.44 (d, J=8.1 Hz, 2H), 7.30 (d, J=8.1 Hz, 2H), 3.98 (s, 2H), 3.71 (s, 2H), 3.61 (s, 3H). MS (ESI) m/z: 180.1 (M+1).

Step 2: 2-(4-((3-(2,6-dichloro-2'-(trifluoromethoxy)-[1,1'-biphenyl]-4-yl)ureido)methyl)benzyl)methyl acetate 2,6-dichloro-2'-(trifluoromethoxy)-[1,1'-biphenylyl]-4-amine (40 mg, 0.12 mmol), DCM (3 mL), and DIEA (31 mg, 0.24 mmol) were added to a 25 mL single-mouth bottle, and stirred for 5 min under ice bath, and then triphosgene (15 mg, 0.05 mmol) was added, and the reaction was continued under ice bath for 30 min, and then 4-aminomethylphenylacetic acid methyl ester (27 mg, 0.15 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (dichloromethane:methanol=50:1) to give the product of 2-(4-((3-(2,6-dichloro-2'-(trifluoromethoxy)-[1,1'-biphenyl]-4-yl)ureido)methyl)benzyl)methyl acetate (white solid, 25 mg), with a yield of 38.5%. $^1$H NMR (400 MHz, CDCl$_3$) δ 7.60 (s, 1H), 7.48-7.42 (t, J=7.1 Hz, 1H), 7.42 (s, 2H), 7.39-7.31 (m, 2H), 7.24-7.22 (d, J=6.5 Hz, 1H), 7.20-7.11 (m, 4H), 5.66 (s, 1H), 4.27-4.25 (d, J=52 Hz, 2H), 3.71 (s, 3H), 3.63 (s, 2H), 1.87 (s, 1H). MS (ESI) m/z: 527.1 (MH+).

Step 3: 2-(4-((3-(2,6-dichloro-2'-(trifluoromethoxy)-[1,1'-biphenyl]-4-yl)ureido)methyl)benzyl)acetic acid 2-(4-((3-(2,6-dichloro-2'-(trifluoromethoxy)-[1,1'-biphenyl]-4-yl)ureido)methyl)benzyl)methyl acetate (25 mg, 0.047 mmol), sodium hydroxide (5.7 mg, 0.14 mmol), ethanol (2 mL) and water (0.5 mL) were added to a 25 mL single-mouth bottle, and reacted at room temperature for 2 hours. After confirming the completion of reaction by TLC, the reaction mixture was adjusted with 2N hydrochloric acid to pH 3. The mixture was extracted with ethyl acetate (10 mL×3), and the organic layer was concentrated in vacuo to give the product of 2-(4-((3-(2,6-dichloro-2'-(trifluoromethoxy)-[1,1'-biphenyl]-4-yl)ureido)methyl)benzyl) acetic acid (white solid, 18 mg), with a yield of 75.0%. $^1$H NMR (400 MHz, CD$_3$OD) δ 7.59 (s, 2H), 7.54-7.51 (t, J=7.1 Hz, 1H), 7.44-7.39 (m, 2H), 7.33-7.25 (m, 5H), 4.39 (s, 2H), 3.59 (s, 2H). MS (ESI) m/z: 513.1 (MH+).

Example 16: 2-(4-((3-(2-chloro-6-cyano-2'-(trifluoromethoxy)-[1,1'-biphenyl]-4-yl)ureido) methyl)phenyl)acetic acid

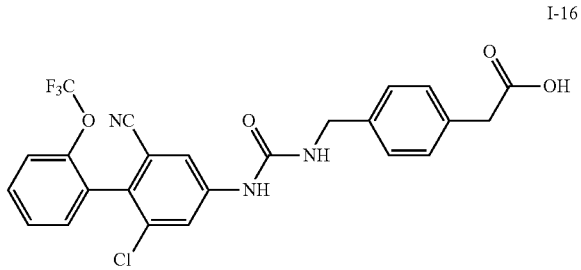 [SMILES: N#Cc1cc(NC(=O)NCc2ccc(CC(=O)O)cc2)cc(Cl)c1-c1ccccc1OC(F)(F)F]

I-16

Step 1: 3-chloro-5-cyano-2-bromobenzene 2-amino-3-chloro-5-nitrobenzonitrile (3 g, 15 mmol), copper bromide (4 g, 18 mmol) and acetonitrile (50 mL) were added to a 25 mL single-mouth bottle. After the obtained mixture was stirred for 5 min under ice bath, n-pentyl nitrite (6.76 g, 57.8 mmol) was weighed and added to acetonitrile (20 mL), and added dropwise to the mixture under ice bath, and then the reaction was continued under ice bath for 30 minutes. The reaction mixture was naturally warmed to room temperature and allowed to react overnight. Water (100 mL) was added, and the reaction mixture was extracted with ethyl acetate (100 mL×3), washed with water (100 mL), washed with saturated sodium chloride (100 mL), and dried over anhydrous sodium sulfate, and the solvent was dried with rotation under vacuum to get a crude product. And then the crude product was separated by a silica gel column to give the product of 3-chloro-5-cyano-2-bromobenzene (yellow solid, 2.3 g), with a yield of 58.4%. $^1$H NMR (400 MHz, CDCl$_3$) δ 8.52 (d, J=2.4 Hz, 1H), 8.41 (d, J=2.4 Hz, 1H).

Step 2: 6-chloro-4-nitro-2'(trifluoromethoxy)-[1,1'-biphenylyl]-2-carbonitrile 2-bromo-3-chloro-5-nitrobenzonitrile (300 mg, 1.15 mmol), 2-trifluoromethoxy phenylboronic acid (355 mg, 1.72 mmol), Pd$_2$(dba)$_3$ (11 mg, 0.012 mmol), tri-tert-butylphosphonium tetrafluoroborate (10 mg, 0.033 mmol), potassium phosphate trihydrate (897 mg, 3.45 mmol) and 1,4-dioxane/H$_2$O (10 mL/1 mL) were added to a microwave tube. The mixture was nitrogen sparged for 5 min, and stirred and heated to 100° C. for 1.5 hours under microwave, and the resulting mixture was washed with saturated ammonium chloride (20 mL), and separated by silica gel column (petroleumether:ethylacetate=30:1) to give the product of 6-chloro-4-nitro-2'(trifluoromethoxy)-[1,1'-biphenylyl]-2-carbonitrile (yellow solid, 270 mg), with a yield of 68.7%. $^1$H NMR (400 MHz, CDCl$_3$) δ 8.59-8.58 (d, J=2.1 Hz, 1H), 8.54-8.53 (d, J=2.1 Hz, 1H), 7.65-7.62 (t, J=7.1 Hz, 1H), 7.55-7.45 (m, 2H), 7.37-7.35 (d, J 7.5 Hz, 1H).

Step 3: 4-amino-6-chloro-2'-(trifluoromethoxy)-[1,1-biphenylyl]-2-carbonitrile 6-chloro-4-nitro-2'(trifluoromethoxy)-[1,1'-biphenylyl]-2-carbonitrile (265 mg, 0.77 mmol), stannous chloride dihydrate (524 mg, 2.31 mmol), ethanol (20 mL), and concentrated hydrochloric acid (2 mL) were added to a 25 mL single-mouth bottle, and heated to react for 3 hours at 60° C. After confirming completion of reaction by TLC, the mixture was cooled to room temperature, added with 2N hydrogen hydroxide solution to adjust its pH to alkaline, and extracted with ethyl acetate (20 mL×3). The organic layers were combined, and washed with saturated sodium chloride (30 mL), and the solvent was dried with rotation under vacuum to give the product of 4-amino-6-chloro-2'-(trifluoromethoxy)-[1,1biphenylyl]-2-carbonitrile (white solid, 240 mg), with a yield of 99.6%. $^1$H NMR (400 MHz, CDCl$_3$) δ 7.51-7.48 (t, J=7.0 Hz, 1H), 7.43-7.36 (m, 2H), 7.34-7.33 (d, J=6.3 Hz, 1H), 6.99 (d, J=2.3 Hz, 1H), 6.92 (d, J=2.3 Hz, 1H), 2.96 (s, 2H).

Step 4: 2-(4-((3-(2-chloro-6-cyano-2'-(trifluoromethoxy)-[1,1'-biphenyl]-4-yl)ureido) methyl)benzyl)methyl acetate 4-amino-6-chloro-2'-(trifluoromethoxy)-[1,1-biphenylyl]-2-carbonitrile (80 mg, 0.26 mmol), DCM (4 mL), and DIEA (67 mg, 0.52 mmol) were added to a 25 mL single-mouth bottle, and stirred for 5 min under ice bath, and then triphosgene (29.7 mg, 0.10 mmol) was added, and the reaction was continued under ice bath for 30 minutes, and then methyl 4-aminomethylphenylacetate (50 mg, 0.28 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleum ether:ethyl acetate=10:1) to give the product of 2-(4-((3-(2-chloro-6-cyano-2'-(trifluoromethoxy)-[1,1'-biphenyl]-4-yl)ureido) methyl)benzyl) methyl acetate (white solid, 38 mg), with a yield of 28.8%. $^1$H NMR (400 MHz, CDCl$_3$) δ 7.87-7.78 (m, 2H), 7.54-7.47 (m, 2H), 7.41-7.37 (t, J=7.2 Hz, 2H), 7.31-7.29 (d, J=6.5 Hz, 1H), 7.21-7.16 (m, 4H), 5.70 (s, 1H), 4.29-4.28 (d, J=Hz, 2H), 3.67 (s, 3H), 3.62 (s, 2H). MS (ESI) m/z: 518.2 (MH+).

Step 5: 2-(4-((3-(2-chloro-6-cyano-2'-(trifluoromethoxy)-[1,1'-biphenyl]-4-yl)ureido)methyl) benzyl) acetic acid 2-(4-((3-chloro-6-cyano-2'-(trifluoromethoxy)-[1,1'-biphenyl]-4-yl)ureido)methyl)benzyl)methyl acetate (38 mg, 0.014 mmol), lithium hydroxide monohydrate (9.2 mg, 0.22 mmol), ethanol (1 mL), and water (0.3 mL) were added to a 25 mL single-mouth bottle, and reacted for 2 hours at room temperature. After confirming completion of the reaction of materials by TLC, the mixture was adjusted to pH 3 with 2N hydrochloric acid, and extracted with ethyl acetate (10 mL×3). The organic layer was concentrated in vacuo to give the product of 2-(4-((3-(2-chloro-6-cyano-2'-(trifluoromethoxy)-[1,1'-biphenyl]-4-yl)ureido)methyl) benzyl) acetic acid (white solid, 27 mg), with a yield of 72.9%. $^1$H NMR (400 MHz, CD$_3$OD) δ 7.93-7.92 (d, J=2.1 Hz, 1H), 7.87-7.86 (d, J=2.1 Hz, 1H), 7.61-6.57 (t, J=11.1, 4.6 Hz, 1H), 7.51-7.44 (m, 2H), 7.43-7.38 (m, 1H), 7.32-7.26 (m, 3H), 7.25-7.23 (d, J=11.0 Hz, 1H), 4.39 (s, 2H), 3.59 (s, 2H). MS (ESI) m/z: 504.1 (MH+).

Example 17: 2-(4-((3-(2-chloro-6-methyl-2'-(trifluoromethoxy)-[1,1'-biphenyl]-4-yl)ureido)methyl) phenyl)acetic acid

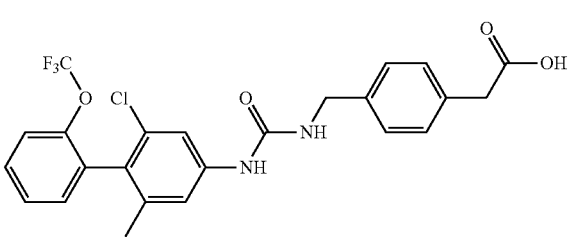

I-17

Step 1: 2-bromo-1-chloro-3-methyl-5-nitrobenzene 2-chloro-6-methyl-4-nitroaniline (500 mg, 2.68 mmol), copper bromide (718 mg, 3.22 mmol), and acetonitrile (8 mL) were added to a 25 mL three-necked bottle and stirred for 5 min under ice bath. Tert-butyl nitrite (470 mg, 4.02 mmol) was dissolved in acetonitrile (2 mL), and then added dropwise to the three-necked bottle, and the mixture was allowed to warm to room temperature, reacting overnight. H$_2$O (20 mL) was added, and the mixture was extracted with ethyl acetate (20 mL×3). The organic layers were combined, and washed with saturated sodium chloride (20 mL), and the solvent was dried with rotation under vacuum, to give the product of 2-bromo-1-chloro-3-methyl-5-nitrobenzene (yellow solid, 650 mg), with a yield of 96.7%. $^1$H NMR (400 MHz, CDCl$_3$) δ 8.17 (s, 1H), 8.01 (s, 1H), 2.57 (s, 3H).

Step 2: 4-bromo-3-chloro-5-methylaniline 2-bromo-1-chloro-3-methyl-5-nitrobenzene (640 mg, 2.56 mmol), stannous chloride dihydrate (2.25 g, 10 mmol), concentrated hydrochloric acid (0.5 mL), ethanol (10 mL) and tetrahydrofuran (4 mL) were added to a 25 mL single-mouth bottle, heated to react for 2 hours at 60° C. while stirring, and then naturally cooled to room temperature. Then water (30 mL) and 20% sodium chloride (50 mL) were added, and the mixture was extracted with ethyl acetate (50 mL×3). The organic layers were combined, washed with saturated sodium chloride (50 mL), dried over anhydrous sodium sulfate, and filtered, and the solvent was dried with rotation under vacuum, to give the product of 4-bromo-3-chloro-5-methylaniline (yellow solid, 540 mg), with a yield of 95.9%. $^1$H NMR (400 MHz, CDCl$_3$) δ 6.65 (d, J=2.3 Hz, 1H), 6.47 (s, 1H), 3.65 (s, 2H), 2.34 (s, 3H). MS (ESI) m/z: 220.0 (MH+)

Step 3: 2-chloro-6-methyl-2'-(trifluoromethoxy)-[1,1'-biphenylyl]-4-amine 4-bromo-3-chloro-5-methylaniline (500 mg, 2.3 mmol), 2-trifluoromethoxy phenylboronic acid (710 mg, 3.5 mmol), Pd$_2$(dba)$_3$ (210 mg, 0.23 mmol), tert-butylphosphonium tetrafluoroborate (200 mg, 0.7 mmol), sodium carbonate (730 mg, 6.9 mmol), and 1,4-dioxane/water (10 mL/1 mL) were added to a microwave tube. The mixture was nitrogen sparged for 5 min, and stirred and heated to 120° C. for 3 hours under microwave, washed with saturated ammonium chloride (50 mL), and separated by silica gel column (petroleumether:ethylacetate=20:1-10:1) to give the product of 2-chloro-6-methyl-2'-(trifluoromethoxy)-[1,1'-biphenylyl]-4-amine (yellow solid, 190 mg), with a yield of 27.8%. MS (ESI) m/z: 302.1 (MH+). MS (ESI) m/z: 220.0 (MH+).

Step 4: 2-(4-((3-(2-chloro-6-methyl-2'-(trifluoromethoxy)-[1,1'-biphenyl]-4-yl)ureido)methyl) benzyl)ethyl acetate 2-chloro-6-methyl-2'-(trifluoromethoxy)-[1,1'-biphenylyl]-4-amine (30 mg, 0.1 mmol) DCM (1 mL) and DIEA (26 mg, 0.2 mmol) were added to a 25 mL single-mouth bottle, and stirred for 5 min under ice bath, and then triphosgene (12 mg, 0.04 mmol) was added, and the reaction was continued under ice bath for 30 minutes, and then methyl 4-aminomethylphenylacetate (22 mg, 0.12 mmol) was added, and the reaction was continued under ice bath for 30 min, then at room temperature overnight. H$_2$O (10 mL) was added, and the obtained mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (dichloromethane:methanol=20:1) to give the product of 2-(4-((3-(2-chloro-6-methyl-2'-(trifluoromethoxy)-[1,1'-biphenyl]-4-yl)ureido)methyl) benzyl)ethyl acetate (white solid, 31 mg), with a yield of 62.0%. $^1$H NMR (400 MHz, CDCl$_3$) δ 7.45-7.38 (m, 1H), 7.38-7.30 (m, 3H), 7.22-7.11 (m, 6H), 5.65 (s, 1H), 4.28 (s, 2H), 3.68 (s, 3H), 3.60 (s, 2H), 1.95 (s, 3H). MS (ESI) m/z: 507.2 (MH+).

Step 5: 2-(4-((3-(2-chloro-6-methyl-2'-(trifluoromethoxy)-[1,1'-biphenyl]-4-yl)ureido) methyl) benzyl)acetic acid 2-(4-((3-chloro-6-methyl-2'-(trifluoromethoxy)-[1,1'-biphenyl]-4-yl)ureido)methyl)benzyl)methyl acetate (30 mg, 0.059 mmol), sodium hydroxide (7.1 mg, 0.177 mmol), ethanol (1 mL), and water (0.3 mL) were added to a 25 mL single-mouth bottle, and reacted for 2 hours at room temperature. After confirming completion of the reaction of materials by TLC, the mixture was adjusted to pH 3 with 2N hydrochloric acid, and extracted with ethyl acetate (10 mL×3). The organic layer was concentrated in vacuo to give the product of 2-(4-((3-(2-chloro-6-methyl-2'-(trifluoromethoxy)-[1,1'-biphenyl]-4-yl)ureido) methyl)benzyl) acetic acid (white solid, 23 mg), with a yield of 79.3%. $^1$H NMR (400 MHz, CD$_3$OD) δ 7.55 (s, 1H), 7.51-7.47 (t, J=1.6, 6.4 Hz, 1H), 7.43-7.38 (m, 2H), 7.33-7.22 (m, 5H), 7.19 (s, 1H), 4.39 (s, 2H), 3.59 (s, 2H), 2.00 (s, 3H). MS (ESI) m/z: 493.1 (MH+).

Example 18: 2-(4-((3-(2-chloro-2'-(trifluoromethoxy)-[1,1'-biphenyl]-4-yl)ureido)methyl)phenyl)acetic acid

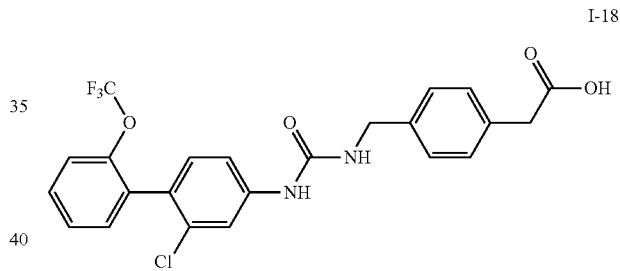

I-18

Step 1: 2-chloro-2'-(trifluoromethoxy)-[1,1'-biphenylyl]-4-amine 4-chloro-3-bromoaniline (500 mg, 2.43 mmol), 2-trifluoromethoxyphenylboronic acid (649 mg, 3.15 mmol), Pd$_2$(dppf)Cl$_2$ (69 mg, 0.12 mmol), potassium carbonate (1.01 g, 7.29 mmol), and acetonitrile/water (4 mL/1 mL) were added to a microwave tube. The mixture was nitrogen sparged for 5 min, and stirred and heated to 120° C. for 2 hours under microwave, washed with saturated ammonium chloride (20 mL), and separated by silica gel column (petroleumether:ethylacetate=10:1-5:1) to give the product of 2-chloro-2'-(trifluoromethoxy)-[1,1'-biphenylyl]-4-amine (yellow oil, 610 mg), with a yield of 88.5%. $^1$H NMR (400 MHz, CDCl$_3$) δ 7.42-7.35 (m, 1H), 7.36-7.28 (m, 3H), 7.06-7.04 (d, J=8.2 Hz, 1H), 6.81-6.80 (d, J=1.9 Hz, 1H), 6.64-6.62 (d, J=8.2 Hz, 1H), 3.57 (s, 2H). MS (ESI) m/z: 288.0 (MH+)

Step 2: 2-(4-((3-chloro-2'-(trifluoromethoxy)-[1,1'-biphenyl]-4-yl)ureido)methyl)benzyl)methyl acetate 2-chloro-2'-(trifluoromethoxy)-[1,1'-biphenylyl]-4-amine (100 mg, 0.34 mmol), dichloromethane (4 mL), and DIEA (129 mg, 1 mmol) were added to a 25 mL single-mouth bottle, and stirred for 5 min under ice bath, and then triphosgene (35 mg, 0.12 mmol) was added, and the reaction was continued under ice bath for 30 minutes, and then methyl 4-aminomethylphenylacetate (73 mg, 0.34 mmol) was added, and the reaction was continued under ice bath for 30 min, then at room temperature overnight. H₂O (10 mL) was added, and the obtained mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleum ether:ethyl acetate=2:1) to give the product of 2-(4-((3-chloro-2'-(trifluoromethoxy)-[1,1'-biphenyl]-4-yl)ureido)methyl)benzyl)meth yl acetate (white solid, 31 mg), with a yield of 18.1%. MS (ESI) m/z: 493.1 (MH+).

Step 3: 2-(4-((3-(2-chloro-2'-(trifluoromethoxy)-[1, 1'-biphenyl]-4-yl)ureido)methyl)benzyl)acetic acid 2-(4-((3-(2-chloro-2'-(trifluoromethoxy)-[1,1'-biphenyl)-4-urela) methyl)benzyl)methyl acetate (30 mg, 0.06 mmol), sodium hydroxide (7.3 mg, 0.18 mmol), ethanol (2 mL) and water (0.5 mL) were added to a 25 mL single-mouth bottle, and reacted at room temperature for 2 hours. After confirming completion of the reaction of materials by TLC, the mixture was adjusted to pH 3 with 2N hydrochloric acid, and extracted with ethyl acetate (10 mL×3). The organic layer was concentrated in vacuo to give the product (white solid, 23 mg), with a yield of 79.3%. ¹H NMR (400 MHz, CD₃OD) δ 7.71-7.70 (d, J=1.9 Hz, 1H), 7.50-7.47 (t, J=7.6, 1H), 7.42-7.36 (m, 3H), 7.35-7.23 (m, 6H), 7.18-7.16 (d, J=8.4 Hz, 1H), 4.40 (s, 2H), 3.60 (s, 2H). MS (ESI) m/z: 479.1 (MH+).

Example 19: 2-(4-((3-(2,6-difluoro-2'-(trifluoromethoxy)-[1,1'-biphenyl]-4-yl)ureido)methyl)phenyl)acetic acid

I-19

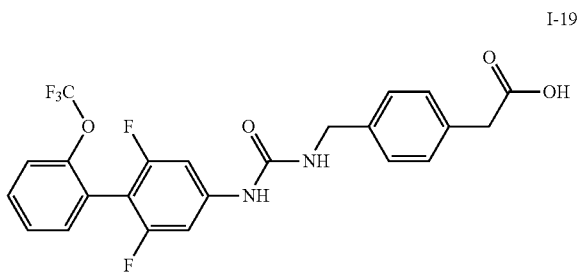

Step 1: 2,6-difluoro-2'-trifluoromethoxy-[1,1'-biphenylyl]-4-amine 4-bromo-3,5-difluoroaniline (500 mg, 2.4 mmol), 2-trifluoromethoxybenzeneboronic acid (590 mg, 2.9 mmol), Pd₂(dppf)Cl₂ (98 mg, 0.12 mmol), cesium carbonate (2.35 g, 7.2 mmol) and acetonitrile/water (10 mL/1 mL) were added to a microwave tube. The mixture was nitrogen sparged for 5 min, stirred and heated to 120° C. for 1 hour under microwave, washed with saturated ammonium chloride (20 mL), and separated by silica gel column (petroleumether:ethylacetate=50:1) to give the product of 2,6-difluoro-2'-trifluoromethoxy-[1,1'-biphenylyl]-4-amine (yellow oil, 460 mg), with a yield of 66.3%. ¹H NMR (400 MHz, CDCl₃) δ 7.47-7.28 (m, 4H), 6.29-6.27 (d, J=9.1 Hz, 2H), 3.67 (s, 2H). MS (ESI) m/z: 290.1 (MH+).

Step 2: 2-(4-((3-(2,6-difluoro-2'-(trifluoromethoxy)-[1,1'-biphenyl]-4-yl)ureido)methyl)phenyl)methyl acetate 2,6-difluoro-2'-(trifluoromethoxy)-[1,1'-biphenylyl]-4-amine (20 mg, 0.069 mmol), DCM (1 mL), and DIEA (18 mg, 0.03 mmol) were added to a 25 mL single-mouth bottle, and stirred for 5 min under ice bath, and then triphosgene (10 mg, 0.11 mmol) was added, and the reaction was continued under ice bath for 30 minutes, and then methyl 4-aminomethylphenylacetate (16 mg, 0.11 mmol) was added, and the reaction was continued under ice bath for 30 min, then at room temperature overnight. H₂O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleumether:ethylacetate=2:1) to give the product of 2-(4-((3-(2,6-difluoro-2'-(trifluoromethoxy)-[1,1'-biphenyl]-4-yl) ureido)methyl)phenyl)methyl acetate (white solid, 7 mg), with a yield of 20.6%. ¹H NMR (400 MHz, CDCl₃) δ 7.49-7.37 (m, 2H), 7.38-7.30 (m, 3H), 7.21-7.13 (m, 4H), 7.02-7.00 (d, J=9.4 Hz, 2H), 5.46-5.43 (t, J=5.2 Hz, 1H), 4.28 (d, J=53 Hz, 2H), 3.70 (s, 3H), 3.63 (s, 2H). MS (ESI) m/z: 495.2 (MH+).

Step 3: 2-(4-((3-(2,6-difluoro-2'-(trifluoromethoxy)-[1,1'-biphenyl]-4-yl) ureido)methyl)phenyl)acetic acid 2-(4-((3-2,6-difluoro-2'-(trifluoromethoxy)-[1,1'-biphenyl]-4-yl)ureido)methyl)phenyl)methyl acetate (7 mg, 0.014 mmol), sodium hydroxide (17 mg, 0.042 mmol), ethanol (1 mL), and water (0.3 mL) were added to a 100 mL single-mouth bottle, reacted for 2 hours at room temperature. After confirming completion of the reaction of materials by TLC, the mixture was adjusted to pH 3 with 2N hydrochloric acid, and extracted with ethyl acetate (10 mL×3). The organic layer was concentrated in vacuo to give the product of 2-(4-((3-(2,6-difluoro-2'-(trifluoromethoxy)-[1,1'-biphenyl]-4-yl) ureido)methyl)phenyl)acetic acid (white solid, 5 mg), with a yield of 73.5%. ¹H NMR (400 MHz, CD₃OD) δ 7.58-7.47 (m, 1H), 7.37 (m, 3H), 7.29 (q, J=10.6, 4H), 7.17 (d, J=9.9 Hz, 2H), 4.39 (s, 2H), 3.59 (s, 2H). MS (ESI) m/z: 481.2 (MH+).

Example 20: 2-(4-((3-(2,6-dichloro-2'-(difluoromethoxy)-[1,1'-biphenyl]-4-yl)ureido)methyl)phenyl)acetic acid)

I-20

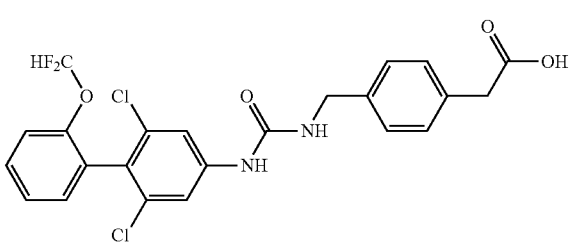

Step 1: 2,6-dichloro-2'-(difluoromethoxy)-[1,1'-biphenylyl]-4-amine 4-bromo-3,5-dichloroaniline (500 mg, 2.07 mmol), 2-difluoromethoxybenzene borate (672 mg, 2.49 mmol), Pd$_2$(dba)$_3$ (378 mg, 0.4 mmol), tri-tert-butylphosphonium tetrafluoroborate (180 mg, 0.62 mmol), cesium carbonate (2.02 g, 6.01 mmol), and 1,4-dioxane/water (13 mL/2 mL) were added to a microwave tube. The mixture was nitrogen sparged for 5 min, stirred and heated to 120° C. for 3 hours under microwave, washed with saturated ammonium chloride (20 mL), and separated by silica gel column (petroleumether:ethylacetate=10:1-5:1) to give the product of 2,6-dichloro-2'-(difluoromethoxy)-[1,1'-biphenylyl]-4-amine (yellow oil, 140 mg), with a yield of 15.5%. $^1$H NMR (400 MHz, CDCl$_3$) δ 7.44-7.40 (t, J=6.8 Hz, 1H), 7.31-7.27 (t, J=8 Hz, 1H), 7.25-7.20 (m, 2H), 6.72 (s, 2H), 6.55-6.18 (t, J=74.1 Hz, 1H), 3.86 (s, 2H).

Step 2: 2-(4-((3-(2,6-dichloro-2'-(difluoromethoxy)-[1,1'-biphenyl]-4-yl)ureido)methyl)phenyl)methyl acetate 2,6-dichloro-2'-(difluoromethoxy)-[1,1'-biphenylyl]-4-amine (50 mg, 0.11 mmol), dichloromethane (2 mL) and DIEA (63 mg, 0.49 mmol) were added to a 25 mL single-mouth bottle, and stirred under ice bath for 5 minutes, and then triphosgene (19.5 mg, 0.066 mmol) was added, and the reaction was continued under ice bath for 30 min, and then methyl 4-aminomethylphenylacetate (35 mg, 0.197 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (dichloromethane:methanol=50:1) to give the product of 2-(4-((3-(2,6-dichloro-2'-(difluoromethoxy)-[1,1'-biphenyl]-4-yl)ureido)methyl)phenyl)methyl acetate (yellow oil, 33 mg), with a yield of 49.3%. $^1$H NMR (400 MHz, CDCl$_3$) δ 7.68 (s, 1H), 7.44-7.40 (t, J=7.8 Hz, 1H), 7.35 (s, 2H), 7.30-7.26 (t, J=8.0 Hz, 1H), 7.24-7.21 (d, J=8.2 Hz, 1H), 7.20-7.08 (m, 5H), 6.53-6.18 (t, J=74.0 Hz, 1H), 5.77 (d, J=5.1 Hz, 1H), 4.24-4.22 (d, J=5.3 Hz, 2H), 3.68 (s, 3H), 3.60 (s, 2H). MS (ESI) m/z: 509.1 (MH+).

Step 3: 2-(4-((3-(2,6-dichloro-2'-(difluoromethoxy)-[1,1'-biphenylyl]-4-yl)ureido)methyl)phenyl)acetic acid 2-(4-((3-(2,6-dichloro-2'-(difluoromethoxy)-[1,1'-biphenyl]-4-yl)ureido) methyl)benzyl)methyl acetate (33 mg, 0.065 mmol), sodium hydroxide (7.78 mg, 0.19 mmol), ethanol (2 mL), and water (0.5 mL) were added to a 25 mL single-mouth bottle, and reacted for 2 hours at room temperature. After confirming completion of the reaction of materials by TLC, the mixture was adjusted to pH 3 with 2N hydrochloric acid, and extracted with ethyl acetate (10 mL×3). The organic layer was concentrated in vacuo to give the product of 2-(4-((3-(2,6-dichloro-2'-(difluoromethoxy)-[1,1'-biphenylyl]-4-yl)ureido)methyl) phenyl)acetic acid (white solid, 30 mg), with a yield of 90.9%. $^1$H NMR (400 MHz, CD$_3$OD) δ 7.57 (s, 2H), 7.44 (t, J=7.2 Hz, 1H), 7.31-7.25 (m, 5H), 7.24-7.20 (t, J=8.0 Hz, 2H), 6.85-6.8 (t, J 73.9 Hz, 1H), 4.38 (s, 2H), 3.59 (s, 2H). MS (ESI) m/z: 495.1 (MH+).

Example 21: 2-(4-((3-(2'-(difluoromethoxy)-2,6-dimethyl-[1,1'-biphenyl]-4-yl)ureido)methyl)phenyl)acetic acid

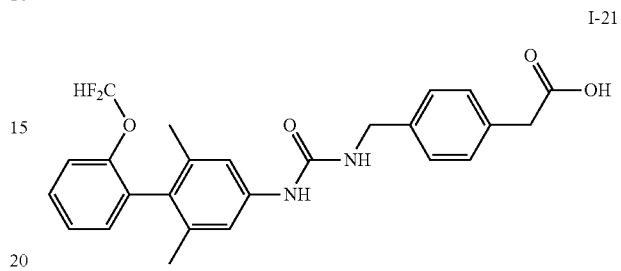

I-21

Step 1: 2-(2-(difluoromethoxy)benzyl)-4,4,5,5-tetramethyl-1,3,2-dioxaborolane 2-difluoromethoxy)bromobenzene (2 g, 9 mmol), bis(pinacolato)diboron (4.6 g, 18 mmol), potassium acetate (3.62 g, 36 mmol), Pd(dppf)Cl$_2$ (73 mg, 0.09 mmol), and 1,4-dioxane (100 mL) were added to a 100 mL three-necked bottle, heated to 120° C. and reacted overnight while stirring. The mixture was cooled to room temperature, and added with water (50 mL), and extracted with ethyl acetate (50 mL×3). The organic layers were combined, washed with saturated sodium chloride (100 mL), dried over anhydrous sodium sulfate, and filtered, and the filtrate was concentrated in vacuo to obtain a crude product. The crude product was separated by a silica gel column (petroleumether:ethylacetate=50:1) to give the product of 2-(2-(difluoromethoxy)benzyl)-4,4,5,5-tetramethyl-1,3,2-dioxaborolane (orange solid, 2.1 g), with a yield of 86.7%. $^1$H NMR (400 MHz, CDCl$_3$) δ 7.76-7.75 (d, J 6.3 Hz, 1H), 7.43 (t, J=6.9 Hz, 1H), 7.26-7.22 (d, J 7.2 Hz, 1H), 7.15 (d, J 8.2 Hz, 1H), 6.52 (t, J=75.5 Hz, 1H), 1.35 (s, 12H).

Step 2: 4-bromo-3,5-dimethylaniline 3,5-dimethylaniline (2 g, 16.5 mmol), and acetonitrile (80 mL) were added to a 25 mL single-mouth bottle, and stirred for 5 min under ice bath, then NBS (3.94 g, 21.6 mmol) was dissolved in acetonitrile (20 mL), added dropwise to the single-mouth bottle, and after addition, reacted for 2 hours under ice bath. After the reaction, water (50 mL) was added, and the mixture was extracted with ethyl acetate (100 mL×3). The organic layers were combined, and concentrated in vacuo to remove the solvent to separate by a silica gel column (petroleumether:ethylacetate=10:1-4:1) to give the product of 4-bromo-3,5-dimethylaniline (white solid, 2.3 g), with a yield of 69.7%. $^1$H NMR (400 MHz, CDCl$_3$) δ 6.44 (s, 2H), 3.45 (s, 2H), 2.31 (s, 6H). MS (ESI) m/z: 200.1 (MH+).

Step 3: 2'-(difluoromethoxy)-2,6-dimethyl-[1,1'-dibiphenylyl]-4-amine 4-bromo-3,5-dimethylaniline (293 mg, 1.46 mmol), 2-difluoromethoxybenzene borate (330 mg, 1.2 mmol), Pd$_2$(dba)$_3$ (110 mg, 0.12 mmol), tert-butylphosphonium tetrafluoroborate (104 mg, 0.36 mmol), cesium carbonate (1.17 g, 3.6 mmol) and 1,4-dioxane/water (4 mL/1 mL) were added to a microwave tube. The mixture was nitrogen sparged for 5 min, and stirred and heated to 120° C. for 3 hours under microwave. The mixture then was washed with saturated ammonium chloride (20 mL), and separated by silica gel column (petroleumether:ethylacetate=10:1-4:1) to give the product of 2'-(difluoromethoxy)-2,6-dimethyl-[1,1'-dibiphenylyl]-4-amine (yellow oil, 62 mg), with a yield of 15.6%. $^1$H NMR (400 MHz, CDCl$_3$) δ 7.3, 7-7.33 (t, J=1.6, 1H), 7.30-7.21 (m, 2H), 7.17 (dd, 7=7.3, 1.1 Hz, 1H), 6.48 (s, 2H), 6.45-6.07 (t, J=74.6 Hz, 1H), 3.50 (s, 2H), 1.95 (s, 6H). MS (ESI) m/z: 264.1 (MH+).

Step 4: 2-(4-((3-(2'-(difluoromethoxy)-2,6-dimethyl-[1,1'-biphenyl]-4-yl)ureido)methyl)phen yl) methyl acetate 2,6-dimethyl-2'-(difluoromethoxy)-[1,1'-biphenylyl]-4-amine (30 mg, 0.11 mmol), DCM (2 mL), and DIEA (28 mg, 0.22 mmol) were added to a 25 mL single-mouth bottle, and stirred for 5 min under ice bath, and then triphosgene (13 mg, 0.044 mmol) was added, and the reaction was continued under ice bath for 30 min, and then methyl 4-aminomethylphenylacetate (25 mg, 0.14 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (dichloromethane:methanol=20:1) to give the product of 2-(4-((3-(2'-(difluoromethoxy)-2,6-dimethyl-[1,1'-biphenyl]-4-yl)ureido)methyl)phen yl) methyl acetate (yellow oil, 43 mg), with a yield of 81.1%. $^1$H NMR (400 MHz, CDCl$_3$) δ 7.37-7.35 (t, J 7.6 Hz, 1H), 7.27-7.19 (m, 7H), 7.10-7.08 (d, J 7.3 Hz, 1H), 7.01 (s, 1H), 6.44-6.07 (t, J=74.2 Hz, 1H), 5.55 (d, J=5.4 Hz, 1H), 4.37-4.35 (d, J=5.4 Hz, 2H), 3.68 (s, 3H), 3.61 (s, 2H), 1.94 (s, 6H). MS (ESI) m/z: 469.2 (MH+).

Step 5: 2-(4-((3-(2'-(difluoromethoxy)-2,6-dimethyl-[1,1'-biphenyl]-4-yl)ureido)methyl)phenyl) acetic acid 2-(4-((3-(2'-(difluoromethoxy)-2,6-dimethyl-[1,1'-biphenyl]-4-yl)ureido)methyl)benz yl)methyl acetate (43 mg, 0.092 mmol), sodium hydroxide (11 mg, 0.28 mmol), ethanol (3 mL) and water (1 mL) were added to a 25 mL single-mouth bottle to react for 1 hour at room temperature. After confirming completion of the reaction of materials by TLC, the mixture was adjusted to pH 3 with 2N hydrochloric acid, and extracted with ethyl acetate (10 mL×3). The organic layer was concentrated in vacuo to give the product of 2-(4-((3-(2'-(difluoromethoxy)-2,6-dimethyl-[1,1'-biphenyl]-4-yl)ureido)methyl)phen yl) acetic acid (white solid, 36 mg), with a yield of 84.0%. $^1$H NMR (400 MHz, CD$_3$OD) δ 7.42-7.39 (t, J=7.0 Hz, 1H), 7.34-7.23 (m, 6H), 7.13-7.12 (m, 3H), 6.79-6.42 (t, J 74.4 Hz, 2H), 4.38 (s, 2H), 3.59 (s, 2H), 1.95 (s, 6H). MS (ESI) m/z: 455.2 (MH+).

Example 22: 2-(4-((3-(2-(1-methyl-1H-pyrazol-4-yl)-2'-(trifluoromethoxy)-[1,1'-biphenyl]-4-yl) ureido)methyl)phenyl)acetic acid and 2-(4-((3-(2'-(1-methyl-1H-pyrazol-4-yl)-6'-(trifluoromethoxy)-[1,1'-biphenyl]-4-yl)ureido)methyl)phenyl)acetic acid

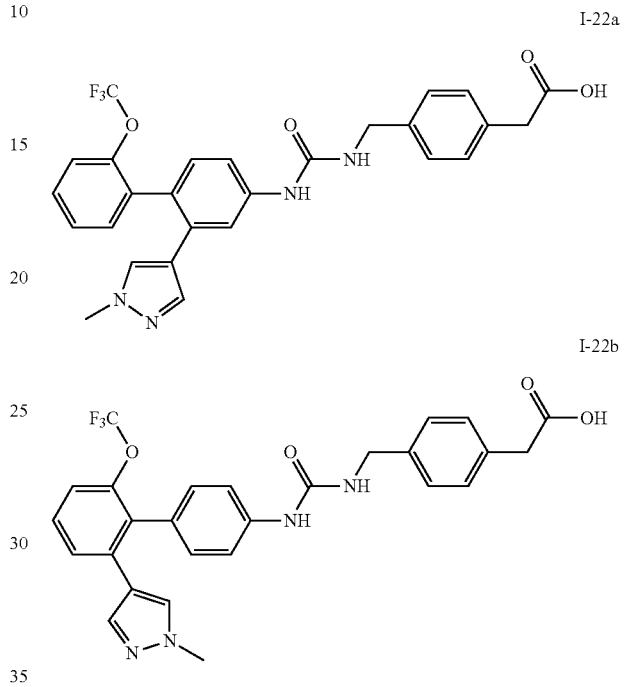

Step 1: 1-bromo-2-chloro-4 nitrobenzene 2-chloro-4-nitroaniline (5 g, 28.9 mmol), copper bromide (7.73 g, 34.7 mmol), and acetonitrile (80 mL) were added to a 25 mL single-mouth bottle, and stirred for 5 minutes under ice bath, and n-pentyl nitrite (6.76 g, 57.8 mmol) was weighed and added to acetonitrile (20 mL). And then the obtained mixture was added dropwise to the reaction solution under ice bath, and then reacted for 30 minutes under ice bath. The reaction mixture was naturally warmed to room temperature and allowed to react overnight. Water (100 mL) was added, and the mixture was extracted with ethyl acetate (100 mL×3), washed with water (100 mL), washed with saturated sodium chloride (100 mL), dried over anhydrous sodium sulfate, and concentrated in vacuo to give the product of 1-bromo-2-chloro-4 nitrobenzene (yellow solid, 5.68 g), with a yield of 82.9%.

Step 2: 2-chloro-4-nitro-2'-trifluoromethoxy-1,1'-biphenyl 1-bromo-2-chloro-4-nitrobenzene (1 g, 0.42 mmol), 2-trifluoromethoxybenzeneboronic acid (1.05 g, 0.51 mmol), Pd$_2$(dppf)Cl$_2$ (160 mg, 0.02 mmol), cesium carbonate (2.77 g, 1.26 mmol), and CH$_3$CN/H$_2$O (12 mL/3 mL) were added to a microwave tube. The mixture was nitrogen sparged for 5 minutes, and stirred and heated to 100° C. for 2 hours under microwave. Ethyl acetate (20 mL) was added, and the mixture was washed with saturated ammonium chloride (20 mL), and the solvent was dried with rotation under vacuum.

The crude product was separated by silica gel column (petroleumether:ethylacetate=30:1) to give the product of 2-chloro-4-nitro-2'-trifluoromethoxy-1,1'-biphenyl (yellow oil, 1.47 g), with a yield of 99.3%. $^1$H NMR (400 MHz, CDCl$_3$) δ 8.38-8.37 (d, J=2.1 Hz, 1H), 8.21-8.18 (dd, J=8.4, 2.2 Hz, 1H), 7.56-7.47 (m, 2H), 7.45-7.39 (m, 2H), 7.37-7.30 (m, 1H).

Step 3: 4,4,5,5-tetramethyl-2-(4-nitro-2'-(trifluoromethoxy)-[1,1'-biphenyl]-2-yl)-1,3,2-dioxaborolan 2-chloro-4-nitro-2'-(trifluoromethoxy)-1,1'-biphenyl (500 mg, 1.55 mmol), bis(pinacolato)diboron (800 mg, 4.65 mmol), Pd$_2$(dba)$_3$ (115 mg, 0.13 mmol), potassium acetate (465 mg, 4.65 mmol), x-phos (240 mg, 0.5 mmol) and 1,4-dioxane (15 mL) were added to a microwave tube. The mixture was nitrogen sparged for 5 min, and stirred and heated to 90° C. for 2 hours under microwave. Then ethyl acetate (20 mL) was added, and the mixture was washed with saturated ammonium chloride (20 mL), and the solvent was dried with rotation under vacuum, and the crude product was separated by silica gel column (petroleumether:ethylacetate=6:1) to give the product of 4,4,5,5-tetramethyl-2-(4-nitro-2'-(trifluoromethoxy)-[1,1'-biphenyl]-2-yl)-1,3,2-dioxaborolan (yellow oil, 130 mg), with a yield of 20.2%.

Step 4: 1-methyl-4-(4-nitro-2'-(trifluoromethoxy)-[1,1'-biphenyl]-2-yl)-1H-pyrazole and 1-methyl-4-(4'-nitro-6-(trifluoromethoxy)-[1,1'-biphenyl]-2-yl)-1H-pyrazole 4,4,5,5-tetramethyl-2-(4-nitro-2'-(trifluoromethoxy)-[1,1'-biphenyl]-2-yl)-1,3,2-dioxaborolan (100 mg, 0.2 mmol), 4-bromo-1-methyl-1H-pyrazole (47 mg, 0.29 mmol), tetrakis(triphenylphosphine)palladium (22 mg, 0.014 mmol), sodium carbonate (80 mg, 0.75 mmol), and 1,4-dioxane/H$_2$O (4 mL/1 mL) were added to a microwave tube. The mixture was nitrogen sparged for 5 min, and stirred and heated to 90° C. for 1.5 hours under microwave, and the resulting mixture was washed with saturated ammonium chloride (20 mL), and separated by silica gel column (petroleum ether:ethyl acetate=1:1) to give the two bathes of yellow oils (15 mg and 20 mg respectively).

Step 5: 2-(1-methyl-1H-pyrazole-4-yl)-2'-(trifluoromethoxy)-[1,1'-biphenylyl]-4-amine and 2'-(1-methyl-1H-pyrazole-4-yl)-6'-(trifluoromethoxy)-[1,1'-biphenylyl]-4-amine 1-methyl-4-(4-nitro-2'-(trifluoromethoxy)-[1,1'-biphenyl]-2-yl)-1H-pyrazole (15 mg, 0.04 mmol), stannous chloride monohydrate (37 mg, 0.16 mmol), ethanol (2 mL), and concentrated hydrochloric acid (0.25 mL) were added to a 25 mL single-mouth bottle, and heated at 70° C. to react for three hours. After confirming completion of the reaction by TLC, the mixture was cooled to room temperature, added with 2N solution of hydrogen chloride (10 mL), and extracted with ethyl acetate (20 mL×3). The organic layers were combined, and washed with saturated sodium chloride (30 mL), and the solvent was dried with rotation under vacuum was to give the product of 2-(1-methyl-1H-pyrazole-4-yl)-2'-(trifluoromethoxy)-[1,1'-biphenylyl]-4-amine (white solid, 12.5 mg).

1-methyl-4-(4'-nitro-6-(trifluoromethoxy)-[1,1'-biphenyl]-2-yl)-1H-pyrazole (20 mg, 0.05 mmol), stannous chloride monohydrate (37 mg, 0.16 mmol), ethanol (2 mL), and concentrated hydrochloric acid (0.25 mL) were added to a 25 mL single-mouth bottle, and heated at 70° C. to react for three hours. After confirming completion of the reaction by TLC, the mixture was cooled to room temperature, added with 2N solution of hydrogen chloride (10 mL), and extracted with ethyl acetate (20 mL×3). The organic layers were combined, and washed with saturated sodium chloride (30 mL), and the solvent was dried with rotation under vacuum to give the product of 2'-(1-methyl-1H-pyrazole-4-yl)-6'-(trifluoromethoxy)-[1,1'-biphenylyl]-4-amine (white solid, 16 mg).

Step 6: 2-(4-((3-(2-(1-methyl-1H-pyrazole-4-yl)-2'-(trifluoromethoxy)-[1,1'-biphenyl]-4-yl)ureido) methyl)benzyl)methyl acetate and 2-(4-((3-(2'-(1-methyl-1H-pyrazole-4-yl)-6'-(trifluoromethoxy)-[1,1'-biphenyl]-4-yl)ureido) methyl)benzyl)methyl acetate 2-(1-methyl-1H-pyrazole-4-yl)-2'-(trifluoromethoxy)-[1,1'-biphenylyl]-4-amine (12.5 mg, 0.037 mmol), DCM (2 mL), and DIEA (9.5 mg, 0.074 mmol) were added to a 25 mL single-mouth bottle, and stirred for 5 min under ice bath, and then triphosgene (4.4 mg, 0.015 mmol) was added, and the reaction was continued under ice bath for 30 min, and then methyl 4-aminomethylphenylacetate (7.39 mg, 0.04 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleum ether:ethyl acetate=1:1) to give the product of 2-(4-((3-(2-(1-methyl-1H-pyrazole-4-yl)-2'-(trifluoromethoxy)-[1,1'-biphenyl]-4-yl)ureido) methyl)benzyl)methyl acetate (white solid, 12 mg), with a yield of 60.0%. $^1$H NMR (400 MHz, CDCl$_3$) δ 7.47 (s, 1H), 7.39-7.28 (m, 2H), 7.25-7.16 (m, 7H), 7.17-7.09 (m, 2H), 7.04 (s, 1H), 6.89 (s, 1H), 5.64 (s, 1H), 4.33 (s, 2H), 3.67 (s, 3H), 3.66 (s, 3H), 3.58 (s, 2H). MS (ESI) m/z: 539.2 (MH+).

2'-(1-methyl-1H-pyrazole-4-yl)-6'-(trifluoromethoxy)-[1,1'-phenyl]-4-amine (16 mg, 0.048 mmol), DCM (2 mL), and DIEA (13 mg, 0.096 mmol) were added to a 25 mL single-mouth bottle, and stirred for 5 min under ice bath, and then triphosgene (5.7 mg, 0.019 mmol) was added, and the reaction was continued under ice bath for 30 min, and then methyl 4-aminomethylphenylacetate (9.46 mg, 0.053 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleum ether:ethyl acetate=1:1) to give the product of 2-(4-((3-(2'-(1-methyl-1H-pyrazole-4-yl)-6'-(trifluoromethoxy)-[1,1'-biphenyl]-4-yl)ureido) methyl)benzyl) methyl acetate (yellow solid, 10 mg), with a yield of 38.7%. $^1$H NMR (400 MHz, CDCl$_3$) δ 7.46-7.28 (m, 4H), 7.25-7.12 (m, 6H), 7.11-7.01 (m, 3H), 6.78 (s, 1H), 5.47 (s, 1H), 4.38 (s, 2H), 3.69 (s, 3H), 3.68 (s, 3H) 3.61 (s, 2H). MS (ESI) m/z: 539.2 (MH+).

Step 7: 2-(4-((3-(2-(1-methyl-1H-pyrazol-4-yl)-2'-(trifluoromethoxy)-[1,1'-biphenyl]-4-yl))ureido)methyl)benzyl)acetic acid and 2-(4-((3-(2'-(1-methyl-1H-pyrazole-4-yl)-6'-(trifluoromethoxy)-[1,1'-biphenyl]-4-yl)ureido)methyl)benzyl)acetic acid 2-(4-((3-(2-(1-methyl-1H-pyrazole-4-yl)-2'-(trifluoromethoxy)-[1,1'-biphenyl]-4-yl)ureido)methyl)benzyl) methyl acetate (12 mg, 0.022 mmol), sodium hydroxide (1.92 mg, 0.04 mmol), ethanol (1 mL), and water (0.3 mL) were added to a 25 mL single-mouth bottle, and reacted at room temperature for 2 hours. After confirming completion of the reaction of materials by TLC, the mixture was adjusted to pH 3 with 2N hydrochloric acid, and extracted with ethyl acetate (10 mL×3), and the organic layer was concentrated in vacuo to give the product of 2-(4-((3-(2-(1-methyl-1H-pyrazol-4-yl)-2'-(trifluoromethoxy)-[1,1'-biphenyl]-4-yl))ureido)methyl)benzyl)acetic acid (white solid, 10 mg), with a yield of 85.6%. $^1$H NMR (400 MHz, CD$_3$OD) δ 7.61-7.60 (d, J=2.0 Hz, 1H), 7.43-7.42 (d, J=6.1 Hz, 1H), 7.39-7.33 (m, 1H), 7.32-7.25 (m, 6H), 7.23-7.22 (d, J=4.7 Hz, 2H), 7.15-7.13 (d, J=8.4 Hz, 1H), 6.97 (s, 1H), 4.40 (s, 2H), 3.75 (s, 3H), 3.59 (s, 2H). MS (ESI) m/z: 525.2 (MH+).

2-(4-((3-(2'-(1-methyl-1H-pyrazole-4-yl)-6'-(trifluoromethoxy)-[1,1'-biphenyl]-4-yl)ureido)methyl)benzyl) methyl acetate (10 mg, 0.018 mmol), sodium hydroxide (1.92 mg, 0.04 mmol), ethanol (1 mL), and water (0.3 mL) were added to a 25 mL single-mouth bottle, and reacted at room temperature for 2 hours. After confirming completion of the reaction of materials by TLC, the mixture was adjusted to pH 3 with 2N hydrochloric acid, and extracted with ethyl acetate (10 mL×3). The organic layer was concentrated in vacuo to give the product of 2-(4-((3-(2'-(1-methyl-1H-pyrazol-4-yl)-6'-(trifluoromethoxy)-[1,1'-biphenyl]-4-yl)ureido)methyl)benzyl)acetic acid (white solid, 5 mg), with a yield of 51.2%. $^1$H NMR (400 MHz, CD$_3$OD) δ 7.61 (d, J=1.9 Hz, 1H), 7.45-7.42 (t, J=10.9, 4.6 Hz, 1H), 7.37-7.33 (t, J=7.5 Hz, 1H), 7.32-7.25 (m, 7H), 7.22 (s, 1H), 7.15-7.14 (d, J=8.3 Hz, 1H), 6.97 (s, 1H), 4.39 (s, 2H), 3.73 (s, 3H), 3.57 (s, 2H). MS (ESI) m/z: 525.2 (MH+).

Example 23: 2-(4-((3-([1,1'-biphenyl]-4-yl)ureido) methyl)phenyl)acetic acid

I-23

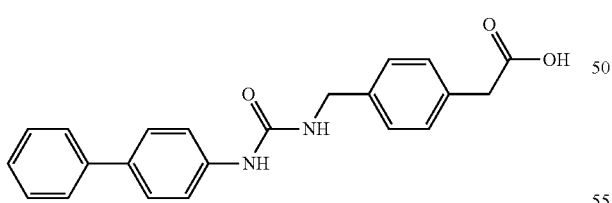

Step 1: methyl 4-aminomethylphenylacetate

P-methyl cyanobenzoate (200 mg, 1.14 mmol), methanol (2 mL), a small amount of Pd/C, and 2 drops of concentrated hydrochloric acid were added to a 25 mL single-mouth bottle under an hydrogen atmosphere at an atmospheric pressure; and stirred to react at room temperature for three hours. After confirming completion of the reaction by TLC, the mixture was filtered and concentrated in vacuo to give the product of methyl 4-aminomethylphenylacetate (white solid, 178 mg), with a yield of 74.2%. $^1$H NMR (400 MHz, DMSO) δ 8.22 (s, 2H), 7.44 (d, J=8.1 Hz, 2H), 7.30 (d, J=8.1 Hz, 2H), 3.98 (s, 2H), 3.71 (s, 2H), 3.61 (s, 3H). MS (ESI) m/z: 180.1 (MH+).

Step 2: 2-(4-((3-([1,1'-biphenylyl-4-yl]ureido) methyl)benzyl)methyl acetate 4-(aminomethyl) methyl phenylacetate (76 mg, 0.45 mmol), dichloromethane (2 mL), and DIEA (116 mg, 0.90 mmol) were added to a 25 mL single-mouth bottle, and stirred for 5 min under ice bath, and then triphosgene (44 mg, 0.15 mmol) was added, and the reaction was continued under ice bath for 30 min, and then 4-biphenylamine (80 mg, 0.45 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleum ether:ethyl acetate=1:1) to give the product of 2-(4-((3-([1,1'-biphenylyl-4-yl]ureido)methyl)benzyl)methyl acetate (white solid, 60 mg), with a yield of 37.9%. $^1$H NMR (400 MHz, CDCl$_3$) δ 7.55-7.50 (m, 3H), 7.45-7.39 (m, 2H), 7.37-7.30 (m, 2H), 7.27-7.25 (m, 2H), 7.22-7.20 (m, 3H), 4.40 (s, 2H), 3.68 (s, 3H), 3.61-3.60 (d, J 2.6 Hz, 2H). MS (ESI) m/z: 374.9 (MH+).

Step 3: 2-(4-((3-([1,1'-biphenylyl-4-yl]ureido) methyl)benzyl)acetic acid 2-(4-((3 ([1,1'-biphenylyl-4-yl)ureido)methyl)benzyl) methyl acetate (60 mg, 0.16 mmol), sodium hydroxide (19 mg 0.48 mmol), ethanol (2 mL), and H$_2$O (1 mL) were added to a 25 mL single-mouth bottle, and reacted at room temperature for 2 hours. After confirming completion of the reaction of materials by TLC, the mixture was adjusted to pH 3 with 2N hydrochloric acid, and extracted with ethyl acetate (10 mL×3), and the organic layer was concentrated in vacuo to give the product of 2-(4-((3([1,1'-biphenylyl-4-yl]ureido)methyl)benzyl)acetic acid (white solid, 40 mg), with a yield of 87.7%. $^1$H NMR (400 MHz, DMSO) δ 8.68 (s, 1H), 7.60-7.58 (d, J=7.2 Hz, 2H), 7.54-7.52 (d, J 8.8 Hz, 2H), 7.49-7.47 (d, J 8.8 Hz, 2H), 7.42-7.48 (t, J=7.7 Hz, 2H), 7.29-7.27 (t, J 7.3 Hz, 1H), 7.25-7.21 (q, J 6.3 Hz, 3H), 7.17 (s, 1H), 6.64 (s, 1H), 4.27 (d, J=5.8 Hz, 2H), 4.18 (d, J=4.8 Hz, 1H), 3.52 (s, 2H). MS (ESI) m/z: 361.0 (MH+).

Example 24: 2-(4-((3-(2,6-dichloro-2'-(trifluoromethoxy)-[1,1'-biphenyl]-4-yl)ureido) methyl) phenyl)propanoic acid

I-24

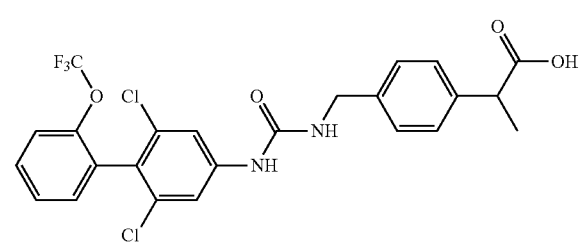

Step 1: methyl 2-(4-cyanobenzyl) isopropanoate

Methyl p-cyanophenylacetate (300 mg, 0.86 mmol), and tetrahydrofuran (2 mL) were added to a 25 mL single-mouth bottle, and stirred for 10 min under ice bath, then NaH (81 mg, 1.02 mmol, 60%) was added, and the reaction was continued under ice bath for 10 min. Then iodomethane (243 mg, 0.86 mmol) was added, and the reaction was continued for 1 hour while stirring, and after completion of the reaction, the reaction was quenched with water. The reaction mixture was adjusted to pH 3 with 2M hydrochloric acid solution, and extracted with ethyl acetate (10 mL×3). The organic layers were combined, washed with saturated brine, dried over anhydrous sodium sulfate, and filtered, and then the filtrate was concentrated in vacuo to obtain a crude product. The crude product was passed through a column (ethyl acetate:petroleum ether=1:1) to give the product (white oil, 190 mg), with a yield of 58.6%. $^1$H NMR (400 MHz, CDCl$_3$) δ 7.62 (d, J 8.3 Hz, 2H), 7.41 (d, J 8.1 Hz, 2H), 3.78 (q, J 7.1 Hz, 1H), 3.67 (s, 3H), 1.51 (d, J 7.2 Hz, 3H). MS (ES) m/z: 190.0 (MH+).

Step 2: 2-(4-aminomethylbenzyl)methyl isopropylate 2-(4-cyanobenzyl)propanoate methyl ester (190 mg, 1.0 mmol), methanol (10 mL), tetrahydrofuran (2 mL), aqueous ammonia (0.5 mL, 28%) and Raney Ni (100 mg) were added to a 25 mL single-mouth bottle, and the reaction mixture was stirred at room temperature for 30 min, and filtered over celite, and the solvent was dried with rotation under vacuum to give the anhydrous solid product (140 mg), with a yield of 72.9%. MS (ES) m/z: 194.1 (MH+).

Step 3: 2-(4-((3-(2,6-dichloro-2'-(trifluoromethyl)-[1,1'-biphenyl]-4-yl)ureido)methyl)phenyl) methyl isopropylate 2,6-dichloro-2'-(trifluoromethoxy)-[1,1'-biphenylyl]-4-amine (100 mg, 0.31 mmol), DCM (4 mL), and DIEA (120 mg, 0.93 mmol) were added to a 25 mL single-mouth bottle, and stirred under ice bath for 10 min, and then triphosgene (35 mg, 0.11 mmol) was added, and the reaction was continued under ice bath for 30 min, and then 2-(4-aminomethylbenzyl)methyl isopropylate (71 mg, 0.37 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (dichloromethane:methanol=20:1) to give the product (white solid, 65 mg), with a yield of 38.7%. $^1$H NMR (400 MHz, CDCl$_3$) δ 7.99 (d, J=5.7 Hz, 1H), 7.48-7.41 (m, 1H), 7.41 (s, 2H), 7.33 (t, J=7.6 Hz, 2H), 7.21-7.10 (m, 5H), 6.11-6.01 (m, 1H), 4.26 (d, J=5.6 Hz, 2H), 3.69 (d, J 7.2 Hz, 1H), 3.61 (s, 3H), 1.44 (d, J=7.2 Hz, 3H). MS (ES) m/z: 540.7 (MH+).

Step 4: 2-(4-((3-(2,6-dichloro-2'-(trifluoromethoxy)-[1,1'-biphenyl]-4-yl)ureido) methyl)phenyl) isopropyl acid 2-(4-((3-(2,6-dichloro-2'-(trifluoromethyl)-[1,1'-biphenyl]-4-yl)ureido) methyl)phenyl)methyl isopropylate (65 mg, 0.12 mmol), lithium hydroxide monohydrate (15 mg, 0.36 mmol), ethanol (2 mL), tetrahydrofuran (2 mL), and water (0.3 mL) were added to a 25 mL single-mouth bottle, and reacted at room temperature for 2 hours. After confirming completion of the reaction of materials by TLC, the mixture was adjusted to pH 3 with 2N hydrochloric acid, and extracted with ethyl acetate (10 mL×3). The organic layer was concentrated in vacuo to give the product (white solid, 35 mg), with a yield of 56.4%. $^1$H NMR (400 MHz, CD$_3$OD) δ 7.58 (s, 2H), 7.50 (td, J=8.1, 1.4 Hz, 1H), 7.43-7.35 (m, 2H), 7.31-7.23 (m, 5H), 4.37 (s, 2H), 3.69 (q, J=7.1 Hz, 1H), 1.43 (d, J=7.1 Hz, 3H). MS (ES) m/z: 526.8 (MH+).

Example 25: 2-(4-((3-(2,6-dichloro-2'-(trifluoromethoxy)-[1,1'-biphenyl]-4-yl)ureido)methyl)phenyl)-2,2-difluoroacetic acid

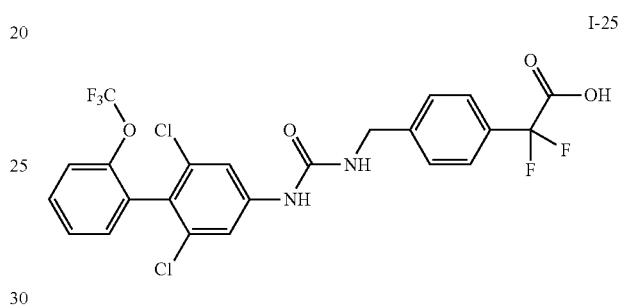

I-25

Step 1: 2-(4-cyanobenzyl)-2,2-ethyl difluoroacetate 4-iodobenzonitrile (940 mg, 4.21 mmol), DMSO (10 mL), 2-bromo-2,2-ethyl difluoroacetate (940 mg, 4.63 mmol), and copper powder (539 mg) were added to a 25 mL single-mouth bottle, heated to react at 65° C. for 18 hours, and cooled to room temperature. Then water (40 mL) was added, and the mixture was extracted with ethyl acetate (20 mL×3). The organic layers were combined, concentrated in vacuo and separated by a silica gel column (petroleum ether:acetic acid ester=200:1) to give the product of 2-(4-cyanobenzyl)-2,2-ethyl difluoroacetate (anhydrous liquid, 670 mg), with a yield of 70.8%. $^1$H NMR (400 MHz, CDCl$_3$) δ 7.75 (q, J=8.5 Hz, 4H), 4.31 (q, J=7.1 Hz, 2H), 1.30 (t, J=7.1 Hz, 3H).

Step 2: 2-(4-(aminomethyl)phenyl)-2,2-ethyl difluoroacetate

A small amount of Raney Ni, 2-(4-cyanobenzyl)-2,2-ethyl difluoroacetate (200 mg), absolute ethanol (4 mL), and a solution of hydrochloric acid in diethyl ether (0.5 mL) were added to a 25 mL single-mouth bottle. The hydrogen gas was introduced to enable the mixture to react at room temperature for 10 minutes. After confirming completion of the reaction of materials by TLC, the mixture was filtered by celite and concentrated in vacuo, and the crude product was separated by a column dichloromethane:methanol=10:1) to give the product of 2-(4-(aminomethyl)phenyl)-2,2-ethyl difluoroacetate (orange solid, 100 mg), with a yield of 49.2%. MS (ESI) m/z: 230.1 (MH+).

Step 3: 2-(4-((3-(2,6-chloro-2'-(trifluoromethyl)-[1,1'-biphenyl]-4-yl)ureido)methyl)phenyl)-2,2-ethyl difluoroacetate 2,6-dichloro-2'-(trifluoromethoxy)-[1,1'-biphenylyl]-4-amine (100 mg, 0.31 mmol), DCM (4 mL), and DIEA (120 mg, 0.93 mmol) were added to a 25 mL single-mouth bottle, and stirred under ice bath for 10 min, and then triphosgene (35 mg, 0.11 mmol) was added, and the reaction was continued for 30 minutes under ice bath, and then 2-(4-(aminomethyl)phenyl)-2,2-ethyl difluoroacetate (85 mg, 0.37 mmol) was dissolved in DMF (1 mL) and added, and the reaction was continued under ice bath for 30 min. H$_2$O (10 mL) was added, and the mixture was washed with saturated ammonium chloride, extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (dichloromethane:methanol=20:1) to give the product (white solid, 30 mg), with a yield of 16.8%. H$^1$ NMR (400 MHz, CDCl$_3$) δ 7.82 (s, 1H), 7.50 (d, J=7.9 Hz, 2H), 7.46 (s, 2H), 7.45-7.40 (m, 1H), 7.36-7.28 (m, 5H), 7.20 (d, J=7.0 Hz, 1H), 6.09 (s, 1H), 4.38 (d, J=5.1 Hz, 2H), 4.25 (q, J=7.1 Hz, 2H), 1.29-1.25 (m, 4H). MS (ESI) m/z: 574.7 (M−1).

Step 4: 2-(4-((3-(2,6-chloro-2'-(trifluoromethyl)-[1,1'-biphenyl]-4-yl)ureido)methyl)phenyl)-2,2-difluoroacetic acid 2-(4-((3-(2,6-chloro-2'-(trifluoromethyl)-[1,1'-biphenyl]-4-yl)ureido)methyl)phenyl)-2,2-ethyl difluoroacetate (30 mg, 0.035 mmol), lithium hydroxide (4.27 mg, 0.1 mmol), ethanol (2 mL), and water (0.5 mL) were added to a 25 mL single-mouth bottle, and reacted at room temperature for 2 hours. After confirming completion of the reaction of materials by TLC, the mixture was adjusted to pH 3 with 2N hydrochloric acid, and extracted with ethyl acetate (10 mL×3). The organic layer was concentrated in vacuo to give the product of 2-(4-((3-(2,6-chloro-2'-(trifluoromethyl)-[1,1'-biphenyl]-4-yl)ureido)methyl)phenyl)-2,2-difluoroacetic acid (white solid, 25 mg), with a yield of 71.4%. $^1$H NMR (400 MHz, CD$_3$OD) δ 7.62-7.55 (m, 4H), 7.55-7.49 (m, 1H), 7.49-7.43 (m, 3H), 7.40 (t, J=7.6 Hz, 2H), 7.30 (t, J=10.1 Hz, 1H), 4.46 (s, 2H). MS (ESI) m/z: 548.8 (MH+).

Example 26: 2-(4-((3-(2,6-dichloro-2'-(trifluoromethoxy)-[1,1'-biphenyl]-4-yl)ureido)methyl)phenoxy)acetic acid

I-26

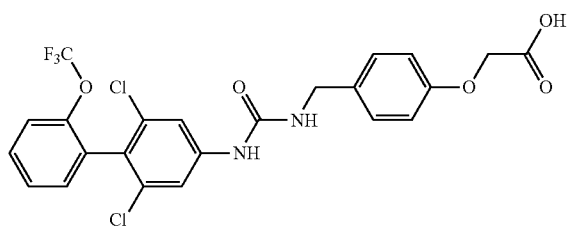

Step 1: 2-(4-cyanophenoxyl)methyl acetate 4-cyanophenol (1.32 g, 11 mmol), 2-methyl bromoacetate (2 g, 13 mmol), potassium carbonate (4.15 g, 33 mmol), and acetonitrile (25 mL) were added to a 50 mL single-mouth bottle one by one, and heated to react at 70° C. for 1.5 hours. After completion of the reaction, the reaction mixture was cooled, and filtered, and the solvent was dried with rotation under vacuum to give the product of 2-(4-cyanophenoxyl) methyl acetate (white solid, 2.28 g), with a yield of 100%. H$^1$ NMR (400 MHz, CDCl$_3$) δ 7.62-7.60 (d, J=8.9 Hz, 2H), 6.97-6.96 (d, J=8.9 Hz, 2H), 4.69 (s, 2H), 3.82 (s, 3H).

Step 2: 2-(4-(aminomethyl)phenoxyl)methyl acetate 2-(4-cyanophenoxyl)methyl acetate (500 mg, 2.62 mmol), methanol (10 mL), and concentrated hydrochloric acid (1 mL) were added to a 25 mL single-mouth bottle, and then Pd/C (50 mg) was added. The obtained mixture reacted for two hours at room temperature under hydrogen environment at an atmospheric pressure, and filtered over celite, and then the filtrate was concentrated in vacuo to give the product of 2-(4-(aminomethyl)phenoxyl)methyl acetate (yellow solid, 560 mg), with a yield of 92.7%. H$^1$ NMR (400 MHz, DMSO) δ 8.28 (s, 3H), 7.42-7.40 (d, J=8.5 Hz, 2H), 6.98-6.96 (d, J=8.6 Hz, 2H), 4.83 (s, 2H), 3.94 (s, 2H), 3.69 (s, 3H).

Step 3: 2-(4-((3-(2,6-dichloro-2'-(trifluoromethoxy)-[1,1'-biphenyl]-4-yl)ureido)methyl)phenoxyl)ethyl acetate 2,6-dichloro-2'-(trifluoromethoxy)-[1,1'-biphenylyl]-4-amine (60 mg, 0.1 mmol), DCM (4 mL), and DIEA (72 mg, 0.56 mmol) were added to a 25 mL single-mouth bottle, and stirred under ice bath for 5 minutes, and then triphosgene (22 mg, 0.074 mmol) was added, and the reaction was continued under ice bath for 30 min, and then 2-(4-(aminomethyl)phenoxyl)methyl acetate (44 mg, 0.20 mmol) was added, and the reaction was continued under ice bath for 30 min, then at room temperature overnight. H$_2$O (10 mL) was added, and the mixture was extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (developing solvent petroleum ether:ethyl acetate=1:1) to give the product of 2-(4-((3-(2,6-dichloro-2'-(trifluoromethoxy)-[1,1'-biphenyl]-4-yl)ureido)methyl)phenoxyl)ethyl acetate (white solid, 38 mg), with a yield of 37.6%. $^1$H NMR (400 MHz, CDCl$_3$) δ 7.76 (s, 1H), 7.49-7.37 (m, 3H), 7.38-7.30 (m, 2H), 7.21-7.19 (d, J=6.6 Hz, 1H), 7.10-7.07 (d, J=8.4 Hz, 2H), 6.75-6.73 (d, J=8.5 Hz, 2H), 5.89 (s, 1H), 4.58 (s, 2H), 4.22 (d, J=3.6 Hz, 2H), 3.78 (s, 3H). MS (ESI) m/z: 541.0 (M−1).

Step 4: 2-(4-((3-(2,6-dichloro-2'-(trifluoromethoxy)-[1,1'-biphenyl]-4-yl)ureido)methyl)phenoxyl) acetic acid 2-(4-((3-(2,6-dichloro-2'-(trifluoromethoxy)-[1,1'-biphenyl]-4-yl)ureido)methyl)phenoxyl)ethyl acetate (38 mg, 0.07 mmol), lithium hydroxide (8.8 mg, 0.21 mmol), ethanol (1 mL), and water (0.3 mL) were added to a 25 mL single-mouth bottle, and reacted at room temperature for 2 hours. After confirming completion of the reaction of materials by TLC, the mixture was adjusted to pH 3 with 2N hydrochloric acid, and extracted with ethyl acetate (10 mL×3), and the organic layer was concentrated in vacuo to give the product of 2-(4-((3-(2,6-dichloro-2'-(trifluoromethoxy)-[1,1'-biphenyl]-4-yl)ureido) methyl)phenoxyl) acetic acid (white solid, 34 mg), with a yield of 91.2%. $^1$H NMR (400 MHz, CD$_3$OD) δ 7.58 (s, 2H), 7.52 (t, J=7.1 Hz, 1H), 7.41 (dd, J=15.3, 7.8 Hz, 2H), 7.28 (t, J=7.1 Hz, 3H), 6.95-6.87 (m, 2H), 4.67 (d, J=22.3 Hz, 2H), 4.33 (s, 2H), 3.77 (s, 1H). MS (ESI) m/z: 529.0 (M−1).

Example 27: 2-(4-((3-(2,6-dichloro-2'-(trifluoromethoxy)-[1,1'-biphenyl]-4-yl)-3-methylureido)methyl)phenyl)acetic acid

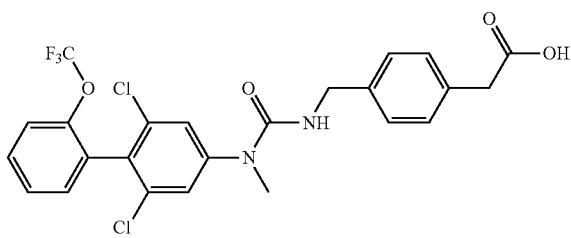

I-27

Step 1: 2,6-dichloro-N-methyl-2'-(trifluoromethoxy)-[1,1'-biphenyl]-4-amine 2,6-dichloro-2'-(trifluoromethoxy)-[1,1'-biphenylyl]-4-amine (100 mg, 0.31 mmol), tetrahydrofuran (1 mL), paraformaldehyde (17 mg, 0.45 mmol) and acetic acid (2 drops) were added to a 25 mL single-mouth bottle, and stirred at room temperature for 2 h, and then sodium cyanoborohydride (30 mg, 0.9 mmol) was added, and the reaction was continued at room temperature overnight. After completion of reaction, $H_2O$ (20 mL) was added, and the mixture was extracted with ethyl acetate (20 mL×3). The organic layers were combined, and washed with saturated sodium chloride (30 mL), and the solvent was dried with rotation under vacuum, and the crude product was passed through a silica gel column (petroleumether:ethylacetate=20:1) to give the product of 2,6-dichloro-N-methyl-2'-(trifluoromethoxy)-[1,1'-biphenyl]-4-amine (white oil, 45 mg), with a yield of 26.9%. $^1$H NMR (400 MHz, $CDCl_3$) δ 7.47-7.40 (m, 1H), 7.39-7.32 (m, 2H), 7.31-7.27 (m, 1H), 6.63 (s, 2H), 2.85 (s, 3H). MS (ESI) m/z: 336.0 (MH+).

Step 2: 2-(4-((3-(2,6-dichloro-2'-(trifluoromethyl)-[1,1'-biphenyl]-4-yl)-3-methylureido)meth yl)phenyl)methyl acetate 2,6-dichloro-N-methyl-2'-(trifluoromethoxy)-[1,1'-biphenyl]-4-amine (45 mg, 0.14 mmol), dichloromethane (4 mL), and DIEA (54 mg, 0.42 mmol) were added to a 25 mL single-mouth bottle, and stirred for 5 min under ice bath, and then triphosgene (16 mg, 0.05 mmol) was added, and the reaction was continued under ice bath for 30 min, and then dichloromethane (10 mL) was added. The mixture was washed with saturated ammonium chloride (10 mL), the solvent was dried with rotation under vacuum in the organic layer, and the obtained product was vacuum dried. The resulting product was dissolved in tetrahydrofuran (2 mL), then methyl 4-aminomethylphenylacetate (30 mg, 0.14 mmol), and DIEA (54 mg, 0.28 mmol) were added to react at 60° C. overnight. The obtained mixture was concentrated in vacuo to remove the solvent, and the crude product was separated by preparative thin layer chromatography (petroleumether:ethylacetate=2:1) to give the product of 2-(4-((3-(2,6-dichloro-2'-(trifluoromethyl)-[1,1'-biphenyl]-4-yl)-3-methylureido)methyl)phenyl)methyl acetate (white solid, 52 mg), with a yield of 72.2%. MS (ESI) m/z: 541.1 (MH+).

Step 3: 2-(4-((3-(2,6-dichloro-2'-(trifluoromethyl)-[1,1'-biphenyl]-4-yl)-3-methylureido)methyl)phenyl)acetic acid 2-(4-((3-(2,6-dichloro-2'-(trifluoromethyl)-[1,1'-biphenyl]-4-yl)-3-methylureido) methyl)phenyl)methyl acetate (50 mg, 0.09 mmol), sodium hydroxide (11 mg, 0.27 mmol), ethanol (1 mL), and water (0.3 mL) were added to a 25 mL single-mouth bottle, and reacted for 2 hours at room temperature. After confirming completion of the reaction of materials by TLC, the mixture was adjusted to pH 3 with 2N hydrochloric acid, and extracted with ethyl acetate (10 mL×3). The organic layer was concentrated in vacuo to give the product (white solid, 42 mg), with a yield of 86.2%. $^1$H NMR (400 MHz, $CD_3OD$) δ 7.55 (t, J=7.1 Hz, 1H), 7.48 (s, 2H), 7.44 (t, J=7.6 Hz, 2H), 7.33-7.21 (m, 5H), 4.36 (s, 2H), 3.57 (s, 2H), 3.31 (s, 3H). MS (ESI) m/z: 526.7 (MH+).

Example 28: 2-(4-((3-(2,6-dichloro-2'-(trifluoromethoxy)-[1,1'-biphenyl]-4-yl)-1-methylureido)methyl)phenyl)acetic acid

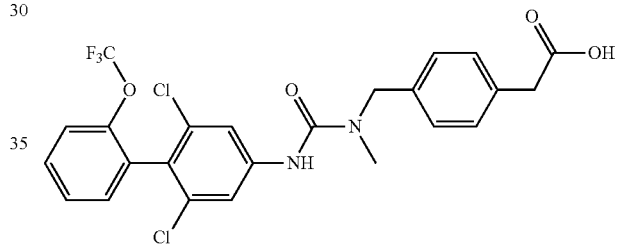

I-28

Step 1: 2-(4-(bromomethyl)benzyl)acetic acid p-methylphenylacetic acid (3.88 g, 25.9 mmol), NBS (4.83 g, 27.2 mmol), AIBN (42 mg, 0.26 mmol), and carbon tetrachloride (50 mL) were added to a 100 mL single-mouth bottle, and reacted at 90° C. for 4 hours. The mixture was concentrated in vacuo to remove the solvent under a reduced pressure, and was passed through a column (ethyl acetate: petroleum ether=1:4) to give the product (white solid, 2.28 g), with a yield of 40.8%. $^1$H NMR (400 MHz, DMSO) δ 12.31 (s, 1H), 7.25 (d, J=7.6 Hz, 2H), 7.11 (d, J=7.5 Hz, 2H), 4.56 (s, 2H), 3.44 (s, 2H). MS (ESI) m/z: 228.9 (MH+)

Step 2: 2-(4-((methylamino)methyl)phenyl)acetic acid

A solution of methylamine in ethanol (0.5 mL) was added to a 25 mL single-mouth bottle. Then 2-(4-(bromomethyl)phenyl)acetic acid (1 g, 4.4 mmol) was weighed and dissolved in dichloromethane (4 mL), and added dropwise to the reaction mixture at room temperature. And after addition, the reaction was continued at room temperature for 1 hour, and reaction mixture was concentrated in vacuo to remove the solvent, and the product was used in the next reaction directly. MS (ESI+) m/z: 180.1 ((MH+).

Step 3: 2-(4-((methylamino)methyl)benzyl)ethyl acetate

The 2-(4-((methylamino)methyl)benzyl)acetic acid obtained in step 2 was dissolved in methanol (5 mL), then added with thionyl chloride (0.5 mL) and the obtained mixture was allowed to react at room temperature for half an hour. The reaction mixture was concentrated in vacuo to remove the solvent. Then water (20 mL) was added, and the mixture was adjusted to pH 8 with saturated sodium carbonate, extracted with ethyl acetate (20 mL×3), and dried over anhydrous sodium sulfate, and the organic layer was concentrated in vacuo and passed through a silica gel column (petroleumether:ethylacetate=10:1-4:1) to give the product (white solid, 120 mg). (ESI+) m/z: 194.1 ((MH+).

Step 4: 2-(4-((3-(2,6-dichloro-2'-(trifluoromethyl)-[1,1'-biphenyl]-4-yl)-1-methylureido)methyl)phenyl)ethyl acetate 2,6-dichloro-2'-(trifluoromethoxy)-[1,1'-biphenylyl]-4-amine (100 mg, 0.31 mmol), dichloromethane (5 mL), and DIEA (120 mg, 0.93 mmol) were added to a 25 mL single-mouth bottle, and stirred under ice bath for 10 min, and then triphosgene (35 mg, 0.11 mmol) was added, and the reaction was continued under ice bath for 30 min, and then 2-(4-((methylamino)methyl)phenyl)ethyl acetate (72 mg, 0.37 mmol) was added, and the reaction was continued under ice bath for 30 min, then at room temperature overnight. H$_2$O (10 mL) was added, and the mixture was washed with saturated ammonium chloride, extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (dichloromethane:methanol=20:1) to give the product (white solid, 70 mg), with a yield of 41.9%. $^1$H NMR (400 MHz, CDCl$_3$) δ 7.51 (s, 2H), 7.48-7.42 (m, 1H), 7.36 (t, J=7.0 Hz, 2H), 7.33-7.28 (m, 2H), 7.28-7.26 (m, 3H), 6.43 (s, 1H), 4.58 (s, 2H), 3.70 (s, 3H), 3.64 (s, 2H), 3.05 (s, 3H). (ESI+) m/z: 540.7 ((MH+).

Step 5: 2-(4-((3-(2,6-dichloro-2'-(trifluoromethyl)-[1,1'-biphenyl]-4-yl)-1-methylureido)methyl)phenyl)acetic acid 2-(4-((3-(2,6-dichloro-2'-(trifluoromethyl)-[1,1'-biphenyl]-4-yl)-1-methylureido) methyl)phenyl)ethyl acetate (73 mg, 0.13 mmol), sodium hydroxide (16 mg, 0.39 mmol), ethanol (2 mL), tetrahydrofuran (1 mL), and water (0.3 mL) were added to a 25 mL single-mouth bottle, and reacted at room temperature for 2 hours. The ethanol was spun off under an increased pressure, water (5 mL) was added, and the mixture was adjusted to pH 3 with 2N hydrochloric acid, and extracted with ethyl acetate (10 mL×3). The organic layer was concentrated in vacuo to give the product (white solid, 45 mg), with a yield of 61.6%. $^1$H NMR (400 MHz, CD$_3$OD) δ 7.63 (s, 2H), 7.48 (t, J=7.8 Hz, 1H), 7.42-7.32 (m, 2H), 7.29-7.18 (m, 5H), 4.56 (s, 2H), 3.56 (s, 2H), 2.94 (s, 3H). (ESI+) m/z: 526.8 ((MH+).

Example 29: 2-(6-((3-(2,6-dichloro-2'-(trifluoromethoxy)-[1,1'-biphenyl]-4-yl)ureido)methyl)pyridin-3-yl)acetic acid

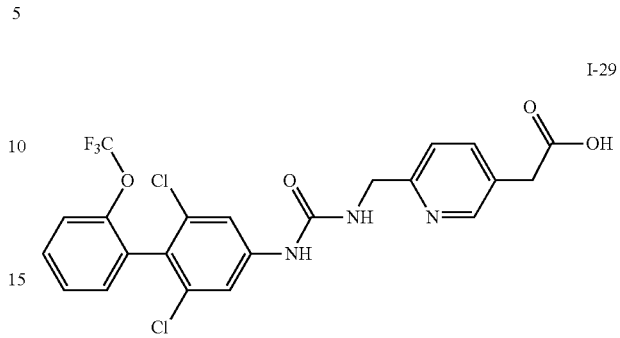

I-29

Step 1: 2-(6-chloropyridine-3-yl)ethyl acetate 2-(6-chloropyridin-3-yl)acetic acid (4 g, 22.4 mmol), ethanol (20 mL) and concentrated sulfuric acid (0.4 mL) were added to a 100 mL single-mouth bottle, and heated to 90° C. to react overnight. After reaction, the mixture was cooled to room temperature, neutralized with saturated sodium bicarbonate, and extracted with ethyl acetate. The organic layers were combined, the solvent was dried with rotation under vacuum under an increased pressure, and the obtained product separated by a silica gel column (petroleumether:ethylacetate=5:1) to give the product (colorless oil, 3.75 g), with a yield of 87.2%. $^1$H NMR (400 MHz, CDCl$_3$) δ 8.28 (d, J=1.5 Hz, 1H), 7.61 (dd, J=8.2, 2.1 Hz, 1H), 7.29 (d, J=8.2 Hz, 1H), 4.16 (q, J=7.1 Hz, 2H), 3.59 (s, 2H), 1.25 (t, J=7.1 Hz, 3H).

Step 2: 2-(6-cyanopyridine-3-yl)ethyl acetate 2-(6-chloropyridine-3-yl)ethyl acetate (2 g, 10.8 mmol), zinc cyanide (1.88 g, 0.5 mmol), tetrakis(triphenylphosphine)palladium (1.2 g, 0.054 mmol), and DMF (10 mL) were added to a 25 mL microwave tube, and reacted at 155° C. for 2 hours and then the reaction mixture was separated by a silica gel column (petroleum ether:ethyl acetate=10:1-5:1) to give the product (white solid, 930 mg), with a yield of 48.9%. MS (ESI) m/z: 189.0 (M+1).

Step 3: 2-(6-(aminomethyl)pyridine-3-yl)ethyl acetate 2-(6-cyanopyridine-3-yl)ethyl acetate (200 mg), methanol (2 mL), concentrated hydrochloric acid (10 mL), and Pd/C (20 mg) were added to a 25 mL single-mouth bottle. The hydrogen gas was introduced to enable the mixture to react at room temperature for 10 minutes. After confirming completion of the reaction of materials by TLC, the mixture was filtered by celite, and the filtrate was concentrated under a reduced pressure, which is used for the next reaction directly. MS (ESI) m/z: 195 (M+1).

Step 4: 2-(6-((3-(2,6-dichloro-2'-(trifluoromethyl)-[1,1'-biphenyl]-4-yl)ureido)methyl)pyridin-3-yl)ethyl acetate 2,6-dichloro-2'-(trifluoromethoxy)-[1,1'-biphenylyl]-4-amine (100 mg, 0.3 mmol), DCM (4 mL), and DIEA (120 mg, 0.93 mmol) were added to a 25 mL single-mouth bottle, and stirred for 10 min under ice bath, and then triphosgene (35 mg, 0.11 mmol) was added, and the reaction was continued under ice bath for 10 min, and then 2-(6-(aminomethyl)pyridine-3-yl)methyl acetate (57 mg, 0.37 mmol) was added, and the reaction was continued under ice bath for 30 min. H₂O (10 mL) was added, and the mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (dichloromethane:methanol=20:1) to give the product (white solid, 20 mg), with a yield of 11.9%.

Step 5: 2-(6-((3-(2,6-dichloro-2'-(trifluoromethyl)-[1,1'-biphenyl]-4-yl)ureido)methyl)pyridine-3-yl)acetic acid 2-(6-((3-(2,6-dichloro-2'-(trifluoromethyl)-[1,1'-biphenyl]-4-yl)ureido)methyl) pyridine-3-yl)ethyl acetate (20 mg, 0.037 mmol), lithium hydroxide (4.54 mg, 0.11 mmol), ethanol (1 mL), and water (0.3 mL) were added to a 25 mL single-mouth bottle, and reacted for 2 hours at room temperature. After confirming completion of the reaction of materials by TLC, the mixture was adjusted to pH 3 with 2N hydrochloric acid, and extracted with ethyl acetate (10 mL×3). The organic layer was concentrated in vacuo to give the product (white solid, 15 mg), with a yield of 78.9%. ¹H NMR (400 MHz, CD₃OD) δ 8.42 (s, 1H), 7.76 (dd, J=8.0, 1.8 Hz, 1H), 7.60 (s, 2H), 7.55-7.48 (m, 1H), 7.45-7.36 (m, 3H), 7.29 (dd, J=7.6, 1.7 Hz, 1H), 4.51 (s, 2H), 3.65 (s, 2H). MS (ESI) m/z: 513.8 (M+1).

Example 30: 2-(6-((3-(2,6-dichloro-2'-(trifluoromethoxy)-[1,1'-biphenyl]-4-yl)ureido)methyl)pyridin-3-yl)propanoic acid

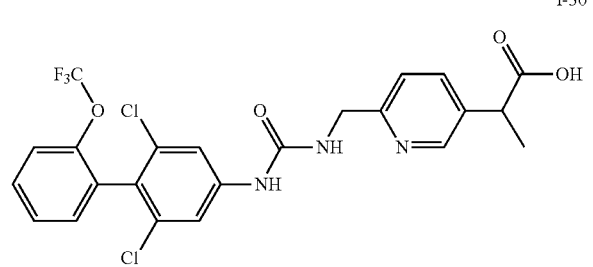

I-30

Step 1: 2-(6-cyanopyridine-3-yl)ethyl isopropanoate 2-(6-cyanopyridine-3-yl)ethyl acetate (300 mg, 1.7 mmol) and tetrahydrofuran (2 mL) were added to a 25 mL dried three-necked bottle, and stirred for 5 minutes under ice bath, and then NaH (75 mg, 1.87 mmol) was added in batches to continue to stir for 15 min under ice bath. In addition, methyl iodide (241 mg, 1.7 mmol) was taken and diluted with tetrahydrofuran (1 mL), and added to the reaction mixture, and the reaction was continued under ice bath for 30 min. After completion of the reaction, the reaction was quenched with water, the reaction mixture was extracted with ethyl acetate, and the organic layers were combined, the solvent was dried with rotation under a reduced pressure, and separated by a silica gel column (petroleum ether:ethyl acetate=5:1) to give the product (anhydrous oil, 140 mg), with a yield of 43.5%. MS (ESI) m/z: 205.1 (M+1).

Step 2: 2-(6-(aminomethyl)pyridine-3-yl)ethyl isopropanoate 2-(6-cyanopyridine-3-yl)ethyl isopropylate (140 mg), methanol (2 mL), concentrated hydrochloric acid (5 drops) and Pd/C (15 mg) were added to a 25 mL single-mouth bottle, and hydrogen gas was introduced to enable them obtained mixture to react at room temperature for 30 minutes. After confirming completion of the reaction of materials by TLC, the mixture was filtered by celite, and the filtrate was concentrated under a reduced pressure, which was used in the next reaction directly. MS (ESI) m/z: 209.1 (M+1).

Step 3: 2-(6-((3-(2,6-dichloro-2'-(trifluoromethyl)-[1,1'-biphenyl]-4-yl)ureido)methyl)pyridine-3-yl)ethyl isopropanoate 2,6-dichloro-2'-(trifluoromethoxy)-[1,1'-biphenylyl]-4-amine (100 mg, 0.31 mmol), DCM (4 mL), and DIEA (120 mg, 0.93 mmol) were added to a 25 mL single-mouth bottle, and stirred under ice bath for 10 minutes, and then triphosgene (35 mg, 0.11 mmol) was added, and the reaction was continued under ice bath for 30 min, and then 2-(6-(aminomethyl)pyridine-3-yl)ethyl isopropanoate (77 mg, 0.37 mmol) was added and the reaction was continued under ice bath for 30 min, then at room temperature overnight. H₂O (10 mL) was added, and the mixture was washed with saturated ammonium chloride, and extracted with dichloromethane (10 mL×3), and the organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (dichloromethane:methanol=20:1) to give the product (white solid, 10 mg), with a yield of 5.81%. MS (ESI) m/z: 555.8 (M+1).

Step 4: 2-(6-((3-(2,6-dichloro-2'-(trifluoromethyl)-[1,1'-biphenyl]-4-yl)ureido)methyl)pyridine-3-yl)isopropyl acid 2-(6-((3-(2,6-dichloro-2'-(trifluoromethyl)-[1,1'-biphenyl]-4-yl)ureido)methyl) pyridine-3-yl)ethyl acetate (10 mg, 0.018 mmol), lithium hydroxide (2.17 mg, 0.053 mmol), ethanol (1 mL) and water (0.3 mL) were added to a 25 mL single-mouth bottle, and reacted for 2 hours at room temperature. After confirming completion of the reaction of materials by TLC, the mixture was adjusted to pH 3 with 2N hydrochloric acid, and extracted with ethyl acetate (10 mL×3). The organic layer was concentrated in vacuo to give the product (white solid, 5 mg), with a yield of 52.6%. ¹H NMR (400 MHz, CD₃OD) δ 8.46 (s, 1H), 7.81 (d, J 7.8 Hz, 1H), 7.60 (s, 2H), 7.52 (t, J=8.1 Hz, 1H), 7.48-7.37 (m, 3H), 7.30 (d, J=7.4 Hz, 1H), 4.51 (s, 2H), 3.79 (d, J=6.7 Hz, 1H), 1.50 (d, J=7.1 Hz, 3H). MS (ESI) m/z: 527.8 (M+1).

Example 31: 3-(4-((3-(2,6-dichloro-2'-(trifluoromethoxy)-[1,1'-biphenyl]-4-yl)ureido)methyl)-2-methylphenyl)acetic acid

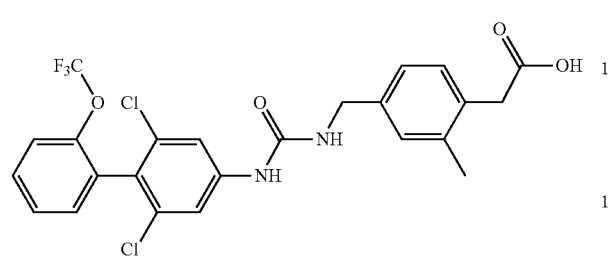

I-31

Step 1: methyl 4-bromo-2-methylphenylacetate 4-bromo-2-methylphenylacetonitrile (1 g, 4.1 mmol) and methanol (10 mL) were added to a 25 mL single-mouth bottle, and then thionyl chloride (5 mL) was added under ice bath, and the mixture reacted under ice bath for 20 minutes, and then reacted at room temperature overnight. After reaction, the mixture was filtered and the solvent was dried with rotation under vacuum to give the product (colorless oil, 630 g), with a yield of 54.3%. $^1$H NMR (400 MHz, CDCl$_3$) δ 7.33 (s, 1H), 7.28 (d, J=8.1 Hz, 1H), 7.06 (d, J=8.1 Hz, 1H), 3.69 (s, 3H), 3.59 (s, 2H), 2.28 (s, 3H). MS (ESI) m/z: 242.9 (MH+).

Step 2: methyl 4-cyano-2-methylphenylacetate

Methyl-4-bromo-2-methylphenylacetate (620 mg, 2.55 mmol), zinc cyanide (448 mg, 3.83 mmol) and N,N-dimethylformamide (10 mL) were added to a 20 mL microwave tube. The mixture was nitrogen sparged for 5 min, tetrakis(triphenylphosphine)palladium (301 mg, 0.26 mmol) was added, and stirred and heated to 155° C. for 2 hours under microwave. After completion of reaction, the mixture was cooled to room temperature, and extracted with ethyl acetate for three times. The organic layers were combined, washed 5 times with water, and finally washed with saturated sodium chloride, and the organic layer was concentrated in vacuo to get a crude product. The crude product was separated by a silica gel column (petroleumether:ethylacetate=8:1-5:1) to give the product (colorless oil, 350 mg), with a yield of 71.5%. $^1$H NMR (400 MHz, CDCl$_3$) δ 7.46 (d, J 8.2 Hz, 2H), 7.30 (d, J 7.7 Hz, 1H), 3.70 (s, 3H), 3.69 (s, 2H), 2.34 (s, 3H). MS (ESI) m/z: 190.1 (MH+).

Step 3: 4-aminomethyl-2-methyl methylphenylacetate 4-cyano-2-methyl methylphenylacetate (200 mg, 1.06 mmol), methanol (2 mL), aqueous ammonia (5 drops, 28%) and Raney Ni were added to a 25 mL single-mouth bottle, and stirred to react at room temperature for 20 min under hydrogen environment at an atmospheric pressure, and then the reaction mixture was filtered by celite, and the solvent was dried with rotation under vacuum to give the product (colorless oil, 110 mg), with a yield of 53.9%. MS (ESI) m/z: 194.1 (MH+).

Step 4: 3-(4-((3-(2,6-dichloro-2'-(trifluoromethyl)-[1,1'-biphenyl]-4-yl)ureido)methyl)2-methylbenzyl) methyl acetate 2,6-dichloro-2'-(trifluoromethoxy)-[1,1'-biphenylyl]-4-amine (100 mg, 0.31 mmol), dichloromethane (4 mL), and N,N-diisopropylethylamine (120 mg, 0.93 mmol) were added to a 25 mL single-mouth bottle, and stirred for 5 min under ice bath with the protection of nitrogen gas, and then triphosgene (35 mg, 0.11 mmol) was added to and the reaction was continued under ice bath for 10 minutes, and then 4-aminomethyl-2-methyl methylphenylacetate (66 mg, 0.37 mmol) was added, and the reaction was continued under ice bath for 30 min. H$_2$O (10 mL) was added and the obtained mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleum ether:ethyl acetate=3:1-2:1) to give the product (white solid, 70 mg), with a yield of 41.7%. MS (ESI) m/z: 540.8 (MH+).

Step 5: 3-(4-((3-(2,6-dichloro-2'-(trifluoromethyl)-[1,1'-biphenyl]-4-yl)ureido)methyl) 2-methylbenzyl) acetic acid 3-(4-((3-(2,6-dichloro-2'-(trifluoromethyl)-[1,1'-biphenyl]-4-yl)ureido)methyl) 2-methylbenzyl)methyl acetate (80 mg, 0.15 mmol), lithium hydroxide (18 mg, 0.45 mmol), ethanol (2 mL), and water (0.5 mL) were added to a 25 mL single-mouth bottle, and reacted at room temperature for 3 hours. After confirming completion of the reaction of materials by TLC, the mixture was adjusted to pH 3 with 2N hydrochloric acid, and white solid precipitated, filtered and the solid was dried in vacuo to give the product (white solid, 65 mg), with a yield of 95.5%. $^1$H NMR (400 MHz, CD$_3$OD) δ 7.59 (s, 2H), 7.52 (td, J=7.8, 1.3 Hz, 1H), 7.43 (d, J=7.4 Hz, 1H), 7.39 (d, J=8.4 Hz, 1H), 7.29 (d, J=7.6 Hz, 1H), 7.20-7.14 (m, 2H), 7.12 (d, J=8.1 Hz, 1H), 4.35 (s, 2H), 3.62 (s, 2H), 2.31 (s, 3H). MS (ESI) m/z: 526.8 (MH+).

Example 32: 3-(4-((3-(2,6-dichloro-2'-(trifluoromethoxy)-[1,1'-biphenyl]-4-yl)ureido)methyl)2-fluorophenyl)acetic acid

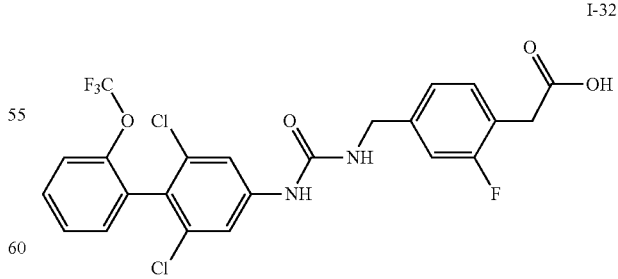

I-32

Step 1: 4-bromo-2-methyl fluorophenylacetate 4-bromo-2-fluorophenylacetonitrile (1 g, 4.67 mmol) and methanol (10 mL) were added to a 25 mL single-mouth bottle, and thionyl chloride (5 mL) was added dropwise under ice bath. After reaction for 20 minutes under ice bath, the mixture reacted at room temperature overnight. After reaction, the mixture was filtered, and the solvent was dried with rotation under vacuum to give the product (colorless oil, 1 g), with a yield of 86.9%. $^1$H NMR (400 MHz, CDCl$_3$) δ 7.49 (t, J 7.7 Hz, 1H), 7.07 (dd, J=9.3, 1.7 Hz, 1H), 6.95 (d, J=8.2 Hz, 1H), 3.70 (s, 3H), 3.59 (s, 2H). MS (ESI) m/z: 245.9 (MH+).

Step 2: 4-cyano-2-methyl fluorophenylacetate 4-bromo-2-ethyl fluorophenylacetate (1.7 g, 6.68 mmol), zinc cyanide (1.21 g, 10.3 mmol), and N,N-dimethylformamide (10 mL) were added to a 20 mL microwave tube. The mixture was nitrogen sparged for 5 min, tetrakis(triphenylphosphine)palladium (795 mg, 0.69 mmol) was added, and the mixture was stirred and heated to 155° C. for 2 hours under microwave. After completion of reaction, the mixture was cooled to room temperature, and extracted with ethyl acetate for three times. The organic layers were combined, washed 5 times with water, finally washed with saturated sodium chloride, and concentrated under a reduced pressure to get a crude product. The crude product was separated by a silica gel column (petroleumether:ethylacetate=8:1-5:1) to give the product (colorless oil, 730 mg), with a yield of 55.3%. $^1$H NMR (400 MHz, CDCl$_3$) δ 7.59 (t, 7=7.3 Hz, 1H), 7.19 (d, J=8.7 Hz, 2H), 3.72 (s, 3H), 3.69 (s, 2H). MS (ESI) m/z: 194.1 (MH+).

Step 3: 4-aminomethyl-2-methyl fluorophenylacetate 4-cyano-2-methyl fluorophenylacetate (160 mg, 0.81 mmol), methanol (4 mL), aqueous ammonia (5 drops, 28%) and Raney Ni were added to a 25 mL single-mouth bottle, and hydrogen gas was introduced to react at room temperature for 1 hour. The reaction mixture was filtered by celite, and the solvent was dried with rotation under vacuum to give the product (colorless oil, 140 mg), with a yield of 85.9%. $^1$H NMR (400 MHz, CDCl$_3$) δ 7.29 (d, J=7.7 Hz, 1H), 7.02 (d, J=8.1 Hz, 1H), 6.99 (d, J=11.1 Hz, 1H), 3.88 (s, 2H), 3.70 (s, 3H), 3.60 (s, 2H), 1.78 (s, 2H). MS (ESI) m/z: 198.1 (MH+).

Step 4: 3-(4-((3-(2,6-dichloro-2'-(Trifluoromethyl)-[1,1'-biphenyl]-4-yl)ureido)methyl) 2-fluorobenzyl) methyl acetate 2,6-dichloro-2'-(trifluoromethoxy)-[1,1'-biphenylyl]-4-amine (100 mg, 0.31 mmol), dichloromethane (4 mL) and N,N-diisopropylethylamine (120 mg, 0.93 mmol) were added to a 25 mL single-mouth bottle, and stirred for 5 min under ice bath with the protection of nitrogen gas, and then triphosgene (35 mg, 0.11 mmol) was added, and the reaction was continued under ice bath for 10 min, and then 4-aminomethyl-2-methyl fluorophenylacetate (73 mg, 0.37 mmol) was added, and the reaction was continued under ice bath for 30 min. H$_2$O (10 mL) was added and the mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (developing agent dichloromethane:methanol=20:1) to give the product (white solid, 80 mg), with a yield of 40.8%. $^1$H NMR (400 MHz, CDCl$_3$) δ 7.85 (s, 1H), 7.44 (m, 1H), 7.38 (s, 2H), 7.34 (d, J=7.9 Hz, 2H), 7.22-7.16 (m, 2H), 6.95-6.92 (m, 1H), 6.90 (d, J=6.1 Hz, 1H), 6.00 (d, J=2.8 Hz, 1H), 4.32 (d, J=3.0 Hz, 2H), 3.68 (s, 3H), 3.58 (s, 2H). MS (ESI) m/z: 544.8 (MH+).

Step 5: 3-(4-((3-(2,6-dichloro-2'-(trifluoromethyl)-[1,1'-biphenyl]-4-yl)ureido)methyl)2-fluorophenyl) acetic acid 3-(4-((3-(2,6-dichloro-2'-(trifluoromethyl)-[1,1'-biphenyl]-4-yl)ureido)methyl) 2-fluorophenyl)methyl acetate (80 mg, 0.15 mmol), lithium hydroxide (18 mg, 0.45 mmol), ethanol (4 mL) and water (1 mL) were added to a 25 mL single-mouth bottle, and reacted at room temperature for 2 hours. After confirming completion of the reaction of materials by TLC, the mixture was adjusted to pH 3 with 2N hydrochloric acid, and white solid precipitated, filtered and the solid was dried in vacuo to give the product (white solid, 70 mg), with a yield of 89.7%. $^1$H NMR (400 MHz, CD$_3$OD) δ 7.58 (s, 2H), 7.54-7.49 (m, 1H), 7.43 (d, J=7.6 Hz, 1H), 7.40 (s, 1H), 7.37 (d, J=3.7 Hz, 1H), 7.34 (d, J=7.9 Hz, 1H), 7.31-7.26 (m, 1H), 7.08 (t, J=9.7 Hz, 2H), 4.44 (s, 2H), 3.61 (s, 2H). MS (ESI) m/z: 530.8 (MH+).

Example 33: 3-(4-((3-(2,6-dichloro-2'-(trifluoromethoxy)-[1,1'-biphenyl]-4-yl)ureido)methyl)2-chlorophenyl)acetic acid

I-33

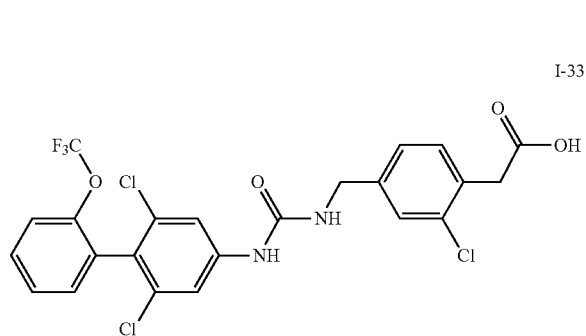 [SMILES: O=C(O)Cc1ccc(CNC(=O)Nc2cc(Cl)c(-c3ccccc3OC(F)(F)F)c(Cl)c2)cc1Cl]

Step 1: methyl 4-bromo-2-chlorophenylacetate 4-bromo-2-chlorophenylacetic acid (1 g, 4.02 mmol), and methanol (10 mL) were added to a 25 mL single-mouth bottle, and then thionyl chloride (0.5 mL) was added to enable the mixture to react at 65° C. for 3 hours. After completion of the reaction, the mixture was concentrated in vacuo to remove the solvent to give the product (colorless oil, 900 mg), with a yield of 84.9%. $^1$H NMR (400 MHz, CDCl$_3$) δ 7.56 (d, J 1.9 Hz, 1H), 7.37 (dd, J 8.2, 1.9 Hz, 1H), 7.16 (d, J 8.2 Hz, 1H), 3.73 (s, 2H), 3.71 (s, 3H)

Step 2: methyl 4-cyano-2-chlorophenylacetate

Methyl 4-bromo-2-chlorophenylacetate (1 g, 3.84 mmol), zinc cyanide (539 mg, 4.61 mmol) and N,N-dimethylformamide (10 mL) were added to a 20 mL microwave tube. The mixture was nitrogen sparged for 5 min, tetrakis(triphenylphosphine)palladium (222 mg, 0.19 mmol) was added, and the mixture was stirred and heated to 155° C. for 1.5 hours under microwave. After completion of reaction, the mixture was cooled to room temperature, and extracted with ethyl acetate for three times. The organic layers were combined, washed 5 times with water, finally washed with saturated sodium chloride, and concentrated in vacuo to get a crude product. The crude product was separated by a silica gel column (petroleumether:ethylacetate=8:1-5:1) to give the product (yellow oil, 350 mg), with a yield of 48.8%. 1 NMR (400 MHz, CDCl₃) δ 7.69 (s, 1H), 7.53 (d, J 1.3 Hz, 1H), 7.42 (d, J 7.9 Hz, 1H), 3.84 (s, 2H), 3.73 (s, 4H).

Step 3: methyl 4-aminomethyl-2-chlorophenylacetate

Methyl 4-cyano-2-chlorophenylacetate (350 mg, 1.67 mmol), methanol (2 mL), aqueous ammonia (5 drops, 28%), and Raney Ni were added to a 25 mL single-mouth bottle, the hydrogen gas was introduced to enable the mixture to react for 1 hour while stirring, and then the mixture was filtered by celite, and the solvent was dried with rotation under vacuum to obtain a colorless oil, which was directly used in the next reaction. MS (ESI) m/z: 214.0 MH+).

Step 4: 3-(4-((3-(2,6-dichloro-2'-(trifluoromethyl)-[1,1'-biphenyl]-4-yl)ureido)methyl)2-chlorophenyl) methyl acetate 2,6-dichloro-2'-(trifluoromethoxy)-[1,1'-biphenylyl]-4-amine (100 mg, 0.31 mmol), dichloromethane (4 mL), and N,N-diisopropylethylamine (120 mg, 0.93 mmol) were added to a 25 mL single-mouth bottle, and stirred for 5 min under ice bath with the protection of nitrogen gas, and then triphosgene (35 mg, 0.11 mmol) was added, and the reaction was continued under ice bath for 10 min, and then methyl 4-aminomethyl-2-chlorophenylacetate (71 mg, 0.37 mmol) was added, and the reaction was continued under ice bath for 30 min. H₂O (10 mL) was added and the obtained mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleum ether:ethyl acetate=3:1-2:1) to give the product (white solid, 90 mg), with a yield of 51.7%. MS (ESI) m/z: 560.7 (MH+).

Step 5: 3-(4-((3-(2,6-dichloro-2'-(trifluoromethyl)-[1,1'-biphenyl]-4-yl)ureido)methyl)2-chlorophenyl) acetic acid 3-(4-((3-(2,6-dichloro-2'-(trifluoromethyl)-[1,1'-biphenyl]-4-yl)ureido)methyl)2-chlorophenyl)methyl acetate (47 mg, 0.084 mmol), lithium hydroxide (11 mg, 0.25 mmol), ethanol (4 mL) and water (1 mL) were added to a 25 mL single-mouth bottle, and reacted at room temperature for 2 hours. After confirming completion of the reaction of materials by TLC, the mixture was adjusted to pH 3 with 2N hydrochloric acid, and white solid precipitated, filtered and the solid was dried in vacuo to give the product (white solid, 35 mg), with a yield of 76.1%. ¹H NMR (400 MHz, CD₃OD) δ 12.51-12.29 (m, 1H), 9.18 (s, 1H), 7.64 (s, 2H), 7.57 (t, J=7.0 Hz, 1H), 7.47 (t, J=7.0 Hz, 2H), 7.39-7.35 (m, 1H), 7.33 (d, J=7.9 Hz, 2H), 7.20 (d, J=9.0 Hz, 1H), 7.04 (s, 1H), 4.28 (d, J=5.8 Hz, 2H), 3.66 (s, 2H). MS (ESI) m/z: 546.7 (MH+).

Example 34: 3-(4-((3-(2,6-dichloro-2'-(trifluoromethoxy)-[1,1'-biphenyl]-4-yl)ureido)methyl)-3-methylphenyl)acetic acid

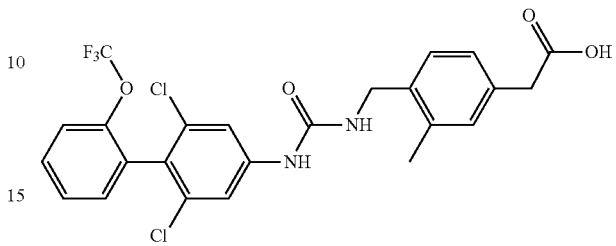

I-34

Step 1: methyl 4-bromo-3-methylphenylacetate 4-bromo-3-methylphenylacetonitrile (1 g, 4.76 mmol) and methanol (10 mL) were added to a 25 mL single-mouth bottle, and thionyl chloride (5 mL) was added under ice bath. After reacted under ice bath for 20 minutes, the obtained mixture reacted at room temperature overnight. After completion of the reaction, the mixture was concentrated in vacuo to remove the solvent to give the product (colorless oil, 1 g), with a yield of 64.1%. ¹H NMR (400 MHz, CDCl₃) δ 7.47 (d, J=8.1 Hz, 1H), 7.15 (s, 1H), 6.96 (dd, J=8.2, 1.6 Hz, 1H), 3.69 (s, 3H), 3.55 (s, 2H), 2.38 (s, 3H).

Step 2: methyl 4-cyano-3-methylphenylacetate

Ethyl-4-bromo-3-methylphenylacetate (1 g, 4.1 mmol), zinc cyanide (722 mg, 6.2 mmol) and N,N-dimethylformamide (10 mL) were added to a 20 mL microwave tube. The mixture was nitrogen sparged for 5 min, tetrakis(triphenylphosphine)palladium (237 mg, 0.21 mmol) was added, and the mixture was stirred and heated to 155° C. for 1.5 hours under microwave. After completion of reaction, the mixture was cooled to room temperature, and extracted with ethyl acetate for three times. The organic layers were combined, washed 5 times with water, and finally washed with saturated sodium chloride, and the organic layer was concentrated in vacuo to remove the solvent to get a crude product. The crude product was separated by a silica gel column (petroleum ether:ethyl acetate=10:1) to give the product (colorless oil, 360 mg), with a yield of 46.2%. ¹H NMR (400 MHz, CDCl₃) δ 7.55 (d, J=7.9 Hz, 1H), 7.24 (s, 1H), 7.19 (d, J=8.0 Hz, 1H), 3.71 (s, 3H), 3.64 (s, 2H), 2.53 (s, 3H). MS (ESI) m/z: 190.1 (MH+)

Step 3: methyl 4-aminomethyl-3-methylphenylacetate

Methyl 4-cyano-3-methylphenylacetate (350 mg, 1.85 mmol), methanol (5 mL), aqueous ammonia (5 drops, 28%) and Raney Ni were added to a 25 mL single-mouth bottle, and the hydrogen gas was introduced to react for 1 hour at room temperature while stirring. The obtained mixture was filtered by celite, and the solvent was dried with rotation under vacuum to give the product (colorless oil, 340 mg), with a yield of 95.2%. MS (ESI) m/z: 194.1 (MH+).

Step 4: 3-(4-((3-(2,6-dichloro-2'-(trifluoromethyl)-[1,1'-biphenyl]-4-yl)ureido)methyl)-3-methylphenyl) methyl acetate 2,6-dichloro-2'-(trifluoromethoxy)-[1,1'-biphenylyl]-4-amine (100 mg, 0.31 mmol), dichloromethane (4 mL) and N,N-diisopropylethylamine (120 mg, 0.93 mmol) were added to a 25 mL single-mouth bottle, and stirred for 5 min under ice bath with the protection of nitrogen gas, and then triphosgene (35 mg, 0.11 mmol) was added, and the reaction was continued under ice bath for 10 min, and then methyl 4-aminomethyl-3-methylphenylacetate (72 mg, 0.37 mmol) was added, and the reaction was continued under ice bath for 30 min. $H_2O$ (10 mL) was added and the obtained mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleum ether:ethyl acetate=5:1-3:1) to give the product (white solid, 90 mg), with a yield of 53.5%. MS (ESI) m/z: 538.8 (M−1)

Step 5: 3-(4-((3-(2,6-dichloro-2'-(trifluoromethyl)-[1,1'-biphenyl]-4-yl)ureido)methyl)-3-methylbenzyl)acetic acid 3-(4-((3-(2,6-dichloro-2'-(trifluoromethyl)-[1,1'-biphenyl]-4-yl)ureido)methyl)-3-methylbenzyl)methyl acetate (90 mg, 0.17 mmol), lithium hydroxide (21 mg, 0.51 mmol), ethanol (4 mL) and water (1 mL) were added to a 25 mL single-mouth bottle, and reacted at room temperature for 2 hours. After confirming completion of the reaction of materials by TLC, the mixture was adjusted to pH 3 with 2N hydrochloric acid, and white solid precipitated, filtered and the solid was dried in vacuo to give the product (white solid, 37 mg), with a yield of 42.0%. $^1$H NMR (400 MHz, DMSO) δ 14.32-13.80 (m, 1H), 9.06 (s, 1H), 7.64 (s, 2H), 7.60-7.54 (m, 1H), 7.48 (t, J=7.0 Hz, 2H), 7.41-7.35 (m, 1H), 7.18 (d, J=8.3 Hz, 1H), 7.08-7.02 (m, 2H), 6.83 (t, J=5.6 Hz, 1H), 4.26 (d, J=5.6 Hz, 2H), 3.49 (s, 2H), 2.27 (s, 3H). MS (ESI) m/z: 527.0 (MH+).

Example 35: 3-(4-((3-(2,6-dichloro-2'-(trifluoromethoxy)-[1,1'-biphenyl]-4-yl)ureido)methyl)-3-fluorophenyl)acetic acid

I-35

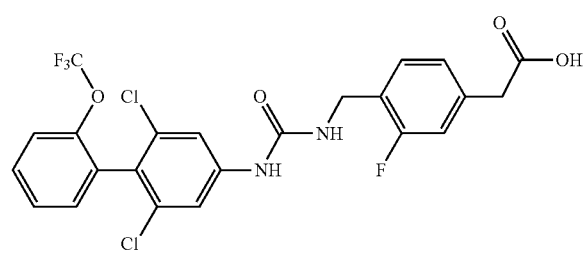

Step 1: methyl 4-bromo-3-fluorophenylacetate 4-bromo-3-fluorophenylacetic acid (1 g, 4.3 mmol) and methanol (10 mL) were added to a 25 mL of single-mouth bottle, and thionyl chloride (0.5 mL) were added under ice bath, and reacted at room temperature for 3 hours. After reaction, the mixture was filtered and the solvent was dried with rotation under vacuum to give the product (colorless oil, 1.3 g), which was directly used in the next step. $^1$H NMR (400 MHz, CDCl$_3$) δ 7.49 (t, 7=7.7 Hz, 1H), 7.08 (dd, J=9.3, 1.8 Hz, 1H), 6.95 (dd, J=8.2, 1.4 Hz, 1H), 3.71 (s, 3H), 3.59 (s, 2H).

Step 2: methyl 4-cyano-3-fluorophenylacetate

Ethyl-4-bromo-3-fluorophenylacetate (1.3 g, 5.3 mmol), zinc cyanide (924 mg, 7.89 mmol) and N,N-dimethylformamide (10 mL) were added to a 20 mL microwave tube. The mixture was nitrogen sparged for 5 min, tetrakis(triphenylphosphine)palladium (613 mg, 0.53 mmol) was added, and the mixture was stirred and heated to 155° C. for 1.5 hours under microwave. After completion of reaction, the mixture was cooled to room temperature, and extracted with ethyl acetate for three times, and the organic layers were combined, washed 5 times with water, and finally washed with saturated sodium chloride, and the organic layer was concentrated in vacuo to get a crude product. Then the crude product was separated by a silica gel column (petroleum ether:ethyl acetate=8:1-5:1) to give the product (while solid, 620 mg), with a yield of 60.2%. $^1$H NMR (400 MHz, CDCl$_3$) 7.58 (t, J=7.2 Hz, 1H), 7.18 (d, J=8.7 Hz, 2H), 3.72 (s, 3H), 3.69 (s, 2H). MS (ESI) m/z: 194.1 (MH+)

Step 3: methyl-4-aminomethyl-3-fluorophenylacetate

Methyl-4-cyano-3-fluorophenylacetate (350 mg, 1.78 mmol, methanol (4 mL), aqueous ammonia (5 drops, 28%) and Raney Ni were added to a 25 mL single-mouth bottle, the hydrogen gas was introduced to react for 2 hours while stirring, and then the reaction mixture was filtered by celite, and the solvent was dried with rotation under vacuum to give the product (colorless oil, 300 mg), with a yield of 84.0%. MS (ESI) m/z: 198.1 MH+).

Step 4: 3-(4-((3-(2,6-dichloro-2'-(trifluoromethyl)-[1,1'-biphenyl]-4-yl)ureido)methyl)3-fluorobenzyl)methyl acetate 2,6-dichloro-2'-(trifluoromethoxy)-[1,1'-biphenylyl]-4-amine (100 mg, 0.31 mmol), dichloromethane (4 mL) and N,N-diisopropylethylamine (120 mg, 0.93 mmol) were added to a 25 mL single-mouth bottle, and stirred for 5 min under ice bath with the protection of nitrogen gas, and then triphosgene (35 mg, 0.11 mmol) was added, and the reaction was continued under ice bath for 10 minutes, and then 4-aminomethyl-methyl 3-fluorophenylacetate (73 mg, 0.37 mmol) was added, and the reaction was continued under ice bath for 30 min. $H_2O$ (10 mL) was added and the obtained mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleum ether:ethyl acetate=5:1) to give the product (white solid, 85 mg), with a yield of 50.3%. $^1$H NMR (400 MHz, CDCl$_3$) δ 7.46-7.42 (m, 3H), 7.39-7.33 (m, 2H), 7.24 (dd, J 7.8, 1.7 Hz, 2H), 7.11 (s, 1H), 7.02-6.93 (m, 2H), 4.40 (s, 2H), 3.72 (s, 3H), 3.63 (s, 2H). MS (ESI) m/z: 544.8 (MH+).

Step 5: 3-(4-((3-(2,6-dichloro-2'-(trifluoromethyl)-[1,1'-biphenyl]-4-yl)ureido)methyl)-3-fluorobenzyl)acetic acid 3-(4-((3-(2,6-dichloro-2'-(trifluoromethyl)-[1,1'-biphenyl]-4-yl)ureido)methyl)-3-fluorobenzyl)methyl acetate (85 mg, 0.16 mmol), lithium hydroxide (20 mg, 0.48 mmol), ethanol (5 mL) and water (1 mL) were added to a 25 mL single-mouth bottle, and reacted at room temperature for 2 hours. After confirming completion of the reaction of materials by TLC, the mixture was adjusted to pH 3 with 2N hydrochloric acid, and white solid precipitated, filtered and the solid was dried in vacuo to give the product (white solid, 45 mg), with a yield of 54.2%. $^1$H NMR (400 MHz, DMSO) δ 12.40 (s, 1H), 9.13 (s, 1H), 7.64 (s, 2H), 7.57 (t, J=7.8 Hz, 1H), 7.48 (t, J=7.0 Hz, 2H), 7.40-7.35 (m, 1H), 7.29 (t, J=7.9 Hz, 1H), 7.07 (t, J=9.5 Hz, 2H), 6.95 (t, J=5.9 Hz, 1H), 4.32 (d, J=5.7 Hz, 2H), 3.57 (s, 2H). MS (ESI) m/z: 530.8 (MH+).

Example 36: 3-(4-((3-(2,6-dichloro-2'-(trifluoromethoxy)-[1,1'-biphenyl]-4-yl)ureido)methyl)phenyl)propanoic acid

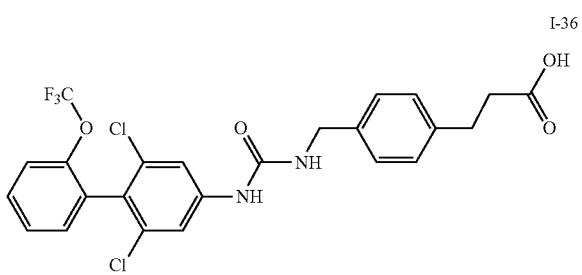 [SMILES: O=C(O)CCc1ccc(CNC(=O)Nc2cc(Cl)c(-c3ccccc3OC(F)(F)F)c(Cl)c2)cc1]

I-36

Step 1: methyl 4-cyanobenzoate 4-cyanobenzenepropionic acid (1 g, 5.7 mmol) and methanol (10 mL) were added to a 25 mL single-mouth bottle, thionyl chloride (0.5 mL) was added dropwise at room temperature, and the mixture reacted at room temperature for 3 hours while stirring. After the reaction, the mixture was concentrated in vacuo to remove the solvent under a reduced pressure, and the resulting crude product was dissolved in ethyl acetate (20 mL), and washed with saturated sodium chloride. The organic layer was dried over anhydrous sodium sulfate, and filtered, and the filtrate was concentrated in vacuo to give the product (colorless oil, 960 mg). $^1$H NMR (400 MHz, CDCl$_3$) δ 7.57 (d, J=8.2 Hz, 2H), 7.30 (d, J=8.1 Hz, 2H), 3.66 (s, 3H), 3.00 (t, J=7.6 Hz, 2H), 2.64 (t, J=7.6 Hz, 2H). MS (ESI) m/z: 190.1 (MH+).

Step 2: methyl 4-aminomethyl phenylpropionate

Methyl 4-cyano-phenylpropionate (500 mg, 2.65 mmol), methanol (5 mL), aqueous ammonia (5 drops, 28%) and Raney Ni were added to a 25 mL single-mouth bottle, and the hydrogen gas was introduced to enable the mixture to react for 3 hours at room temperature while stirring. After the reaction, the mixture was filtered by celite, and the solvent was dried with rotation under vacuum to give a crude product. The crude product was separated by a silica gel column (dichloromethane:methanol=50:1-25:1) to give the product (while solid, 126 mg), with a yield of 24.7%. MS (ESI) m/z: 194.1 (MH+)

Step 3: 3-(4-((3-(2,6-dichloro-2'-(trifluoromethyl)-[1,1'-biphenyl]-4-yl)ureido)methyl) phenyl)methyl propionate 2,6-dichloro-2'-(trifluoromethoxy)-[1,1'-biphenylyl]-4-amine (100 mg, 0.31 mmol), dichloromethane (4 mL) and N,N-diisopropylethylamine (120 mg, 0.93 mmol) were added to a 25 mL single-mouth bottle, and stirred for 5 min under ice bath with the protection of nitrogen gas, and then triphosgene (35 mg, 0.11 mmol) was added, and the reaction was continued under ice bath for 10 min, and then methyl 4-aminomethyl phenylpropionate (66 mg, 0.37 mmol) was added, and the reaction was continued under ice bath for 30 min, leaving the reaction at room temperature for 1 hour. H$_2$O (10 mL) was added and the obtained mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by a silica gel column (petroleum ether:ethyl acetate=3:1-2:1) to give the product (white solid, 110 mg), with a yield of 59.4%. $^1$H NMR (400 MHz, CDCl$_3$) δ 7.87 (s, 1H), 7.48-7.41 (m, 1H), 7.40 (s, 2H), 7.34 (d, J=7.5 Hz, 2H), 7.18 (dd, J=6.5, 5.2 Hz, 1H), 7.11 (d, J=8.1 Hz, 2H), 7.06 (d, J=8.1 Hz, 2H), 6.00 (d, J=1.0 Hz, 1H), 4.26 (s, 2H), 3.62 (s, 3H), 2.86 (t, J=7.7 Hz, 2H), 2.56 (t, J=7.7 Hz, 2H). MS (ESI) m/z: 540.8 (MH+).

Step 4: 3-(4-((3-(2,6-dichloro-2'-(trifluoromethyl)-[1,1'-biphenyl]-4-yl)ureido)methyl)phenyl) propionic acid 3-(4-((3-(2,6-dichloro-2'-(trifluoromethyl)-[1,1'-biphenyl]-4-yl)ureido)methyl)phenyl) methyl propionate (110 mg, 0.2 mmol), lithium hydroxide (26 mg, 0.6 mmol), ethanol (4 mL) and water (1 mL) were added to a 25 mL single-mouth bottle, and reacted at room temperature for 1 hour. After confirming completion of the reaction of materials by TLC, the mixture was adjusted to pH 3 with 2N hydrochloric acid, and white solid precipitated, filtered and the solid was dried in vacuo to give the product (white solid, 90 mg), with a yield of 84.1%. $^1$H NMR (400 MHz, CD$_3$OD) δ 7.58 (s, 2H), 7.51 (t, J=11.1, 4.6 Hz, 1H), 7.45-7.37 (m, 2H), 7.29 (d, J=7.7 Hz, 1H), 7.26 (d, J=8.0 Hz, 2H), 7.21 (d, J=8.0 Hz, 2H), 4.36 (s, 2H), 2.90 (t, J=7.6 Hz, 2H), 2.58 (t, J=7.6 Hz, 2H). MS (ESI) m/z: 526.9 (MH+).

Example 37: 2-(4-((3-(2,6-dichloro-2'-(trifluoromethoxy)-[1,1'-biphenyl]-4-yl)ureido)methyl)phenyl)-2-hydroxyacetic acid

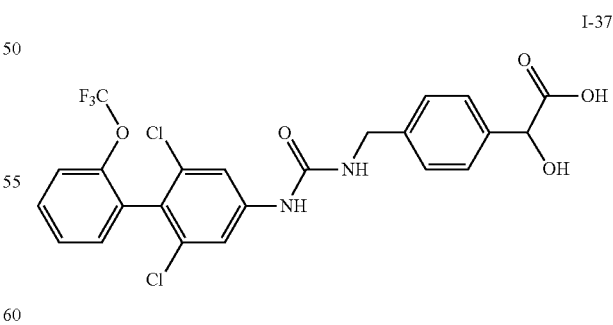

I-37

Step 1: 4-bromophenyl-2-methyl hydroxyacetate 4-bromophenyl-2-hydroxyacetic acid (2 g, 8.66 mmol) and methanol (10 mL) were added to a 25 mL single-mouth bottle, thionyl chloride (0.5 mL) were added under ice bath, and the obtained mixture reacted at 65° C. for 2 hours. After reaction, the mixture was concentrated in vacuo to remove the solvent, and the resulting crude product was dissolved in ethyl acetate, and washed with saturated sodium chloride. The organic layer was concentrated under a reduced pressure to give the product (white solid, 2.1 g), with a yield of 99%. $^1$H NMR (400 MHz, CDCl$_3$) δ 7.49 (d, J=8.4 Hz, 2H), 7.30 (d, J=8.4 Hz, 2H), 5.14 (s, 1H), 3.76 (s, 3H).

Step 2: 4-cyanophenyl-2-methyl hydroxyacetate 4-bromophenyl-2-methyl hydroxyacetate (1 g, 4.1 mmol), zinc cyanide (720 mg, 6.1 mmol) and N,N-dimethylformamide (10 mL) were added to a 20 mL microwave tube. The mixture was nitrogen sparged for 5 min, tetrakis(triphenylphosphine)palladium (240 mg, 0.2 mmol) was added, and the mixture was stirred and heated to 155° C. for 1.5 hours under microwave. After completion of reaction, the mixture was cooled to room temperature, and extracted with ethyl acetate for three times, and the organic layers were combined, washed 5 times with water, and finally washed with saturated sodium chloride. The organic layer was concentrated in vacuo, and then the crude product was separated by a silica gel column (petroleumether:ethylacetate=3:1-2:1) to give the product (yellow oil, 450 mg), with a yield of 38.5%. $^1$H NMR (400 MHz, CDCl$_3$) δ 7.67 (d, 7=8.2 Hz, 2H), 7.58 (d, J=8.2 Hz, 2H), 5.25 (s, 1H), 3.79 (s, 3H). MS (ESI) m/z: 192.0 (MH+).

Step 3: 4-aminomethylphenyl-2-methyl hydroxyacetate 4-cyanophenyl-2-methyl hydroxyacetate (200 mg, 1.05 mmol), methanol (2 mL), aqueous ammonia (10 drops, 28%) and Raney Ni were added to a 25 mL single-mouth bottle, the hydrogen gas was introduced to react for 2 hours at room temperature while stirring, and then the mixture was filtered by celite, and the solvent was dried with rotation under vacuum to give the product (colorless oil, 130 mg), with a yield of 63.7%. MS (ESI) m/z: 196.2 (MH+).

Step 4: 2-(4-((3-(2,6-dichloro-2'-(Trifluoromethyl)-[1,1'-biphenyl]-4-yl)ureido)methyl)phenyl)-2-methyl hydroxyacetate 2,6-dichloro-2'-(trifluoromethoxy)-[1,1'-biphenylyl]-4-amine (100 mg, 0.31 mmol), dichloromethane (4 mL) and N,N-diisopropylethylamine (120 mg, 0.93 mmol) were added to a 25 mL single-mouth bottle, and stirred for 5 min under ice bath with the protection of nitrogen gas, and then triphosgene (35 mg, 0.11 mmol) was added, and the reaction was continued under ice bath for 10 min, and then 4-aminomethylphenyl-2-methyl hydroxyacetate (72 mg, 0.37 mmol) was added, and the reaction was continued under ice bath for 30 min. H$_2$O (10 mL) was added and the obtained mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by preparative thin layer chromatography (petroleum ether:ethyl acetate=10:1-1:1) to give the product (white solid, 40 mg), with a yield of 23.8%. MS (ESI) m/z: 542.8 (MH+).

Step 5: 2-(4-((3-(2,6-dichloro-2'-(trifluoromethyl)-[1,1'-biphenyl]-4-yl)ureido)methyl)phenyl)-2-hydroxyacetic acid 2-(4-((3-(2,6-dichloro-2'-(trifluoromethyl)-[1,1'-biphenyl]-4-yl)ureido) methyl)phenyl)-2-methyl hydroxyacetate (40 mg, 0.07 mmol), lithium hydroxide (9 mg, 0.21 mmol), ethanol (2 mL) and water (0.5 mL) were added to a 25 mL single-mouth bottle, and reacted at room temperature for 3 hours. After confirming completion of the reaction of materials by TLC, the mixture was adjusted to pH 3 with 2N hydrochloric acid, and white solid precipitated, and filtered to obtain a crude product, and the crude product was further separated by preparative thin layer chromatography to give the product (white solid, 7 mg), with a yield of 17.9%. $^1$H NMR (400 MHz, CD$_3$OD) δ 7.58 (s, 2H), 7.55-7.42 (m, 3H), 7.42-7.36 (m, 2H), 7.33 (s, 2H), 7.28 (d, J=7.4 Hz, 1H), 4.40 (s, 2H), 2.03 (s, 1H). MS (ESI) m/z: 526.8 (M–1).

Example 38: 2-(4-((3-(2,6-dichloro-2'-(trifluoromethoxy)-[1,1'-biphenyl]-4-yl)ureido)methyl)phenyl)-2-fluoroacetic acid

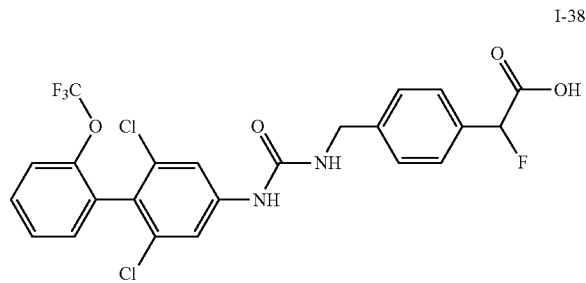 [SMILES: O=C(NCc1ccc(C(F)C(=O)O)cc1)Nc1cc(Cl)c(-c2ccccc2OC(F)(F)F)c(Cl)c1]

I-38

Step 1: methyl-4-bromophenyl-2-fluoroacetate

Methyl 4-bromophenyl-2-fluoroacetate (1 g, 4.1 mmol) (same as the step 1 in Example 56) and dichloromethane (10 mL) were added to a 25 mL single-mouth bottle, after the obtained mixture was stirred under ice bath for 5 minutes, the bottle was added with bis(2-methoxyethyl)aminosulfur trifluoride (1.35 g, 6.1 mmol) dropwise, and the mixture reacted at room temperature overnight. After being cooled under ice bath, the reaction was quenched by the addition of saturated sodium hydrogen carbonate, and the mixture was extracted with dichloromethane (3×20 mL) and washed with saturated sodium chloride. The organic layer was concentrated in vacuo to remove the solvent and separated by a silica gel column (petroleum ether:ethyl acetate=4:1) to give the product (colorless liquid, 720 mg), with a yield of 72%. $^1$H NMR (400 MHz, CDCl$_3$) δ 7.54 (d, J=7.7 Hz, 2H), 7.34 (d, J=7.7 Hz, 2H), 5.75 (d, J 47.3 Hz, 1H), 3.78 (s, 3H).

Step 2: methyl 4-cyanophenyl-2-fluoroacetate

Methyl-4-bromo-2-chlorophenylacetate (600 mg, 2.4 mmol), zinc cyanide (426 mg, 3.6 mmol), and N,N-dimethylformamide (10 mL) were added to a 20 mL microwave tube. The mixture was nitrogen sparged for 5 min, tetrakis(triphenylphosphine)palladium (138 mg, 0.12 mmol) was added, and the mixture was stirred and heated to 155° C. for 1.5 hours under microwave. After completion of reaction, the mixture was cooled to room temperature, extracted with ethyl acetate for three times. The organic layers were combined, washed for 5 times with water, and finally washed with saturated sodium chloride, and the organic layer was concentrated under a reduced pressure to get a crude product. Then the crude product was separated by a silica gel column (petroleumether:ethylacetate=10:1) to give the product (yellow oil, 270 mg), with a yield of 49.4%.

Step 3: methyl 4-aminomethylphenyl-2-fluoroacetate

Methyl 4-cyanophenyl-2-fluoroacetate (100 mg, 0.52 mmol), methanol (2 mL), concentrated hydrochloric acid (5 drops) and Raney Ni were added to a 25 mL single-mouth bottle, and the hydrogen gas was introduced. The reaction mixture was stirred for 10 minutes at room temperature, and filtered by celite, and the solvent was dried with rotation under vacuum to obtain a yellow solid, which was used in the next reaction directly. MS (ESI) m/z: 198.1 (MH+).

Step 4: 2-(4-((3-(2,6-dichloro-2'-(trifluoromethyl)-[1,1'-biphenyl]-4-yl)ureido)methyl)phenyl)-2-methyl fluoroacetate 2,6-dichloro-2'-(trifluoromethoxy)-[1,1'-biphenylyl]-4-amine (100 mg, 0.31 mmol), dichloromethane (4 mL) and N,N-diisopropylethylamine (120 mg, 0.93 mmol) were added to a 25 mL single-mouth bottle, and stirred for 5 min under ice bath with the protection of nitrogen gas, and then triphosgene (35 mg, 0.11 mmol) was added, and the reaction was continued under ice bath for 10 min, and then 4-aminomethylphenyl-2-methyl fluoroacetate (72 mg, 0.37 mmol) was added, and the reaction was continued under ice bath for 30 min. $H_2O$ (10 mL) was added and the obtained mixture was washed with saturated ammonium chloride, and extracted with dichloromethane (10 mL×3). The organic layers were combined, washed with saturated sodium chloride (10 mL), dried over anhydrous sodium sulfate, and filtered, and the filtrate was concentrated in vacuo to obtain a crude product. The crude product was separated by a silica gel column (petroleumether:ethylacetate=4:1-2:1) to give the product (white solid, 20 mg), with a yield of 11.8%. $^1$H NMR (400 MHz, CDCl$_3$) δ 7.73 (s, 1H), 7.48-7.40 (m, 3H), 7.37-7.30 (m, 4H), 7.28-7.26 (m, 1H), 7.25 (s, 1H), 7.19 (d, J=7.7 Hz, 1H), 7.15 (s, 1H), 5.97 (t, J=5.5 Hz, 1H), 5.76 (d, J=47.6 Hz, 1H), 4.36 (d, J=5.4 Hz, 2H), 3.74 (s, 4H). MS (ESI) m/z: 544.7 (M−1).

Step 5: 2-(4-((3-(2,6-dichloro-2'-(trifluoromethyl)-[1,1'-biphenyl]-4-yl)ureido)methyl)phenyl)-2-fluoro-acetic acid 2-(4-((3-(2,6-dichloro-2'-(trifluoromethyl)-[1,1'-biphenyl]-4-yl)ureido)methyl)phenyl)-2-methyl fluoroacetate (20 mg, 0.037 mmol), lithium hydroxide (4.6 mg, 0.11 mmol), ethanol (2 mL), and water (0.5 mL) were added to a 25 mL single-mouth bottle, and reacted at room temperature for 2 hours. After confirming completion of the reaction of materials by TLC, the mixture was adjusted to pH 3 with 2N hydrochloric acid, and white solid precipitated, filtered and the solid was dried in vacuo to give the product (white solid, 13 mg), with a yield of 97.4%. $^1$H NMR (400 MHz, CD$_3$OD) δ 7.59 (s, 2H), 7.51 (t, J=7.9 Hz, 1H), 7.49-7.43 (m, 2H), 7.43-7.36 (m, 4H), 7.29 (d, J=7.6 Hz, 1H), 5.82 (d, J=48.2 Hz, 1H), 4.43 (s, 2H). MS (ESI) m/z: 528.7 (M−1).

Example 39: Determination of Inhibitory Activity of Compounds on RORγ Receptors in Vitro The inhibitory activity of compounds on RORγ receptor was determined by fluorescence resonance energy transfer (FRET) experiments. The inhibitory activity was expressed by half-inhibitory concentration (IC$_{50}$).

Experiment Method:
1. Preparation of RORγ Buffer Solution
10 mL of DTT and 100 mL buffer solution were gently mixed together and ready to use.
2. Preparation of Compound Solution
The concentration of compound solution started from 7.5 mM to 0.25 mM, which was diluted by every 3 folds from 7.5 nM with 10 concentrations totally.
3. Preparation of Protein Mixture
a. 40 nM B-RORγ LBD solution and 20 nM SA-APC solution were gently mixed together. The reaction mixture was incubated for 15 minutes at room temperature. Then 400 nM Biotin was added to the described above mixture. After gently mixed together, the resulting mixture was incubated for 10 minutes at room temperature.
b. 40 nM Bioin-SRC1 solution and 10 nM SA-eu solution were gently mixed together, and the reaction mixture was incubated for 15 minutes at room temperature. Then 200 nM Biotin was added to the described above mixture. After gently mixed together, the resulting mixture was incubated for 10 minutes at room temperature.
c. The described above two pre-mixes were gently mixed together with a ratio of 1:1, and the resulting mixture was incubated for 5 minutes at room temperature.
d. A mixture of 0.1 μM alternative agonist N-(2-chloro-6-fluorophenyl)-N-((20-methoxy-[1,10-biphenylyl]-4-substituted)methyl)benzenesulfonamide, 25 μL B-RORγ LBD/SA-APC and Bioin-SRC1/SA-eu mixture solution with test compound were added to one of the well of a 384-well plate, then they were centrifuged for 1 minute at 1000 rpm, and incubated at room temperature for 1 hour. The values were read on the Envision microplate detector and IC$_{50}$ was calculated. The test results are shown in Table 1.

TABLE 1

Determination Results for RORγ Inhibitory Activity of Example Compounds

| No. | IC$_{50}$ |
|---|---|
| 1-1 | +++ |
| 1-2 | + |
| 1-3 | ++ |
| 1-4 | +++ |
| 1-5 | +++ |
| 1-6 | +++ |
| 1-7 | +++ |
| 1-8 | ++ |
| 1-9 | +++ |
| 1-10 | ++ |
| 1-11 | +++ |
| 1-12 | +++ |
| 1-13 | +++ |
| 1-14 | ++ |
| 1-15 | +++ |
| 1-16 | +++ |
| 1-17 | +++ |
| 1-18 | ++ |
| 1-19 | ++ |
| 1-20 | +++ |
| 1-21 | +++ |
| 1-22a | ++ |
| 1-22b | ++ |
| 1-23 | + |
| 1-24 | ++ |
| 1-25 | +++ |
| 1-26 | ++ |
| 1-27 | ++ |
| 1-28 | ++ |

TABLE 1-continued

Determination Results for RORγ Inhibitory Activity of Example Compounds

| No. | IC$_{50}$ |
|---|---|
| 1-29 | +++ |
| 1-30 | ++ |
| 1-31 | ++ |
| 1-32 | +++ |
| 1-33 | +++ |
| 1-34 | +++ |
| 1-35 | +++ |
| 1-36 | ++ |
| 1-37 | +++ |
| 1-38 | +++ |

The IC$_{50}$ value is the average of at least two independent tests.
+++ indicates IC$_{50}$ < 500 nM; ++ indicates 500 nM ≤ IC$_{50}$ < 5000 nM; and + indicats 5000 nM ≤ IC$_{50}$ < 50000 nM.

Results: Most of the compounds in the present invention have a strong inhibitory activity on the RORγ protein receptors.

Example 40: Experiment of Inhibition on Mouse Th17 Cell Differentiation

Experimental method: Mouse spleen CD4$^+$ T cells were isolated and differentiated into Th17 cells. CD4$^+$ T cells were cultured in the environment of anti-CD3 (0.25 μg/mL), anti-CD28 (1 μg/mL), anti-IL4 (2 μg/mL), anti-IFN-γ (2 μg/mL), TGF-β (5 ng/mL), and IL6 (20 ng/mL), and then the test compound was added. After 96 hours, the differentiation efficiency of Th17 was analyzed. Before collection of cells, PMA at 50 ng/mL and ionomycin at 500 ng/mL were added for stimulation for 4 hours, and the ratio of IL-17 was detected by intracellular staining and flow cytometry. At the same time, we used Live/Dead Cell Dye (Invitrogen) staining method to analyze the cell survival rate, to judge whether the drug had toxicity to cells, and determine the inhibition rate of the compound at a concentration of 0.3 μM on IL-17 differentiation by Th 17 cells. The results are shown in the Table 2 below.

TABLE 2

Determination result for inhibition experiment for Th17 cell differentiation

| No. | % inh@0.3 μM |
|---|---|
| I-1 | +++ |
| 1-2 | + |
| 1-3 | ++ |
| 1-4 | ++ |
| 1-5 | +++ |
| 1-6 | ++ |
| 1-7 | + |
| 1-8 | − |
| 1-9 | − |
| 1-10 | − |
| 1-11 | − |
| 1-12 | − |
| 1-13 | − |
| 1-14 | + |
| 1-15 | +++ |
| 1-16 | + |
| 1-17 | +++ |
| 1-18 | + |
| 1-19 | + |
| 1-20 | + |
| 1-21 | + |
| 1-22a | + |
| 1-22b | + |
| 1-23 | + |
| 1-24 | − |
| 1-25 | − |
| 1-26 | + |
| 1-27 | − |
| 1-28 | − |
| 1-29 | − |
| 1-30 | − |
| 1-31 | − |
| 1-32 | − |
| 1-33 | − |
| 1-34 | − |
| 1-35 | − |
| 1-36 | − |
| 1-37 | − |
| 1-38 | − |

+++ indicates that % inh@0.3 μM is within the range of 70 to 100; ++ indicates that % inh@0.3 μM is within the range of 40 to 70; + indicates that % inh@0.3 μM is within the range of 0 to 40; and − indicates that test is not performed.

Results: Some compounds of the present invention have strong inhibition on the differentiation of mouse Th17 cells.

The invention claimed is:
1. A compound shown by formula II or a pharmaceutically acceptable salt thereof:

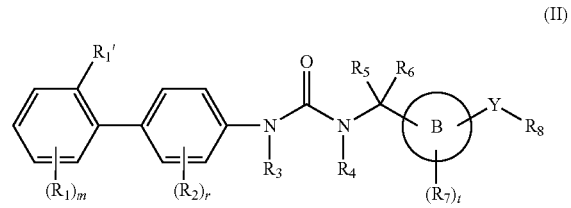

(II)

wherein:
B is phenyl or pyridyl;
R$_1$ is optionally selected from a group consisting of hydrogen, methyl, halogen, cyano, hydroxyl, —CF$_3$, —CHF$_2$, and —CH$_2$F;
R$_1$' is selected from a group consisting of hydrogen, —OCF$_3$, —OCHF$_2$, —CF$_3$, and heteroaryl;
R$_2$ is optionally selected from a group consisting of hydrogen, halogen, cyano, hydroxyl, C$_1$-C$_6$ alkyl, halogen-substituted C$_1$-C$_6$ alkyl, C(O)OR$_a$ or cycloalkyl substituted C$_1$-C$_6$ alkyl, C$_3$-C$_6$ cycloalkyl, C$_3$-C$_6$ oxo (azo)heterocycloalkyl, C$_1$-C$_6$ alkoxyl, halogen-substituted C$_1$-C$_6$ alkoxyl, hydroxyl or C$_1$-C$_3$ alkoxyl substituted C$_1$-C$_3$ alkyl, phenyl, substituted heteroaryloxyl, C$_2$-C$_6$ alkenyl, halogen substituted aromatic ketone group, carboxyl or cyano substituted heteroaryl, —C(O)R$_a$, —(CH$_2$)$_n$NR$_{a1}$R$_{a2}$, —(CH$_2$)$_n$C(O)OR$_a$, —C(O)NR$_{a1}$R$_{a2}$;
R$_3$ and R$_4$ each is hydrogen;
R$_5$ and R$_6$ each is hydrogen;
R$_7$ is optionally selected from a group consisting of hydrogen, halogen, cyano, hydroxyl, C$_1$-C$_6$ alkyl, halogen-substituted C$_1$-C$_6$ alkyl, C(O)OR$_a$ or cycloalkyl substituted C$_1$-C$_6$ alkyl, C$_3$-C$_6$ cycloalkyl, C$_3$-C$_6$ oxo (azo)heterocycloalkyl, C$_1$-C$_6$ alkoxyl, halogen-substituted C$_1$-C$_6$ alkoxyl, hydroxyl or C$_1$-C$_3$ alkoxyl substituted C$_1$-C$_3$ alkyl, phenyl, substituted phenyl, phenoxyl, substituted phenoxyl, heterocyclyl, heterocyclooxyl, heteroaryl, heteroaryloxyl, $C_2$-$C_6$ alkenyl, halogen-substituted aromatic ketone group, carboxyl or cyano substituted heteroaryl, —C(O)$R_a$, —(CH$_2$)$_n$NR$_{a1}$R$_{a2}$, —(CH$_2$)$_n$C(O)OR$_a$ and —C(O)NR$_{a1}$R$_{a2}$;

Y is a covalent bond;

when $R_8$ is

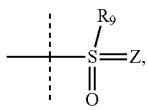

wherein Z is O, and $R_9$ is methyl, ethyl, or —NH$_2$; or
Y is —CR$_{a1}$R$_{a2}$, when $R_8$ is

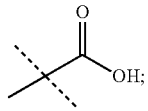

$R_a$, $R_{a1}$ and $R_{a2}$ are each independently selected from hydrogen or $C_1$-$C_3$ alkyl;

m, r, t and n are each independently selected from any integer value of 0~2.

2. The compound or the pharmaceutically acceptable salt thereof according to claim 1, wherein m is 1 and $R_1$ is selected from a group consisting of —H, —Cl, —F, and —CH$_3$.

3. The compound or the pharmaceutically acceptable salt thereof according to claim 2, wherein r is 1 and $R_2$ is selected from a group consisting of —H, —Cl, —F, —CF$_3$, —OCF$_3$, —CN, $C_1$-$C_3$ alkyl and heteroaryl.

4. The compound or the pharmaceutically acceptable salt thereof according to claim 2, wherein r is 2 and $R_2$ is selected from a group consisting of —Cl, —F, —CF$_3$, —OCF$_3$, —CN, and $C_1$-$C_3$ alkyl.

5. The compound or the pharmaceutically acceptable salt thereof according to claim 1, wherein $R_7$ is optionally selected from a group consisting of hydrogen, halogen, cyano, hydroxyl, and $C_1$-$C_6$ alkyl.

6. The compound or the pharmaceutically acceptable salt thereof according claim 1, wherein the compound is as shown in Formula III:

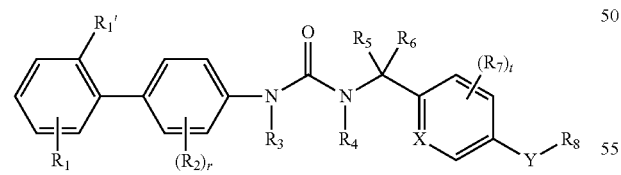

wherein:
X is CH or N;
$R_1$ is optionally selected from a group consisting of —H, —Cl, —F, and —CH$_3$;
$R_1'$ is optionally selected from a group consisting of —H, —OCF$_3$, —OCHF$_2$ and —CF$_3$;
$R_2$ is optimally selected from a group consisting of —H, —Cl, —F, —CF$_3$, —OCF$_3$, —CN and $C_1$-$C_3$ alkyl;
$R_3$ and $R_4$ each is hydrogen;
$R_5$ and $R_6$ each is hydrogen;

$R_7$ is optionally selected from a group consisting of hydrogen, halogen, cyano, hydroxyl, and $C_1$-$C_6$ alkyl;

Y is a covalent bond;

when $R_8$ is

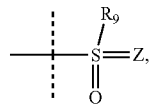

wherein Z is O, and $R_9$ is methyl, ethyl, or —NH$_2$; or
Y is —CR$_{a1}$R$_{a2}$, when $R_8$ is

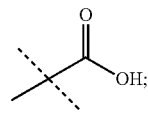

$R_a$, $R_{a1}$ and $R_{a2}$ are each independently selected from hydrogen or $C_1$-$C_3$ alkyl; and r and t are each independently selected from 1 or 2.

7. A compound or a pharmaceutically acceptable salt thereof according to claim 1, wherein the compound is selected from:

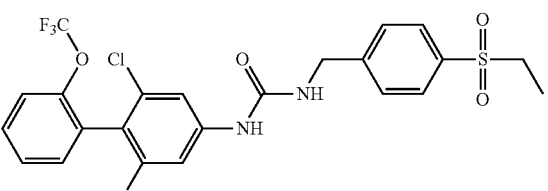

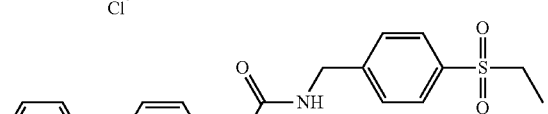

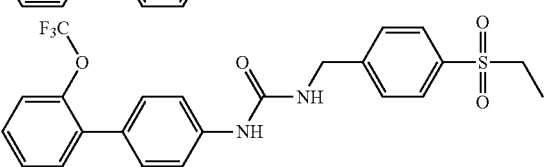

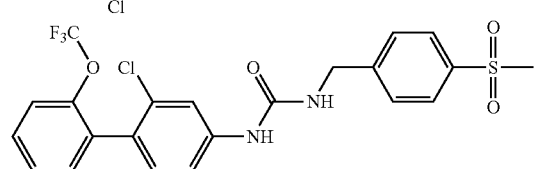

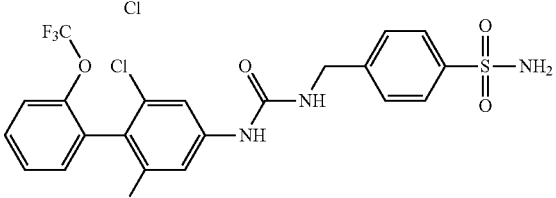

77
-continued
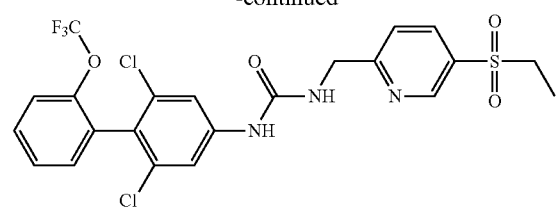
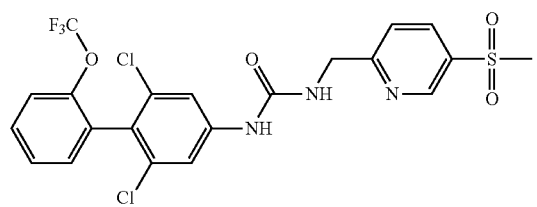
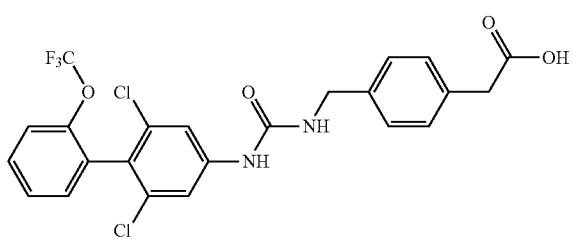
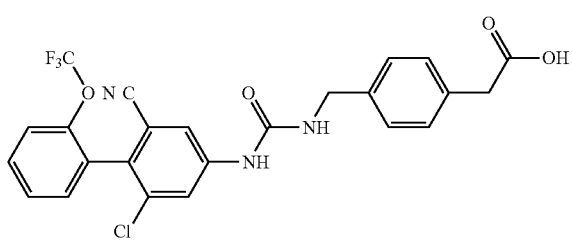
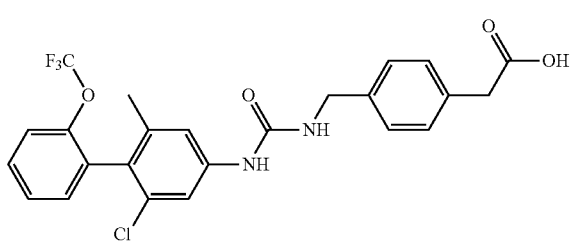
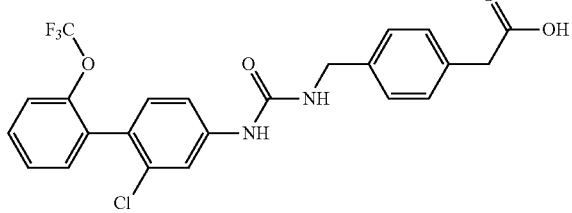
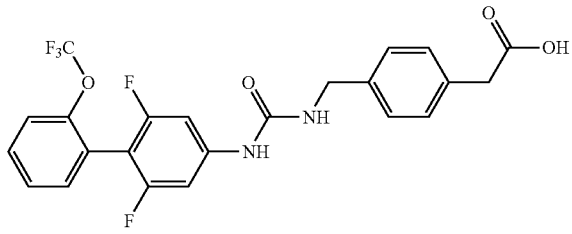
78
-continued
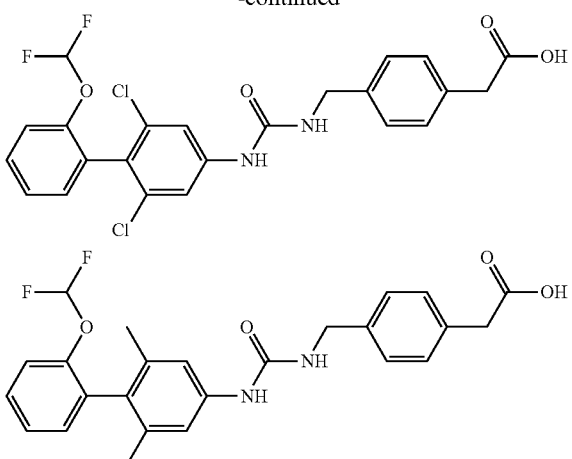
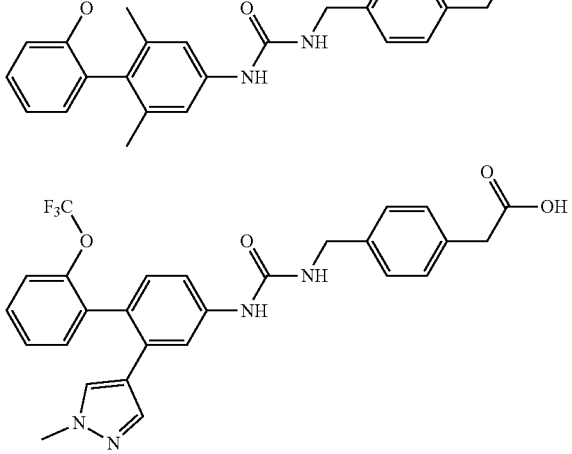
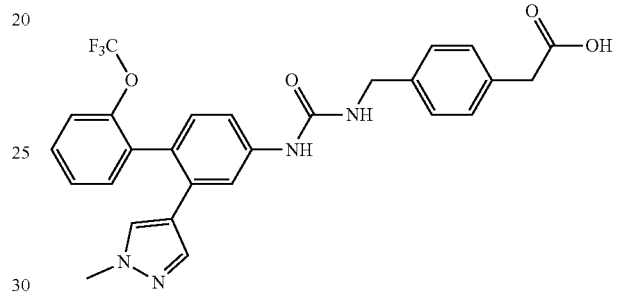
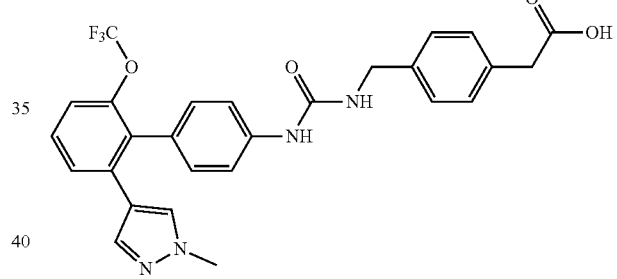
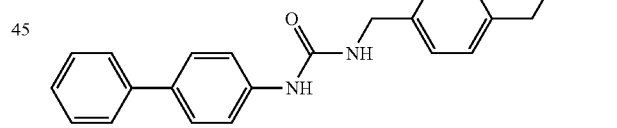
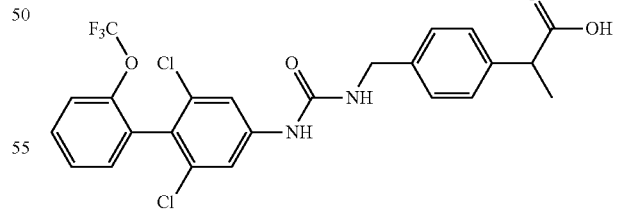
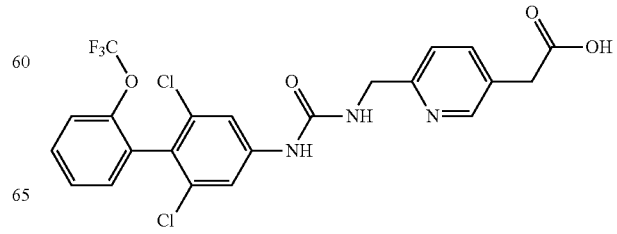

-continued

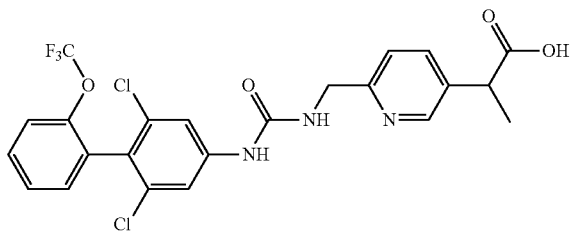

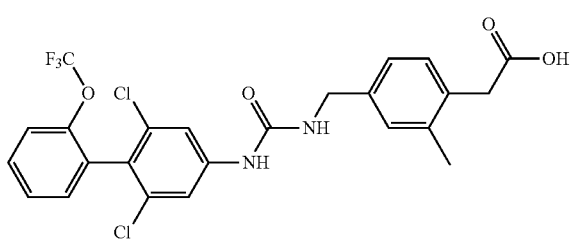

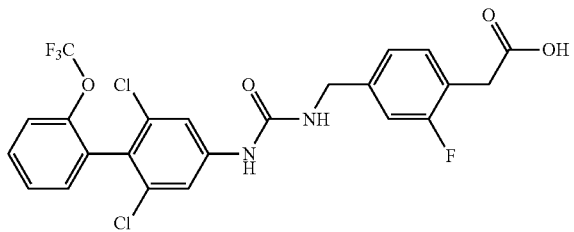

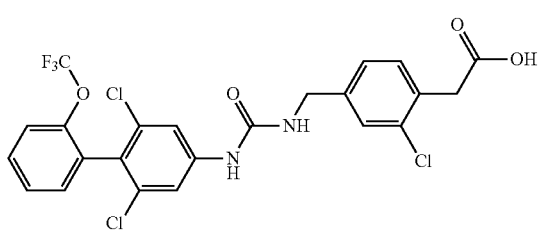

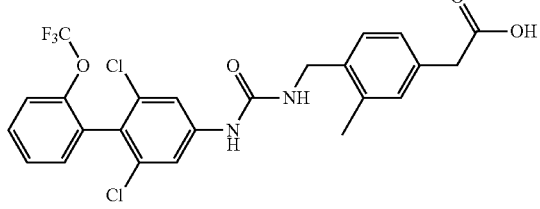

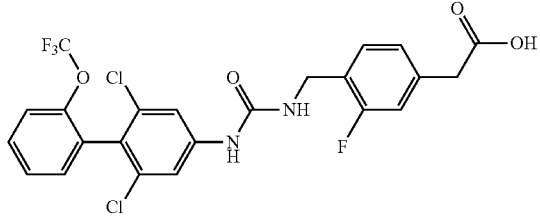

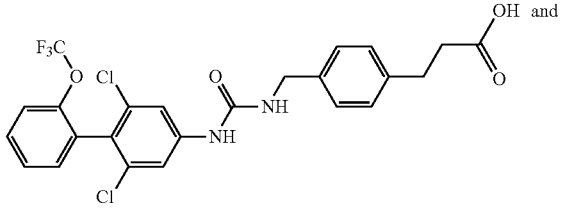

-continued

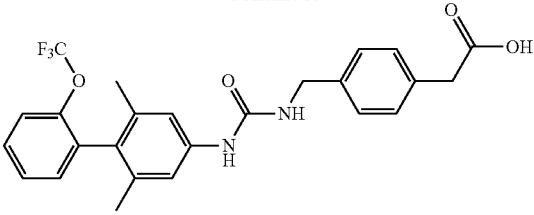

8. A pharmaceutical composition as a RORγt receptor inhibitor, comprising the compound or pharmaceutically acceptable salt thereof according to claim 1 as an active ingredient, and one or more pharmaceutically acceptable carriers.

9. A compound shown by formula II or a pharmaceutically acceptable salt thereof:

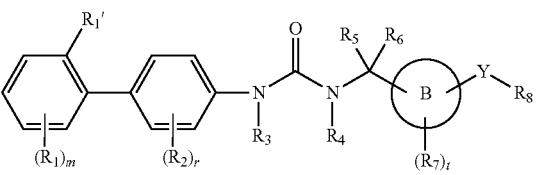

(II)

wherein:

B is phenyl or pyridyl;

$R_1$ is optionally selected from a group consisting of hydrogen, methyl, halogen, cyano, hydroxyl, —$CF_3$, —$CHF_2$, and —$CH_2F$;

$R_1'$ is selected from a group consisting of hydrogen, —$OCF_3$, —$OCHF_2$, —$CF_3$ and heteroaryl;

$R_2$ is optionally selected from a group consisting of hydrogen, halogen, cyano, hydroxyl, $C_1$-$C_6$ alkyl, halogen-substituted $C_1$-$C_6$ alkyl, C(O)OR$_a$ or cycloalkyl substituted $C_1$-$C_6$ alkyl, $C_3$-$C_6$ cycloalkyl, $C_3$-$C_6$ oxo (azo)heterocycloalkyl, $C_1$-$C_6$ alkoxyl, halogen-substituted $C_1$-$C_6$ alkoxyl, hydroxyl or $C_1$-$C_3$ alkoxyl substituted $C_1$-$C_3$ alkyl, phenyl, substituted heteroaryloxyl, $C_2$-$C_6$ alkenyl, halogen substituted aromatic ketone group, carboxyl or cyano substituted heteroaryl, —C(O)R$_a$, —(CH$_2$)$_n$NR$_{a1}$R$_{a2}$, —(CH$_2$)$_n$C(O)OR$_a$, —C(O)NR$_{a1}$R$_{a2}$;

$R_3$ and $R_4$ each is hydrogen, one of $R_5$ and $R_6$ is hydrogen, the other of $R_5$ and $R_6$ is $C_1$-$C_3$ alkyl or $C_1$-$C_3$ alkyl hydroxyl; or one of $R_3$ and $R_4$ is hydrogen, the other one of $R_3$ and $R_4$ is $C_1$-$C_3$ alkyl, $R_5$ and $R_6$ each is hydrogen;

$R_7$ is optionally selected from a group consisting of hydrogen, halogen, cyano, hydroxyl, $C_1$-$C_6$ alkyl, halogen-substituted $C_1$-$C_6$ alkyl, C(O)OR$_a$ or cycloalkyl substituted $C_1$-$C_6$ alkyl, $C_3$-$C_6$ cycloalkyl, $C_3$-$C_6$ oxo (azo)heterocycloalkyl, $C_1$-$C_6$ alkoxyl, halogen-substituted $C_1$-$C_6$ alkoxyl, hydroxyl or $C_1$-$C_3$ alkoxyl substituted $C_1$-$C_3$ alkyl, phenyl, substituted phenyl, phenoxyl, substituted phenoxyl, heterocyclyl, heterocyclooxyl, heteroaryl, heteroaryloxyl, $C_2$-$C_6$ alkenyl, halogen-substituted aromatic ketone group, carboxyl or cyano substituted heteroaryl, —C(O)R$_a$, —(CH$_2$)$_n$NR$_{a1}$R$_{a2}$, —(CH$_2$)$_n$C(O)OR$_a$ and —C(O)NR$_{a1}$R$_{a2}$;

Y is a covalent bond, when R$_8$ is

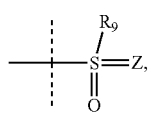

wherein Z is O, and R$_9$ is methyl or ethyl; or
Y is —CR$_{a1}$R$_{a2}$, when R$_8$ is

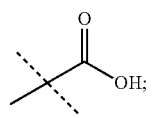

R$_a$, R$_{a1}$ and R$_{a2}$ are each independently selected from hydrogen or C$_1$-C$_3$ alkyl;

m, r, t and n are each independently selected from any integer value of 0~2.

10. A compound or a pharmaceutically acceptable salt thereof according to claim 9, wherein the compound is selected from:

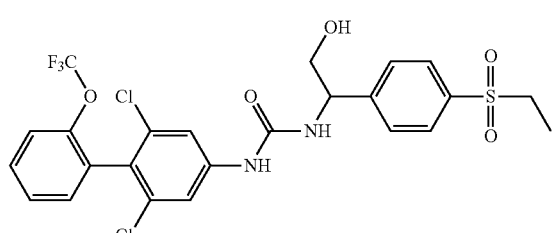

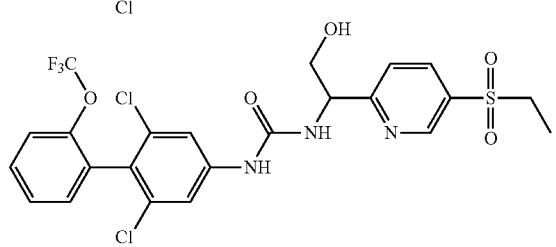

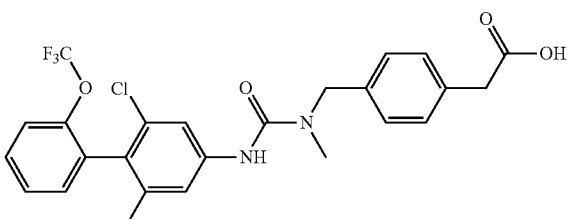

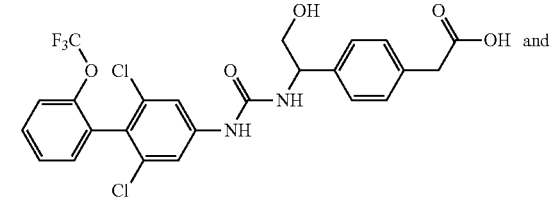

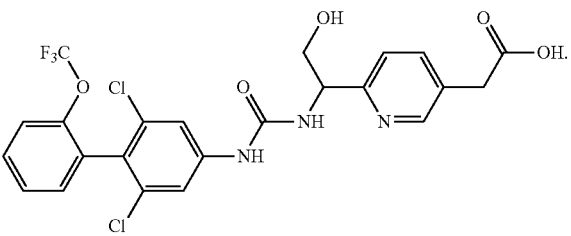

* * * * *